(12) United States Patent
Nakashima et al.

(10) Patent No.: US 8,431,248 B2
(45) Date of Patent: *Apr. 30, 2013

(54) CARBAZOLE DERIVATIVE, AND LIGHT EMITTING ELEMENT AND LIGHT EMITTING DEVICE USING THE CARBAZOLE DERIVATIVE

(75) Inventors: Harue Nakashima, Atsugi (JP); Sachiko Kawakami, Isehara (JP); Daisuke Kumaki, Tokamachi (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 132 days.

This patent is subject to a terminal disclaimer.

(21) Appl. No.: 13/037,392

(22) Filed: Mar. 1, 2011

(65) Prior Publication Data

US 2011/0147730 A1    Jun. 23, 2011

Related U.S. Application Data

(63) Continuation of application No. 10/583,028, filed as application No. PCT/JP2005/019349 on Oct. 14, 2005, now Pat. No. 7,901,791.

(30) Foreign Application Priority Data

Oct. 19, 2004  (JP) ................................ 2004-304225
Nov. 17, 2004  (JP) ................................ 2004-333344
Mar. 23, 2005  (JP) ................................ 2005-084533

(51) Int. Cl.
 *H01L 51/54*  (2006.01)
(52) U.S. Cl.
 USPC ........... 428/690; 428/917; 313/504; 313/505; 313/506; 548/440; 564/426; 564/427; 564/428; 564/429; 564/430; 564/431; 564/432; 564/433; 564/434

(58) Field of Classification Search .................. 428/690, 428/917; 313/540, 505, 506, 504; 548/440; 564/426–434
See application file for complete search history.

(56) References Cited

U.S. PATENT DOCUMENTS 6,602,619 B2   8/2003  Lin et al.
7,431,997 B2  10/2008  Hwang et al.
(Continued)

FOREIGN PATENT DOCUMENTS

EP   1661888 A    5/2006
EP   1862524 A   12/2007
(Continued)

OTHER PUBLICATIONS

International Search Report for Application No. PCT/JP2005/019349 dated Nov. 22, 2005.

(Continued)

*Primary Examiner* — Jennifer Chriss
*Assistant Examiner* — Gregory Clark
(74) *Attorney, Agent, or Firm* — Eric J. Robinson; Robinson Intellectual Property Law Office, P.C.

(57) ABSTRACT

It is an object of the present invention to provide a material which is excellent in a hole injecting property and a hole transporting property, and to provide a light emitting element and a light emitting device using a material which is excellent in a hole injecting property and a hole transporting property. The present invention provides a carbazole derivative represented by a general formula (I). The carbazole derivative according to the present invention is excellent in the hole injecting property. By using the carbazole derivative according to the present invention as a hole injecting material for a hole injecting layer of a light emitting element, a driving voltage can be reduced. In addition, a lower driving voltage, improvement of the luminous efficiency, a longer life time, and higher reliability can be realized by applying the material to a light emitting element or a light emitting device.

39 Claims, 40 Drawing Sheets

U.S. PATENT DOCUMENTS

| | | | |
|---|---|---|---|
| 7,737,627 B2 | 6/2010 | Hwang et al. | |
| 7,901,791 B2 * | 3/2011 | Nakashima et al. | 428/690 |
| 8,021,764 B2 | 9/2011 | Hwang et al. | |
| 8,021,765 B2 | 9/2011 | Hwang et al. | |
| 2004/0185299 A1 | 9/2004 | Ly | |
| 2005/0067951 A1 | 3/2005 | Richter et al. | |
| 2005/0225235 A1 | 10/2005 | Kim et al. | |
| 2006/0073357 A1 | 4/2006 | Brunner et al. | |
| 2007/0037011 A1 | 2/2007 | Nakashima et al. | |
| 2007/0231503 A1 | 10/2007 | Hwang et al. | |
| 2007/0249867 A1 | 10/2007 | Nakashima et al. | |
| 2008/0254318 A1 | 10/2008 | Nakashima et al. | |
| 2009/0058267 A1 | 3/2009 | Nakashima et al. | |

FOREIGN PATENT DOCUMENTS

| | | |
|---|---|---|
| JP | 62-280850 | 12/1987 |
| JP | 06-089040 | 3/1994 |
| JP | 06-346049 | 12/1994 |
| JP | 09-301934 | 11/1997 |
| JP | 10-310574 | 11/1998 |
| JP | 3210481 | 7/2001 |
| JP | 2004-026732 | 1/2004 |
| JP | 2004-323509 | 11/2004 |
| JP | 2005-290000 A | 10/2005 |
| JP | 2007-284411 | 11/2007 |
| WO | WO 03/008515 | 1/2003 |
| WO | WO 03/064373 | 8/2003 |
| WO | WO 2005/040117 | 5/2005 |
| WO | WO 2005/090512 | 9/2005 |
| WO | WO-2006/016684 | 2/2006 |

OTHER PUBLICATIONS

Written Opinion for Application No. PCT/JP2005/019349 dated Nov. 22, 2005.

Balionyte et al., "Potential hole-transport materials prepared by Ullmann coupling," Environmental and chemical physics, 2002, vol. 24, No. 1, pp. 30-34.

Search Report (Application No. 05795774.8) dated Jun. 22, 2010.

Thomas et al., "Light-Emitting Carbazole Derivatives: Potential Electroluminescent Materials," J. Am. Chem. Soc., 2001, 123, pp. 9404-9411.

Thomas et al., "Light-Emitting Carbazole Derivatives: Potential Electroluminescent Materials," J. Am. Chem. Soc., 2001, vol. 123, No. 38, pp. 9404-9411.

\* cited by examiner

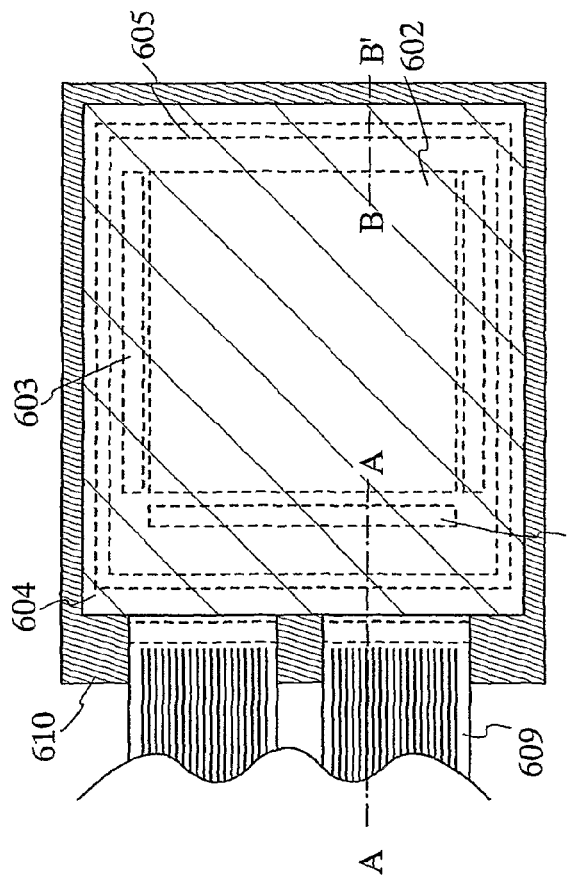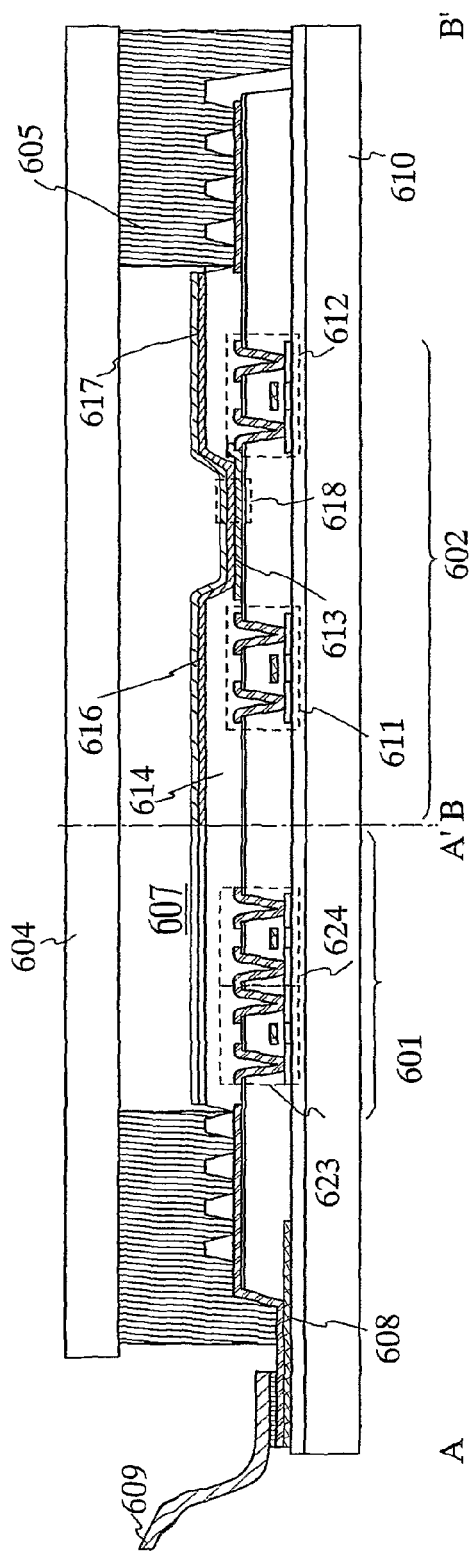
FIG. 11A
FIG. 11B

CARBAZOLE DERIVATIVE, AND LIGHT EMITTING ELEMENT AND LIGHT EMITTING DEVICE USING THE CARBAZOLE DERIVATIVE

TECHNICAL FIELD

The present invention relates to a carbazole derivative, a light emitting element which has a pair of electrodes and a layer containing a light emitting material that can provide luminescence by applying an electric field. In addition, the present invention relates to a light emitting device having the light emitting element.

BACKGROUND ART

A light-emitting element using a light emitting material has features of thinness and lightweight, high response speed, low direct-current voltage drive, and the like, and is expected to be applied to a next-generation flat panel display. A light emitting device in which light emitting elements are arranged in a matrix is said to have superiority in wide viewing angle and high visibility as compared with conventional liquid crystal display devices.

The light emission mechanism of a light-emitting element is as follows: electrons injected from a cathode and holes injected from an anode are recombined in the emission center in a light emitting layer to form a molecular exciton by applying a voltage to a pair of electrodes with the light emitting layer interposed therebetween, and energy is released to emit light when the molecular exciton returns to the ground state. An excited singlet state and an excited triplet state are known as an excited state, and it is believed that light can be emitted through either state.

As for the light-emitting element, there are many problems related to materials in improving characteristics thereof. Therefore, improvement of an element structure, development of a material, and the like are conducted in order to overcome these problems.

As an example of a material that is used for a layer containing a light emitting material, a material having a carbazole skeleton (carbazole derivative) excellent in photoconductivity can be cited. Specifically, 1,3,5-tris[4-(N-carbazolyl)phenyl]benzene (abbreviation: TCBP) can be cited (refer to Patent Document 1).

TCBP is proposed as a material for forming a hole transporting layer. However, many of materials having a carbazole skeleton have a larger ionization potential, and a hole injecting property from an electrode is not so good.

On the other hand, as a material that is often used for a hole injecting and a hole transporting material, for example, 4,4'-bis(N-{4-[N,N-bis(3-methylphenyl)amino]phenyl}-N-phenylamino)biphenyl (abbreviation: DNTPD) represented by a structural formula (a) can be cited (refer to Patent Document 2).

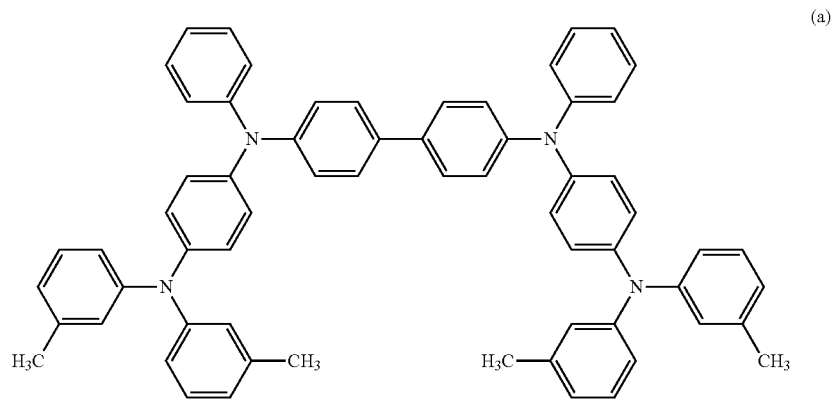 [SMILES: Cc1cccc(N(c2ccc(N(c3ccccc3)c3ccc(-c4ccc(N(c5ccccc5)c5ccc(N(c6cccc(C)c6)c6cccc(C)c6)cc5)cc4)cc3)cc2)c2cccc(C)c2)c1]

(a)

DNTPD has smaller ionization potential and superiority in the hole injecting property. In addition, DNTPD has a hole transporting property, and is often used for a hole injecting layer and a hole transporting layer of a light emitting element. However, it cannot be still said that DNTPD has sufficient properties, and development of a material which has better characteristics is required.

[Patent Document 1] Japanese Patent Application No. 3210481
[Patent Document 2] Japanese Patent Application Laid-Open No. H9-301934

DISCLOSURE OF INVENTION

In the view of the problems described above, it is an object of the present invention to provide a material that is excellent in the hole injecting property and the hole transporting property. In addition, it is an object of the present invention to provide a light emitting element and a light emitting device using the material that is excellent in the hole injecting property and the hole transporting property.

The present inventors found out that a carbazole derivative represented by the following general formula (1) has the excellent hole injecting and hole transporting properties.

Therefore, the present invention provides a carbazole derivative represented by the following general formula (1).

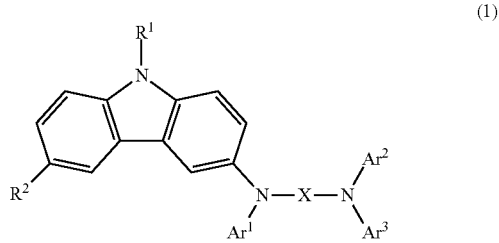

(1)

(In the formula, $R^1$ is one selected from the group consisting of hydrogen, an alkyl group having 1 to 6 carbon atoms, an aryl group having 6 to 25 carbon atoms, a heteroaryl group having 5 to 9 carbon atoms, an arylalkyl group, and an acyl group having 1 to 7 carbon atoms, $R^2$ is one selected from the group consisting of hydrogen, an alkyl group having 1 to 6 carbon atoms, and a substituent represented by a general formula (2), $Ar^1$ to $Ar^6$ may be identical or different, and are individually one selected from the group consisting of an aryl group having 6 to 25 carbon atoms and a heteroaryl group having 5 to 9 carbon atoms, and X and Y may be identical or different, and are individually one selected from the group consisting of a bivalent aromatic hydrocarbon group having 6 to 25 carbon atoms and a bivalent heterocyclic group having 5 to 10 carbon atoms.)

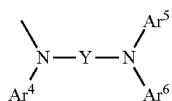

(2)

In the above general formula (1), it is preferable that $R^1$ be one selected from the group consisting of a methyl group, an ethyl group, a tert-butyl group, and a phenyl group.

Further, in the above general formula (1), it is preferable that $R^2$ be hydrogen or a tert-butyl group. Alternatively, it is preferable that $R^2$ have the structure of the general formula (2), and that $Ar^1$ and $Ar^4$, $Ar^2$ and $Ar^5$, $Ar^3$ and $Ar^6$, and X and Y have identical structures, respectively.

Specifically, a carbazole derivative having a structure represented by the following formula (3) is preferable.

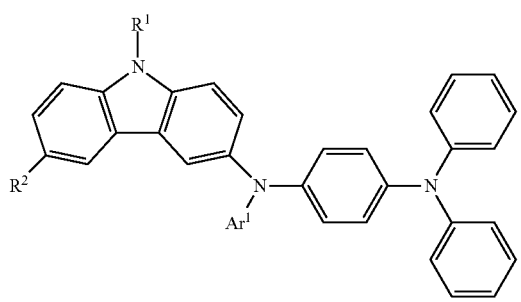

(3)

(In the formula, $R^1$ is one selected from the group consisting of hydrogen, an alkyl group having 1 to 6 carbon atoms, an aryl group having 6 to 25 carbon atoms, a heteroaryl group having 5 to 9 carbon atoms, an arylalkyl group, and an acyl group having 1 to 7 carbon atoms, $R^2$ is one selected from the group consisting of hydrogen, an alkyl group having 1 to 6 carbon atoms, and a substituent represented by a general formula (4), and $Ar^1$ and $Ar^2$ may be identical or different, and are one selected from the group consisting of an aryl group having 6 to 25 carbon atoms and a heteroaryl group having 5 to 9 carbon atoms.)

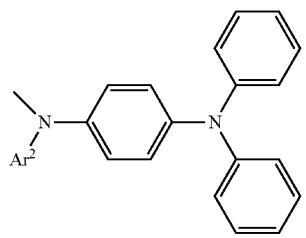

(4)

In the general formula (3), it is preferable that $R^1$ be one selected from the group consisting of a methyl group, an ethyl group, a tert-butyl group, and a phenyl group.

Further, in the general formula (3), it is preferable that $R^2$ be hydrogen or a tert-butyl group. Alternatively, it is preferable that $R^2$ have the structure of the general formula (4) and $Ar^1$ and $Ar^2$ have an identical structure.

A carbazole derivative having a structure represented by the following general formula (5) is more preferable.

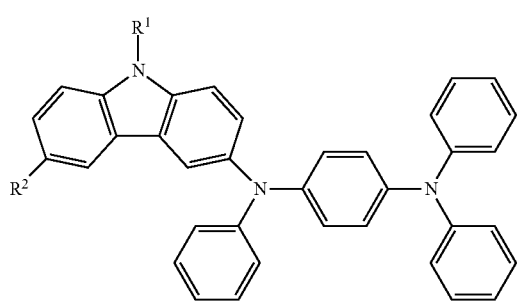

(5)

(In the formula, $R^1$ is one selected from the group consisting of hydrogen, an alkyl group having 1 to 6 carbon atoms, an aryl group having 6 to 25 carbon atoms, a heteroaryl group having 5 to 9 carbon atoms, an arylalkyl group, and an acyl group having 1 to 7 carbon atoms, and $R^2$ is one selected from the group consisting of hydrogen, an alkyl group having 1 to 6 carbon atoms, and a substituent represented by a structural formula (6).)

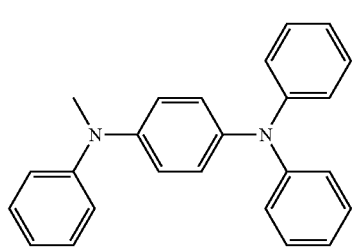

(6)

In the above general formula (5), it is preferable that $R^1$ be one selected from the group consisting of a methyl group, an ethyl group, a tert-butyl group, and a phenyl group.

Further, in the general formula (5), it is preferable that $R^2$ be hydrogen or a tert-butyl group. Alternatively, it is preferable that $R^2$ have the structure of the structural formula (6).

In addition, a carbazole derivative having a structure represented by the following general formula (103).

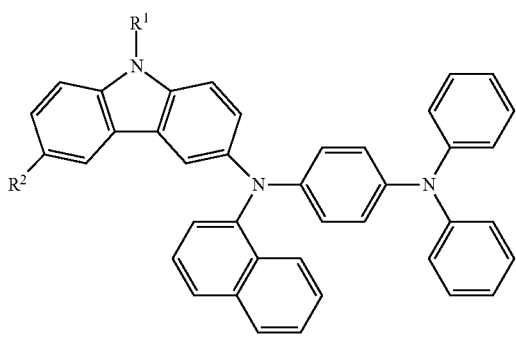

(In the formula, $R^1$ is one selected from the group consisting of hydrogen, an alkyl group having 1 to 6 carbon atoms, an aryl group having 6 to 25 carbon atoms, a heteroaryl group having 5 to 9 carbon atoms, an arylalkyl group, and an acyl group having 1 to 7 carbon atoms, and $R^2$ is one selected from the group consisting of hydrogen, an alkyl group having 1 to 6 carbon atoms, and a substituent represented by a structural formula (104).)

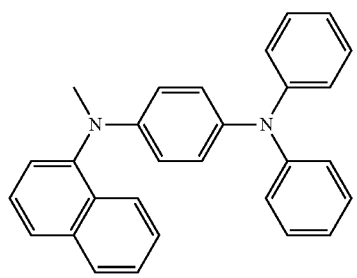

(104)

In the general formula (103), it is preferable that $R^1$ be one selected from the group consisting of a methyl group, an ethyl group, a tert-butyl group, and a phenyl group.

Further, in the general formula (103), it is preferable that $R^2$ be hydrogen or a tert-butyl group. Alternatively, it is preferable that $R^2$ have the structure of the structural formula (104).

Further, the carbazole derivatives according to the present invention can be used for a light emitting element.

Therefore, the light emitting element according to the present invention has features that a layer containing a light emitting material is interposed between a pair of electrodes, and the layer containing the light emitting material include a carbazole derivative represented by a general formula (1).

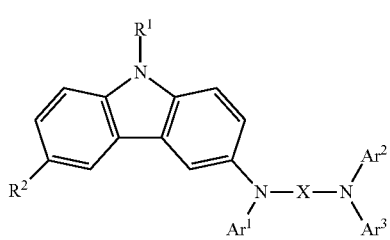

(1)

(In the formula, $R^1$ is one selected from the group consisting of hydrogen, an alkyl group having 1 to 6 carbon atoms, an aryl group having 6 to 25 carbon atoms, a heteroaryl group having 5 to 9 carbon atoms, an arylalkyl group, and an acyl group having 1 to 7 carbon atoms, $R^2$ is one selected from the group consisting of hydrogen, an alkyl group having 1 to 6 carbon atoms, and a substituent represented by the general formula (2), $Ar^1$ to $Ar^6$ may be identical or different, and are individually one selected from the group consisting of an aryl group having 6 to 25 carbon atoms and a heteroaryl group having 5 to 9 carbon atoms, and X and Y may be identical or different, and individually one selected from the group consisting of a bivalent aromatic hydrocarbon group having 6 to 25 carbon atoms or a bivalent heterocyclic group having 5 to 10 carbon atoms.)

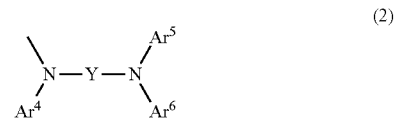

(2)

It is to be noted that the carbazole derivative according to the present invention is excellent in the hole injecting property, therefore, it is preferable that the carbazole derivative represented by the general formula (1) be included as a hole injecting material. Namely, it is preferable that the carbazole derivative according to the present invention be used for a layer being in contact with an anode.

Further, the carbazole derivative according to the present invention can be used as a hole transporting material since the carbazole derivative is excellent in the hole transporting property. Specifically, it is preferable that the carbazole derivative be used for a host material of a hole injecting layer, a hole transporting layer, and a light emitting layer in the layer containing the light emitting material.

It is to be noted that the anode according to the present invention indicates an electrode which injects holes into the layer containing the light emitting material. In addition, a cathode according to the present invention indicates an electrode which injects electrons into the layer containing the light emitting material.

Further, a light emitting device according to the present invention has features that the layer containing the light emitting material is interposed between a pair of electrodes, and the layer containing the light emitting material has a light emitting element including a carbazole derivative represented by the general formula (1). It is to be noted that the light emitting device in the present specification indicates an image display device, a light emitting device, or a light source (including lighting installation). In addition, the light emitting device also includes a module where a connector, for example, an FPC (Flexible printed circuit), a TAB (Tape Automated Bonding) tape or a TCP (Tape Carrier Package) is attached to a light emitting element, a module where a printed wiring board is attached to the end of a TAB tape or a TCP, and a module where an IC (Integrated Circuit) is directly mounted on a light emitting element by COG (Chip On Glass) method.

The carbazole derivative according to the present invention is excellent in the hole injecting property, and a driving voltage can be reduced by using the carbazole derivative as a hole injecting material for the hole injecting layer of the light emitting element.

Further, the carbazole derivative according to the present invention is also excellent in the hole transporting property, and can be used as a hole transporting material for a light emitting element.

Since the carbazole derivative according to the present invention is used for a light emitting element according to the present invention, a lower driving voltage, improvement of the luminous efficiency, longer lifetime, and higher reliability can be realized.

In addition, since a light emitting device according to the present invention has a light emitting element using the carbazole derivative according to the present invention, a light emitting device which has the high reliability can be provided.

BRIEF DESCRIPTION OF DRAWINGS

FIGS. 11A and 11B are explanatory views of a light-emitting device;

BEST MODE FOR CARRYING OUT THE INVENTION

Figure 1:
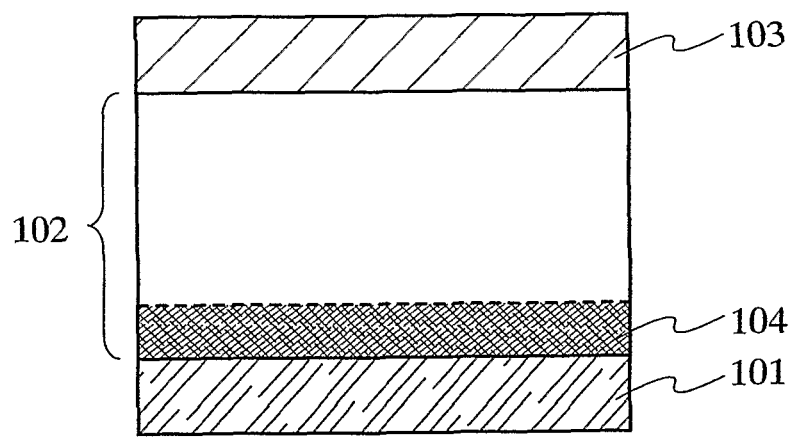
FIG. 1 is an explanatory view of a light-emitting element according to the present invention.

Hereinafter, embodiments of the present invention will be described in detail with the reference to the drawings. However, the present invention is not limited to the following description, and it is easily understood by those skilled art that various changes and modifications are possible, unless such changes and modifications depart from the content and the scope of the invention. Therefore, the present invention is not construed as being limited to the description of the following embodiments.

Embodiment 1

A carbazole derivative according to the present invention has a structure represented by a general formula (1).

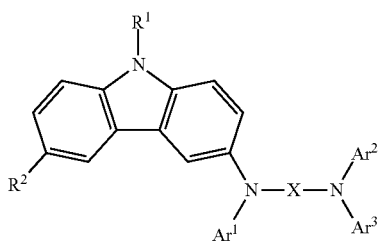
(1)

(In the formula, $R^1$ is one selected from the group consisting of hydrogen, an alkyl group having 1 to 6 carbon atoms, an aryl group having 6 to 25 carbon atoms, a heteroaryl group having 5 to 9 carbon atoms, an arylalkyl group, and an acyl group having 1 to 7 carbon atoms, $R^2$ is one selected from the group consisting of hydrogen, an alkyl group having 1 to 6 carbon atoms, and a substituent represented by a general formula (2), $Ar^1$ to $Ar^6$ may be identical or different, and are individually one selected from the group consisting of an aryl group having 6 to 25 carbon atoms and a heteroaryl group having 5 to 9 carbon atoms, and X and Y may be identical or different, and are individually one selected from the group consisting of a bivalent aromatic hydrocarbon group having 6 to 25 carbon atoms and a bivalent heterocyclic having 5 to 10 carbon atoms.)

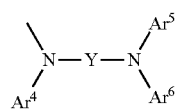
(2)

As the alkyl group having 1 to 6 carbon atoms, specifically, a methyl group, an ethyl group, an n-propyl group, an n-butyl group, an n-hexyl group and the like can be used. Further, an alkyl group having a branch such as an iso-propyl group and a tert-butyl group may be used.

As the aryl group having 6 to 25 carbon atoms, specifically, a phenyl group, 4-biphenyl group, a 1-napthyl group, a 2-napthyl group, a 9-anthryl group, a 9-phenanthryl group, a 1-pyrenyl group, a 9,9'-dimethyl-2-fluorenyl group, a spiro-9,9'-bifluorene-2-yl group, and the like can be used. Further, an aryl group having a substituent such as an m-tolyl group, a p-tolyl group, a 2-fluorophenyl group, a 3-fluorophenyl group, and a 4-fluorophenyl group may be used.

As the heteroaryl group having 5 to 9 carbon atoms, specifically, a 2-pyridyl group, an 8-quinolyl group, a 3-quinolyl group, and the like can be used.

As the arylalkyl group, specifically, a benzyl group and the like can be used.

As the acyl group having 1 to 7 carbon atoms, specifically, an acetyl group, a benzoyl group, a propionyl group, and the like can be used.

Further, as the bivalent aromatic hydrocarbon group having 6 to 25 carbon atoms, specifically, bivalent aromatic hydrocarbon groups represented by following structural formulas (7) to (18) can be used.

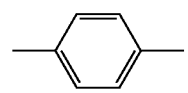
(7)

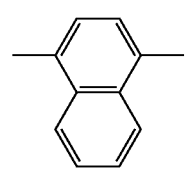
(8)

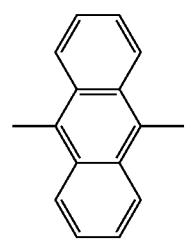
(9)

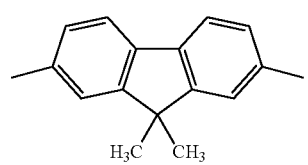
(10)

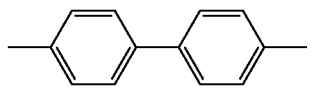
(11)

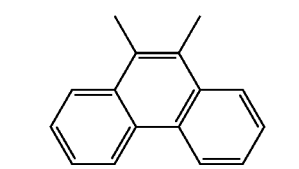
(12)

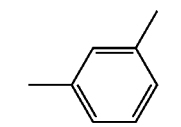
(13)

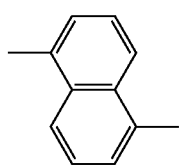
(14)

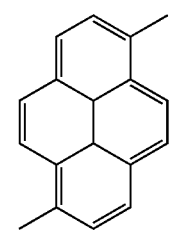
(15)

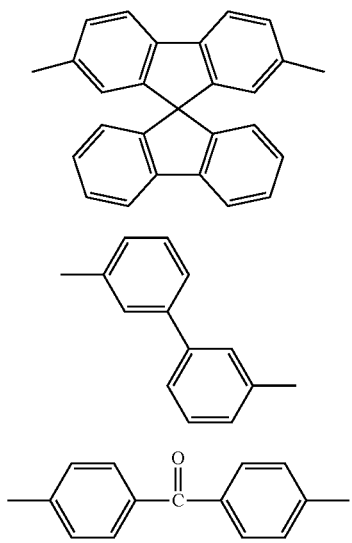

(16)

(17)

(18)

Further, as the bivalent heterocyclic group having 5 to 10 carbon atoms, specifically, bivalent heterocyclic groups represented by following structural formulas (19) to (24) can be used.

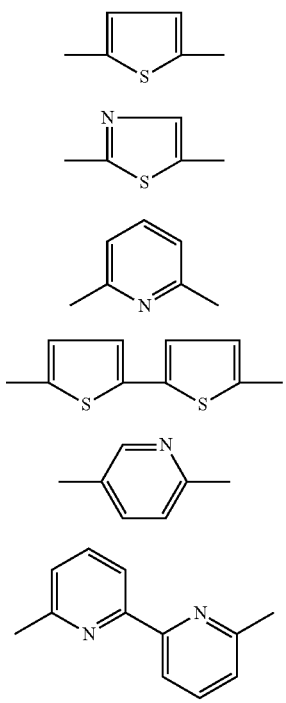

(19)

(20)

(21)

(22)

(23)

(24)

In the general formula (1), it is preferable that $R^1$ be one selected from the group consisting of a methyl group, an ethyl group, a tert-butyl group, and a phenyl group.

Further, in the general formula (1), it is preferable that $R^2$ be hydrogen or a tert-butyl group. Alternatively, it is preferable that $R^2$ have a structure of the general formula (2), and that $Ar^1$ and $Ar^4$, $Ar^2$ and $Ar^5$, $Ar^3$ and $Ar^6$, and X and Y have identical structures, respectively.

Further, in the carbazole derivative which has a structure represented by the above general formula (1), a carbazole derivative which has a structure represented by the following general formula (3) is easy to synthesize, and preferable.

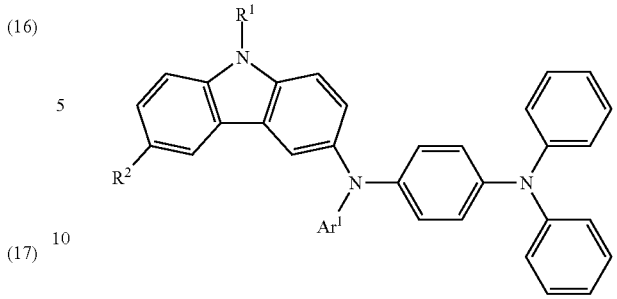

(3)

(In the formula, $R^1$ is one selected from the group consisting of hydrogen, an alkyl group having 1 to 6 carbon atoms, an aryl group having 6 to 25 carbon atoms, a heteroaryl group having 5 to 9 carbon atoms, an arylalkyl group, and an acyl group having 1 to 7 carbon atoms, $R^2$ is one selected from the group consisting of hydrogen, an alkyl group having 1 to 6 carbon atoms, and a substituent represented by a general formula (4), and $Ar^1$ and $Ar^2$ may be identical and different, and are individually one selected from the group consisting of an aryl group having 6 to 25 carbon atoms or a heteroaryl group having 5 to 9 carbon atoms.)

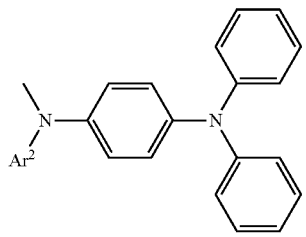

(4)

In the general formula (3), it is preferable that $R^1$ be one selected from the group consisting of a methyl group, an ethyl group, a tert-butyl group, and a phenyl group.

Further, in the general formula (3), it is preferable that $R^2$ be hydrogen or a tert-butyl group. Alternatively, it is preferable that $R^2$ have a structure of the general formula (4), and that $Ar^1$ and $Ar^2$ have an identical structure.

Specifically, a carbazole derivative which has a structure represented by a following general formula (5) is more preferable.

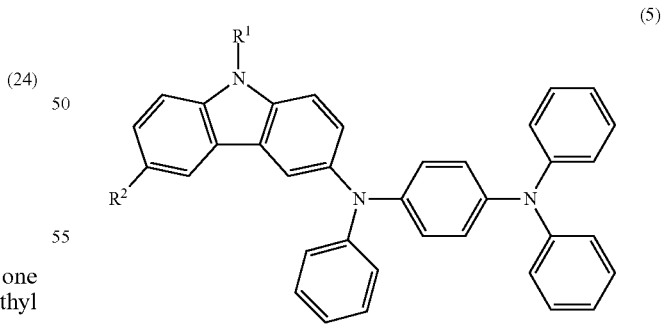

(5)

(In the formula, $R^1$ is one selected from the group consisting of hydrogen, an alkyl group having 1 to 6 carbon atoms, an aryl group having 6 to 25 carbon atoms, a heteroaryl group having 5 to 9 carbon atoms, an arylalkyl group, and an acyl group having 1 to 7 carbon atoms, and $R^2$ is one selected from the group consisting of hydrogen, an alkyl group having 1 to 6 carbon atoms, and a substituent represented by a structural formula (6).)

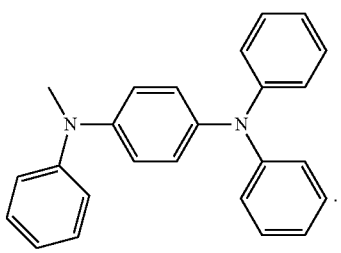

(6)

In the general formula (5), it is preferable that $R^1$ be one selected from the group consisting of a methyl group, an ethyl group, a tert-butyl group, and a phenyl group.

In the above general formula (5), it is preferable that $R^2$ be hydrogen or a tert-butyl group. Otherwise, it is preferable that $R^2$ have a structure of the structural formula (6).

Further, a carbazole derivative which has a structure represented by a following general formula (103) is more preferable.

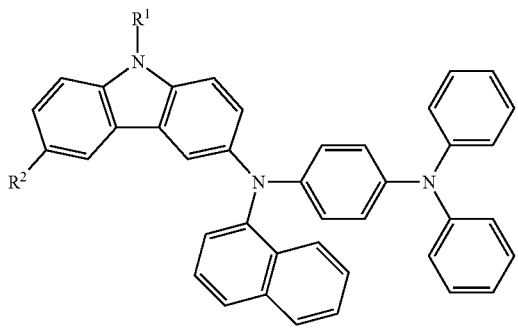

(103)

(In the formula, $R^1$ is one selected from the group consisting of hydrogen, an alkyl group having 1 to 6 carbon atoms, an aryl group having 6 to 25 carbon atoms, a heteroaryl group having 5 to 9 carbon atoms, an arylalkyl group, and an acyl group having 1 to 7 carbon atoms, and $R^2$ is one selected from the group consisting of hydrogen, an alkyl group having 1 to 6 carbon atoms, and a substituent represented by a structural formula (104).)

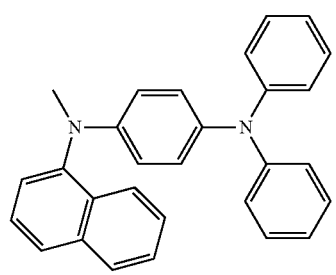

(104)

In the general formula (103), it is preferable that $R^1$ be one selected from the group consisting of a methyl group, an ethyl group, a tert-butyl group, and a phenyl group.

Further, in the general formula (103), it is preferable that $R^2$ be hydrogen or a tert-butyl group. Otherwise, it is preferable that $R^2$ have the structure of the structural formula (104).

Further, specific examples of the carbazole derivative according to the present invention include carbazole derivatives represented by the following structural formulas (25) to (102). However, the present invention is not limited to these.

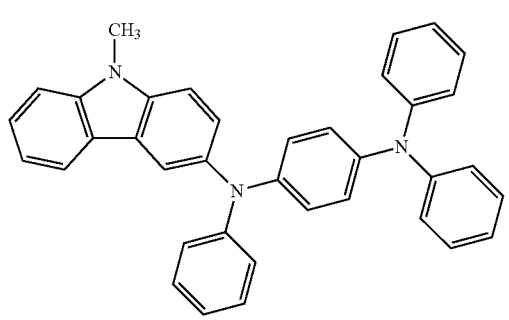

(25)

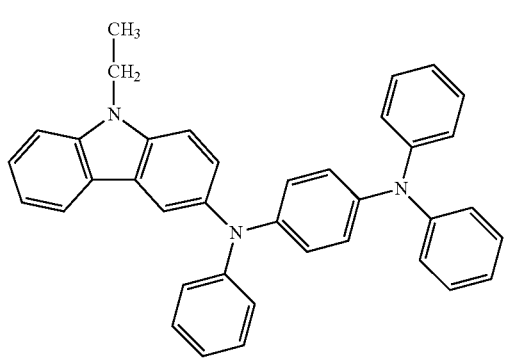

(26)

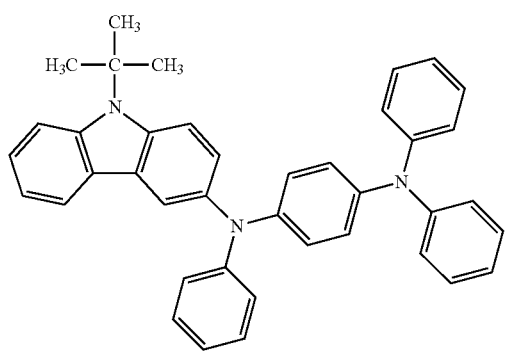

(27)

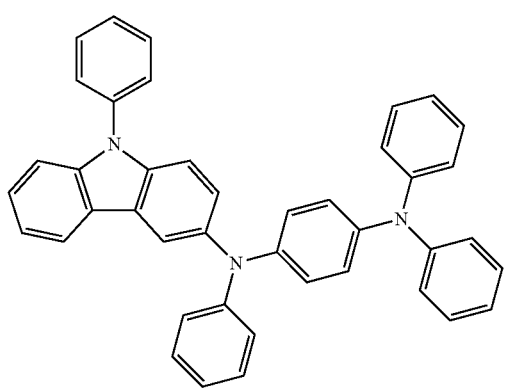

(28)

-continued
(29)
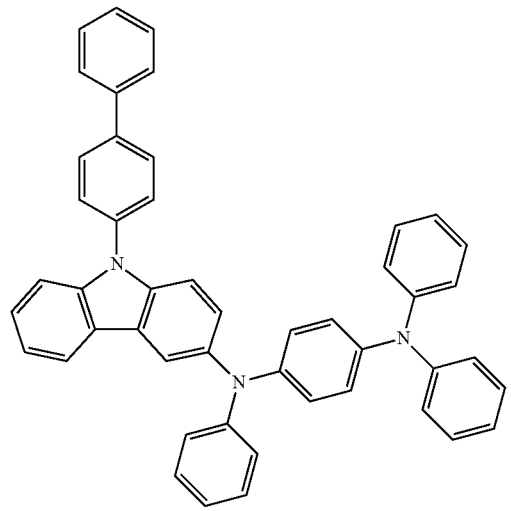
(30)
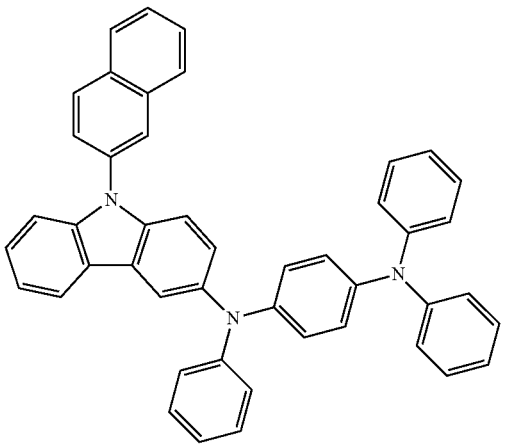
(31)
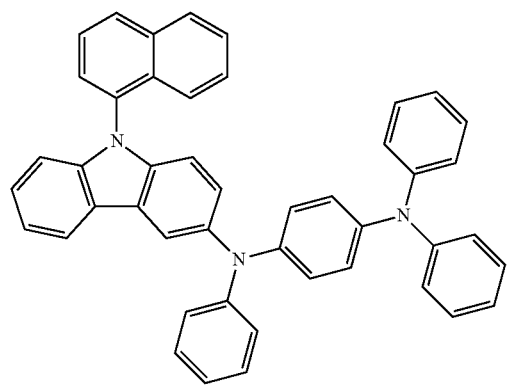
(32)
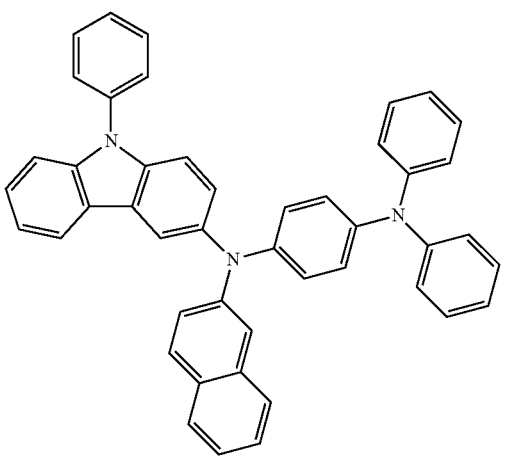
(33)
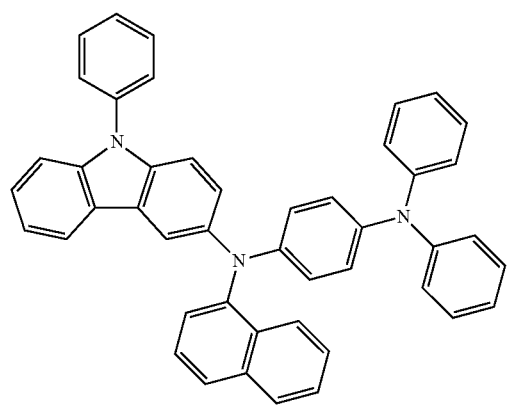
(34)
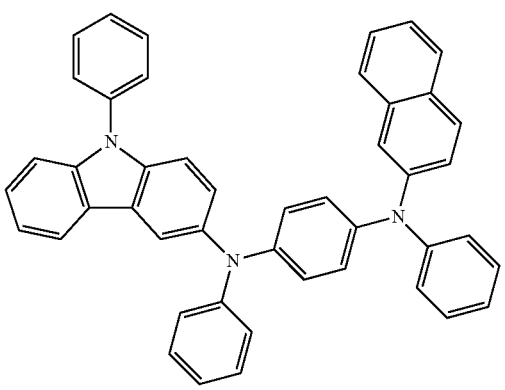

-continued
(35)
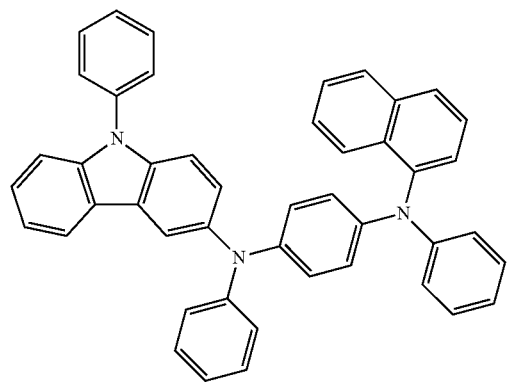
(36)
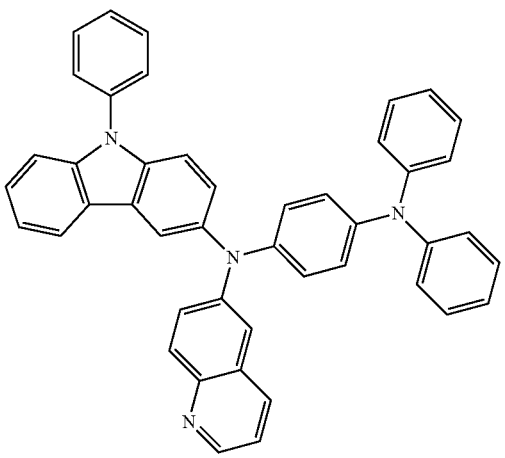
(37)
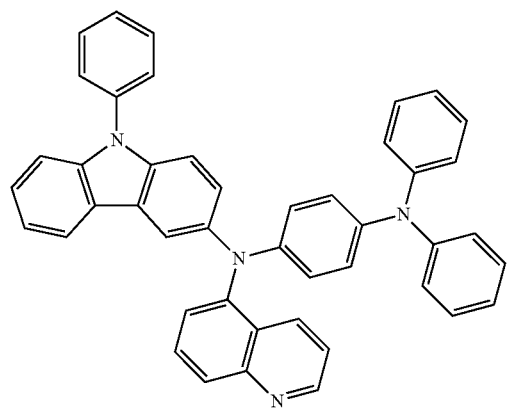
(38)
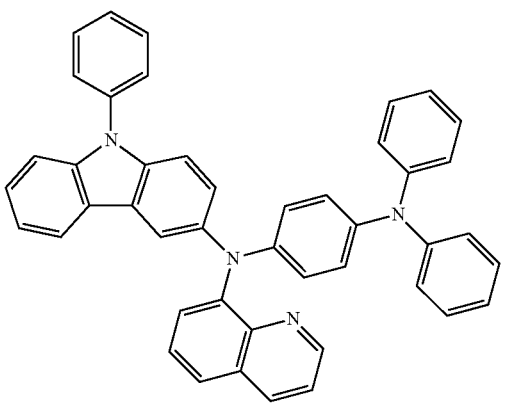
(39)
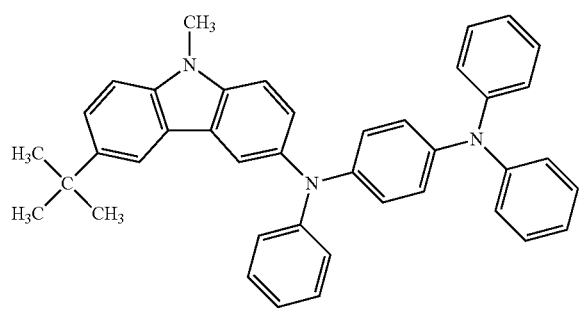
(40)
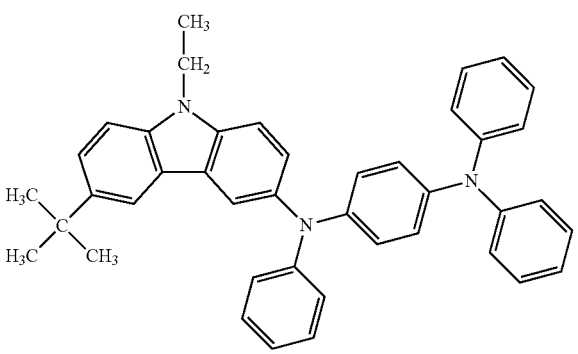
(41)
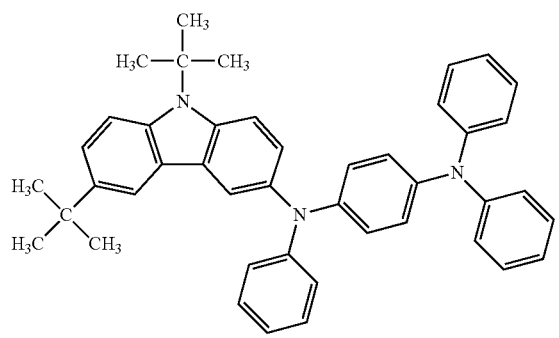
(42)
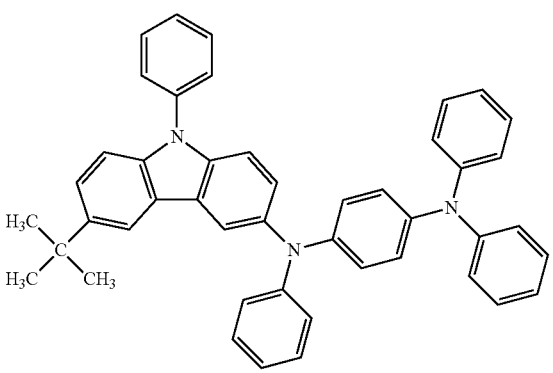

-continued
(43)
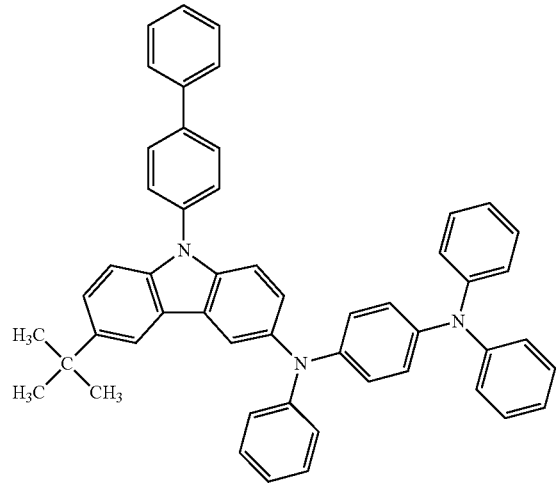
(44)
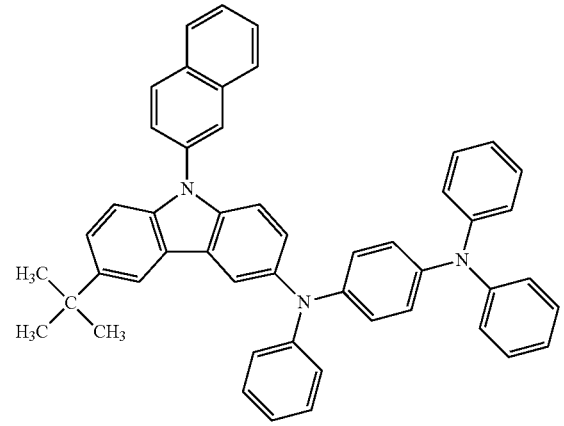
(45)
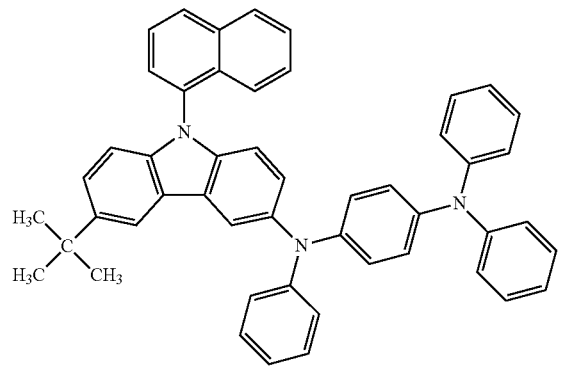
(46)
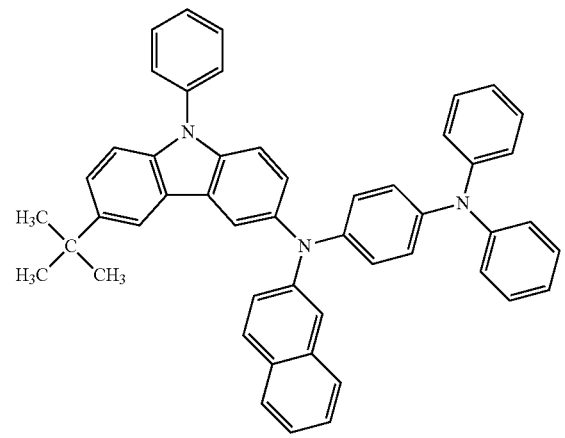
(47)
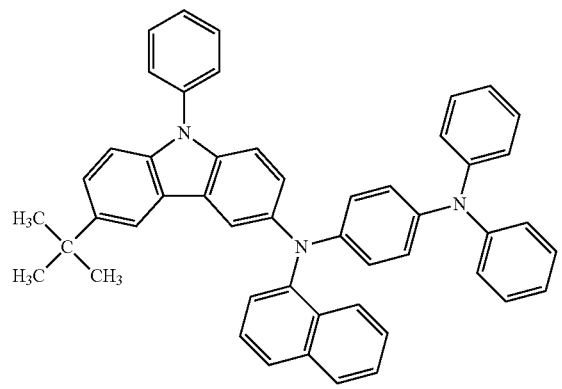
(48)
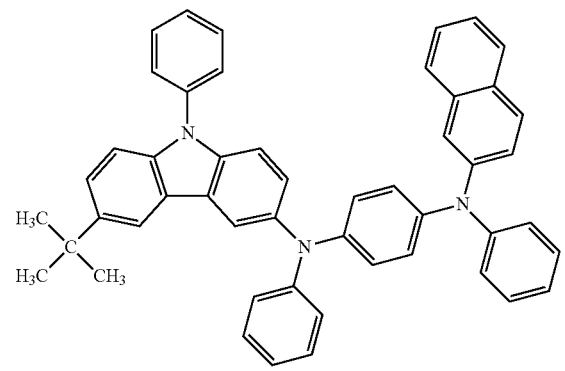

-continued
(49)
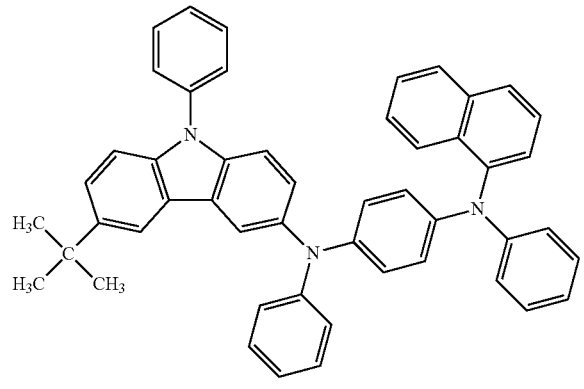
(50)
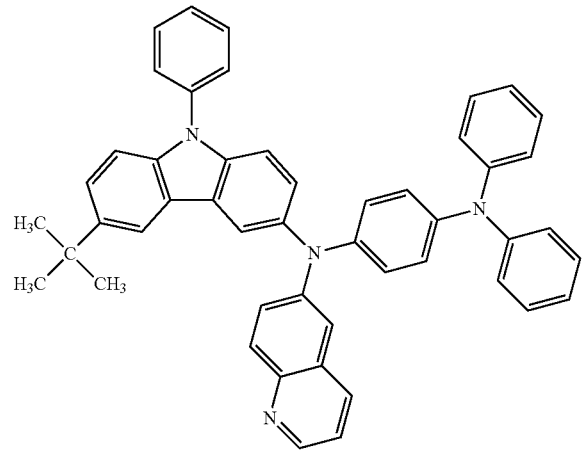
(51)
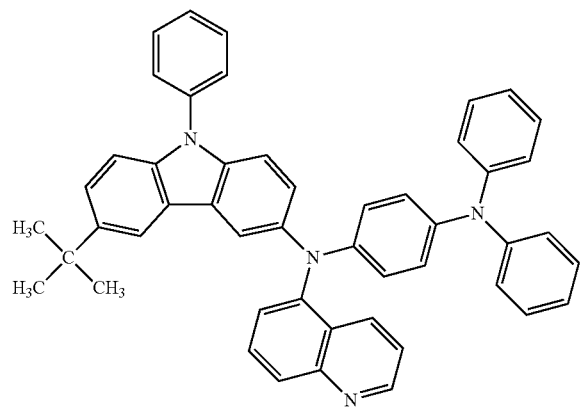
(52)
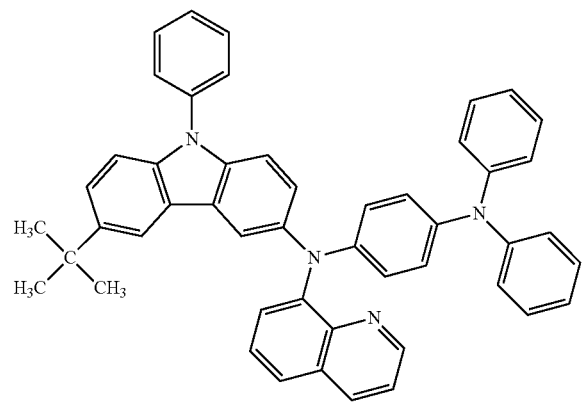
(53)
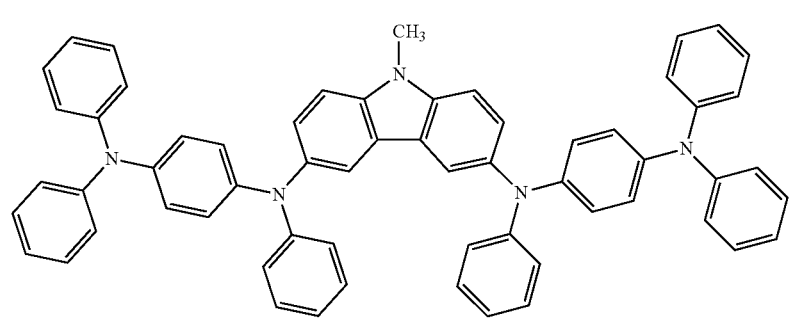
(54)
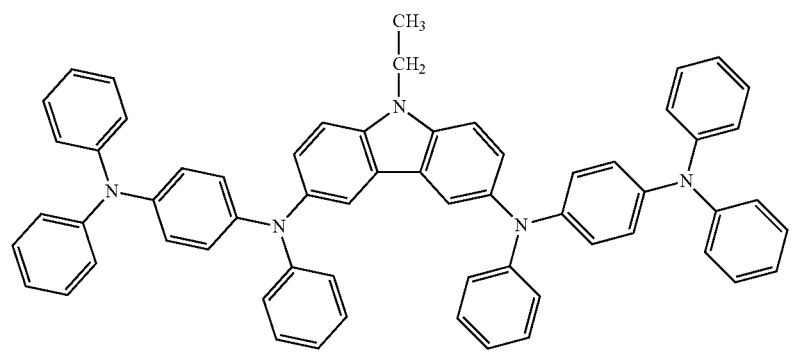

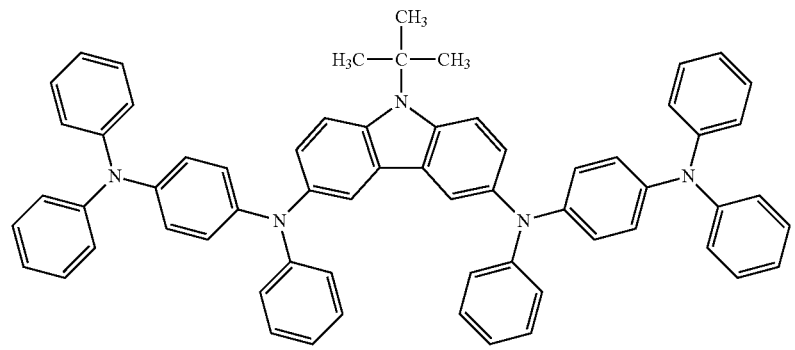
(55)
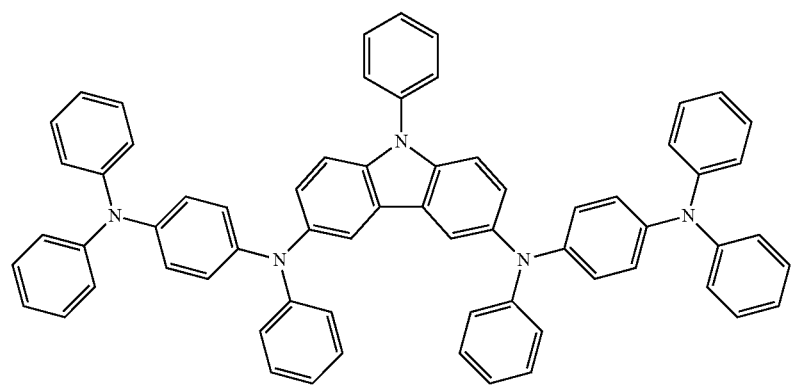
(56)
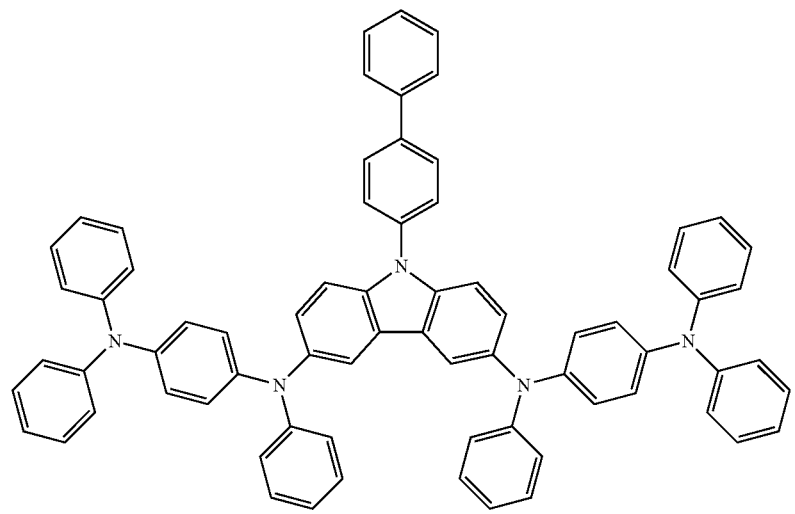
(57)

-continued
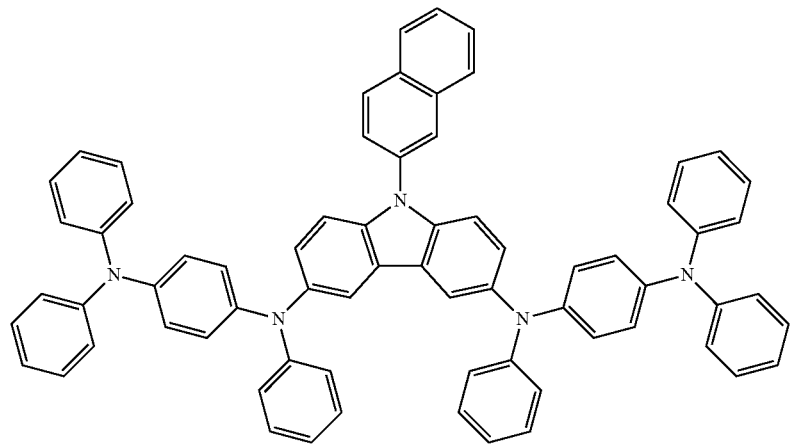
(58)
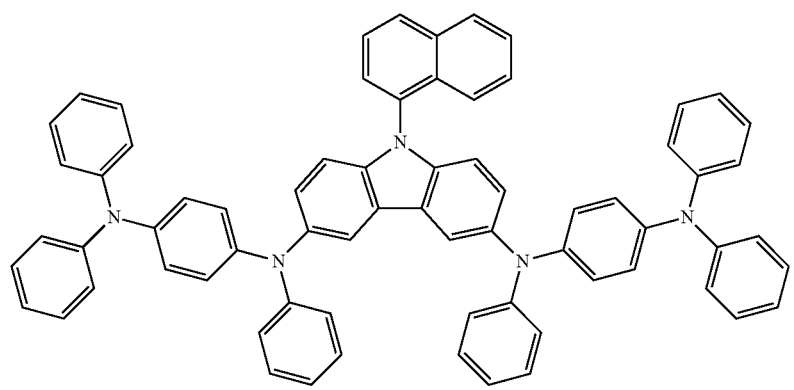
(59)
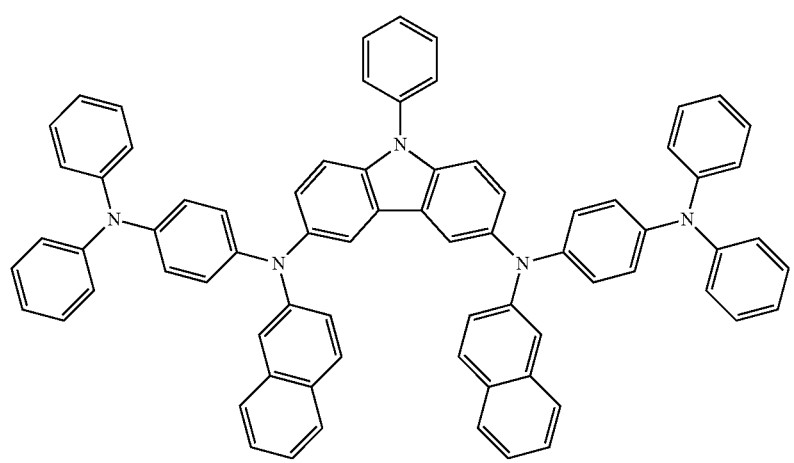
(60)

-continued
(61)
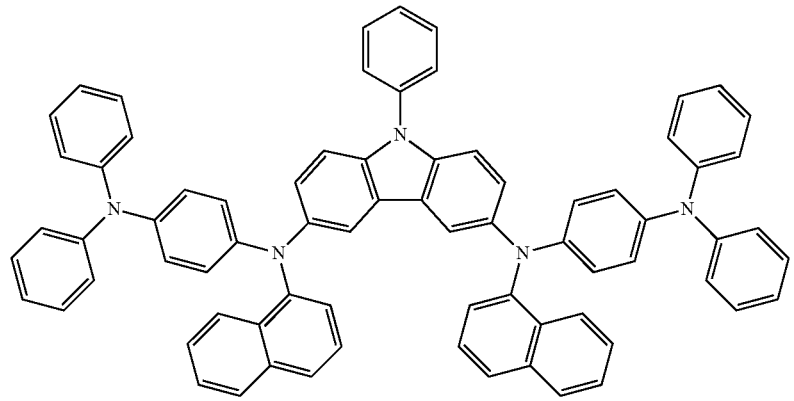
(62)
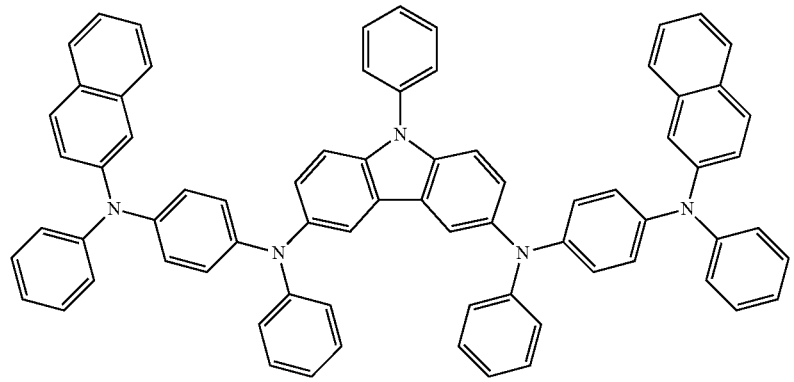
(63)
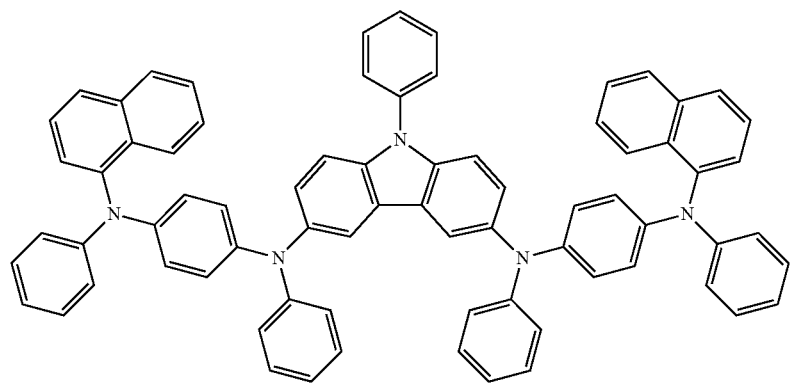
(64)
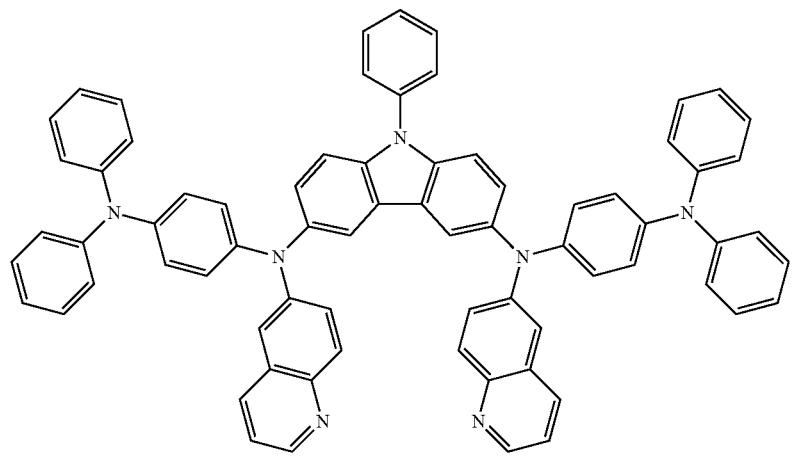

(65)
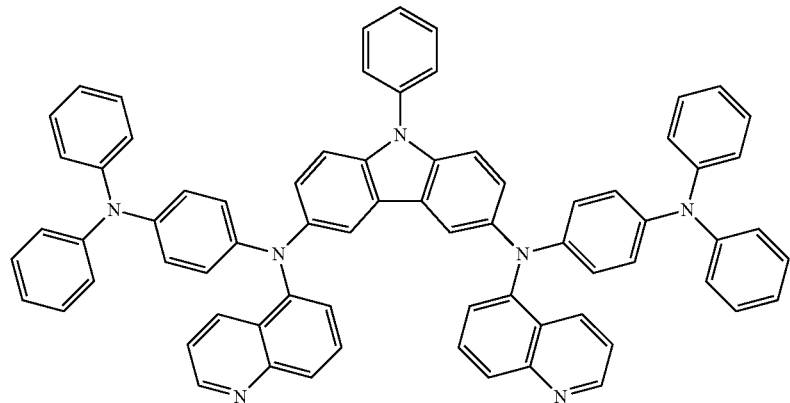
(66)
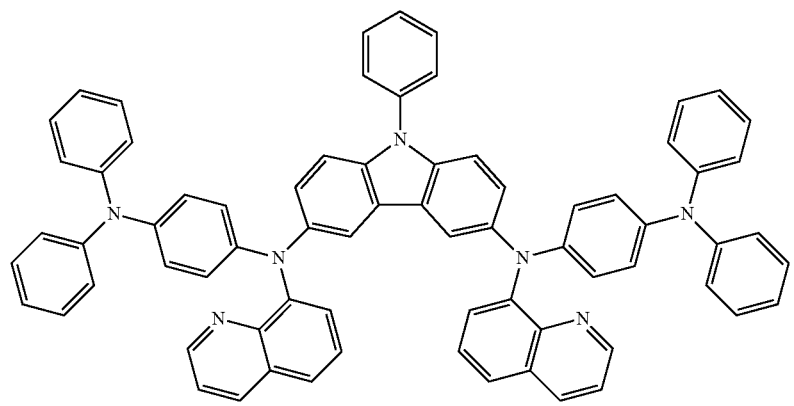
(67)
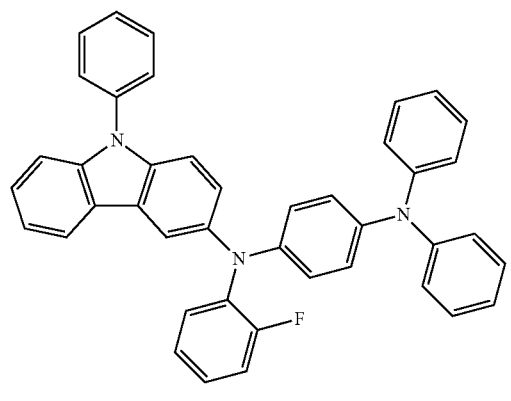
(68)

(69)
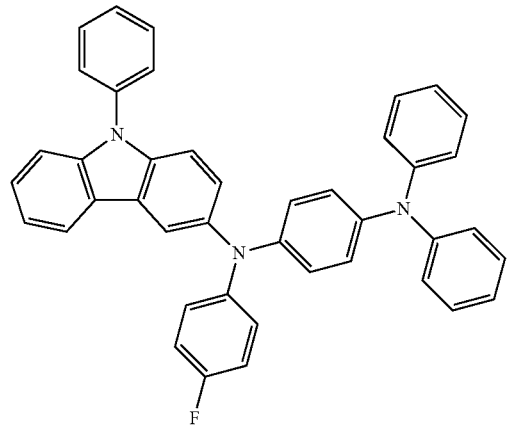
(70)
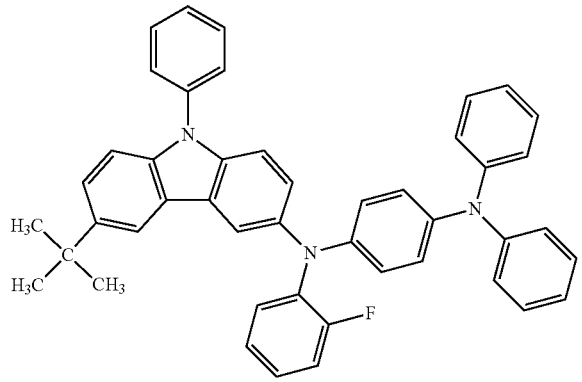
(71)
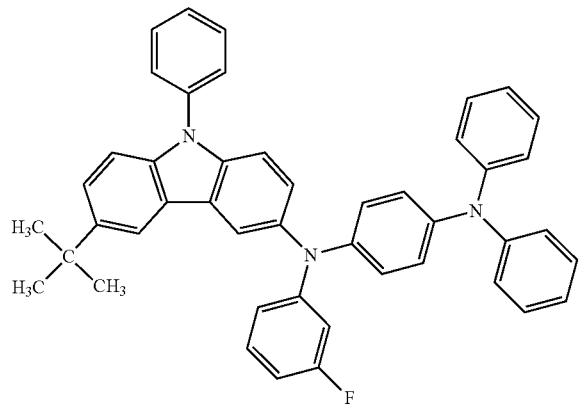
(72)
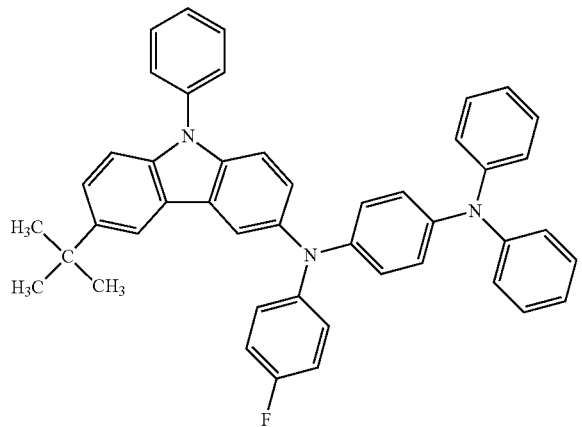
(73)
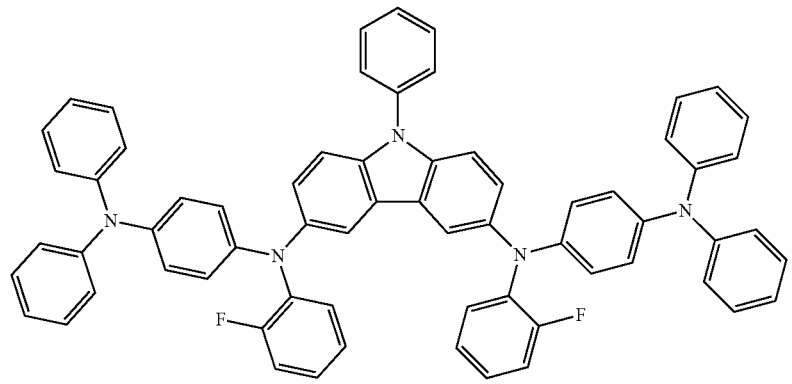

(74)
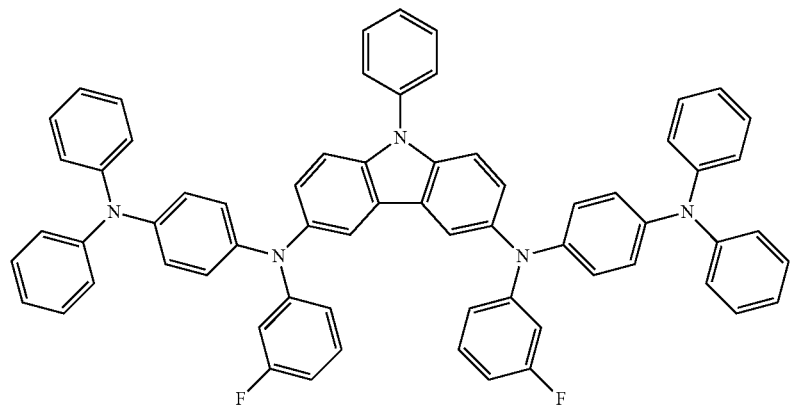
(75)
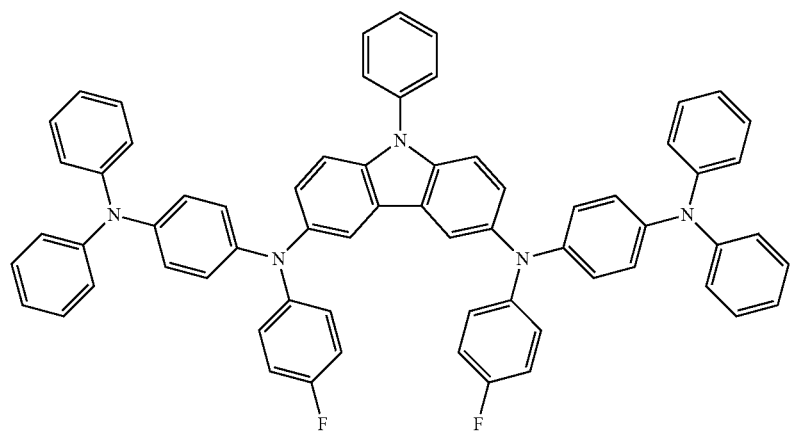
(76)
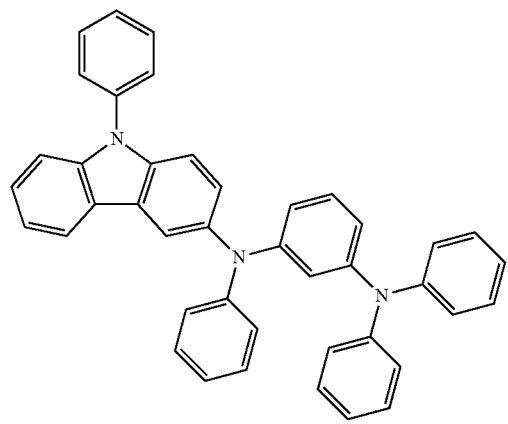
(77)
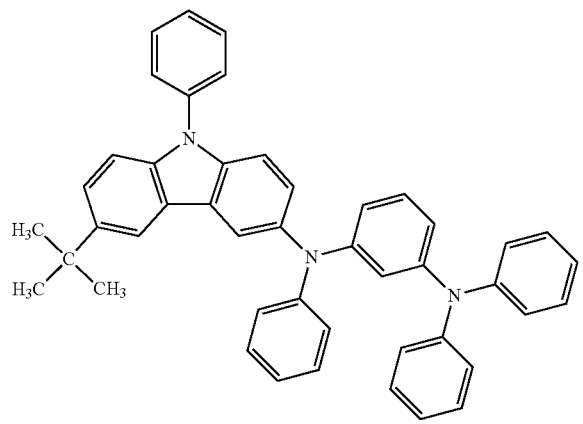

-continued
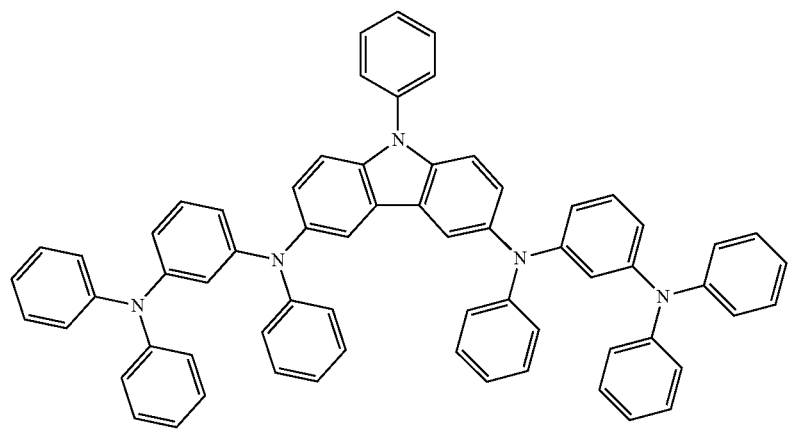
(78)
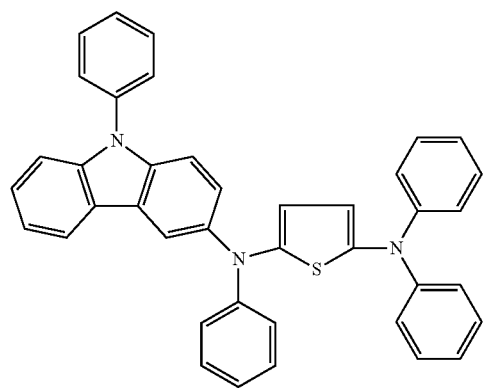
(79)
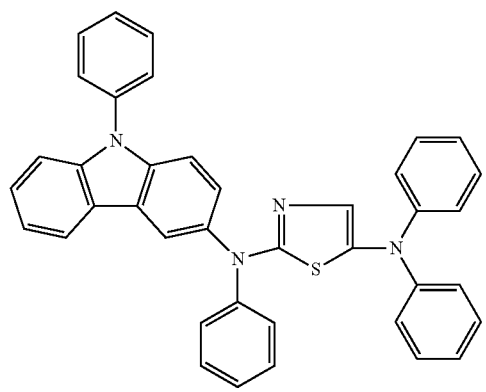
(80)
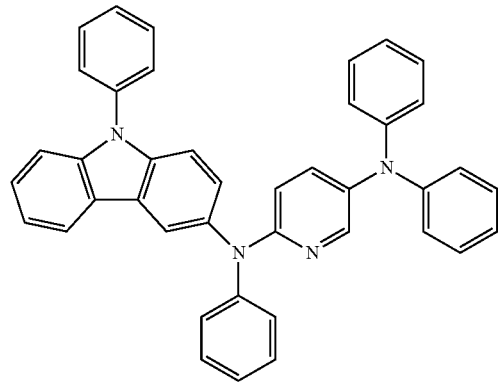
(81)
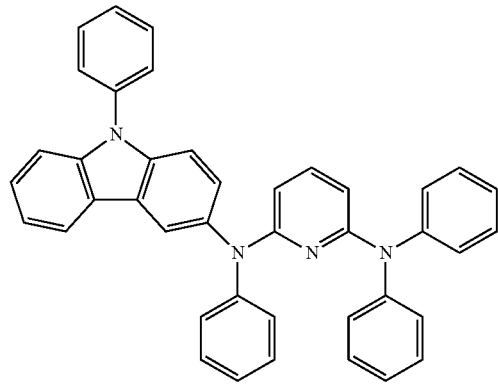
(82)
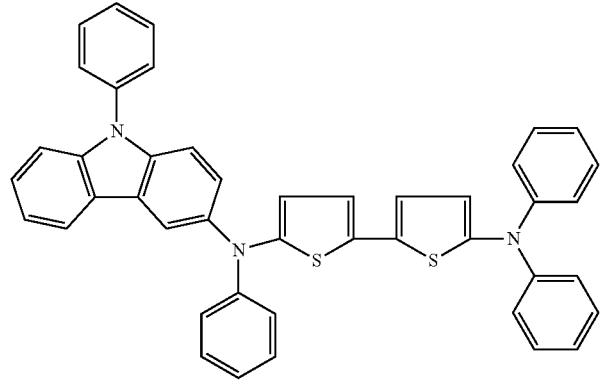
(83)
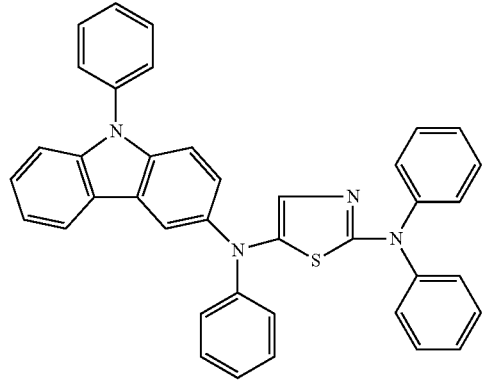
(84)

-continued
(85)
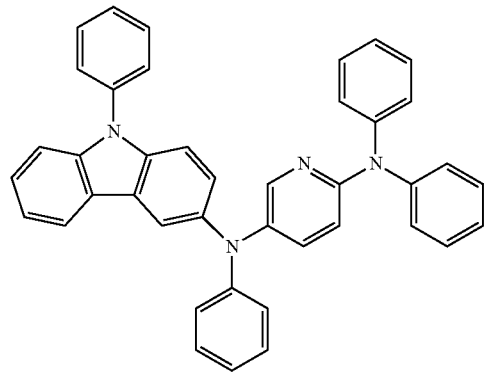
(86)
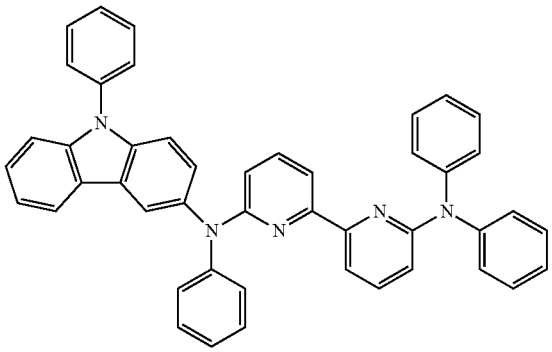
(87)
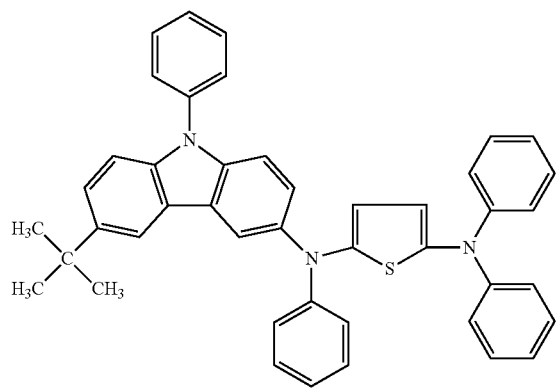
(88)
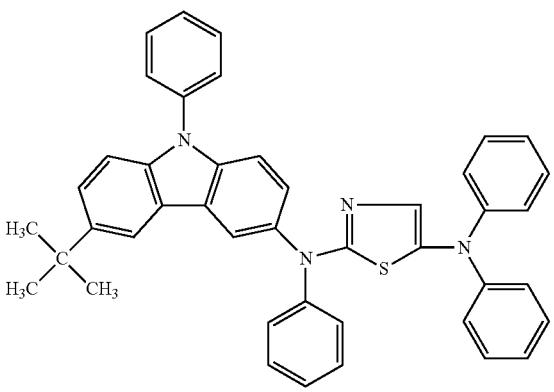
(89)
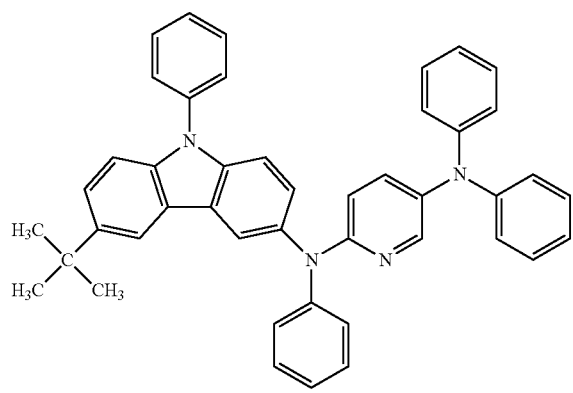
(90)
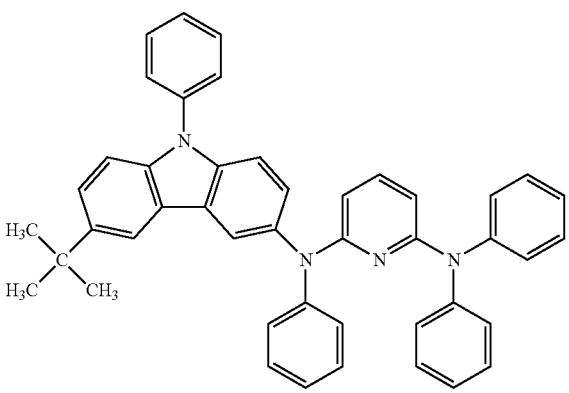
(91)
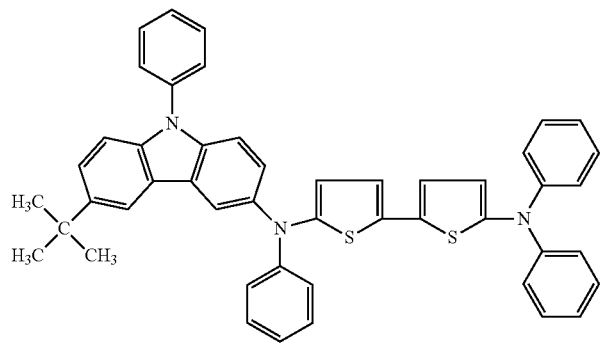
(92)
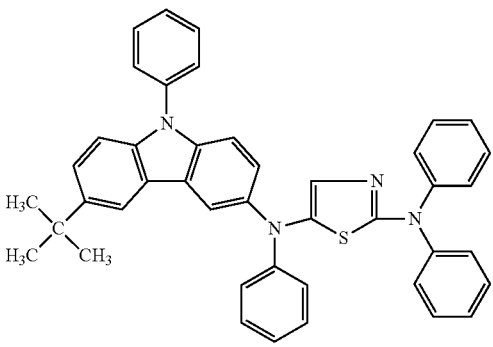

-continued
(93)
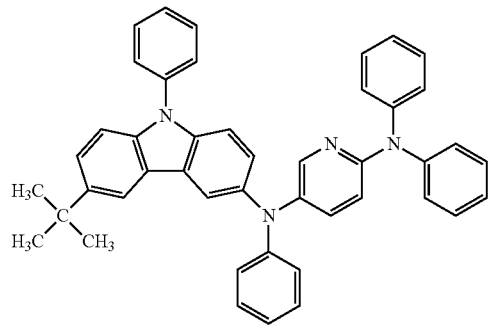
(94)
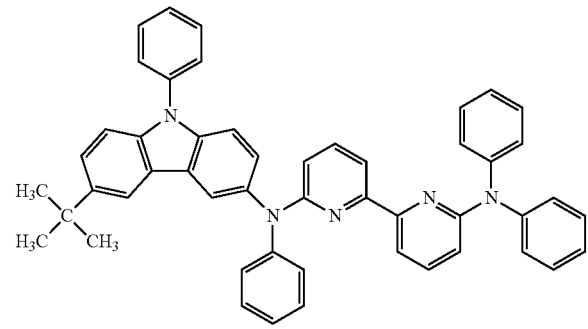
(95)
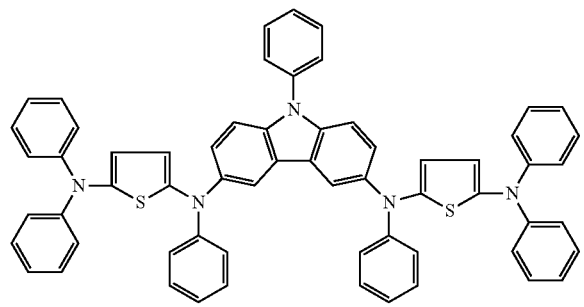
(96)
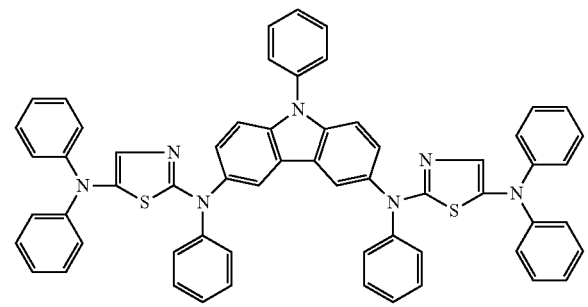
(97)
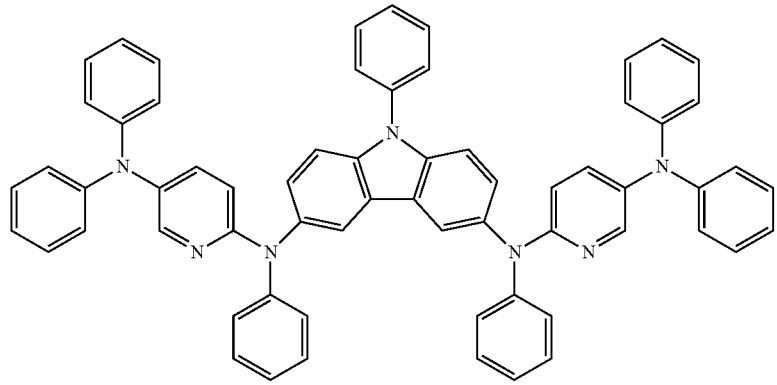
(98)
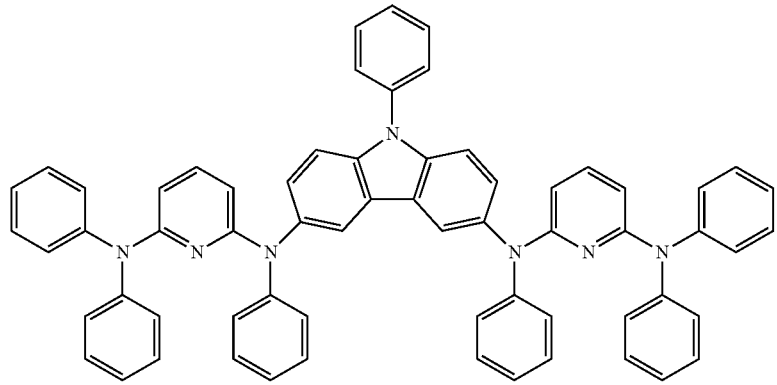

(99)

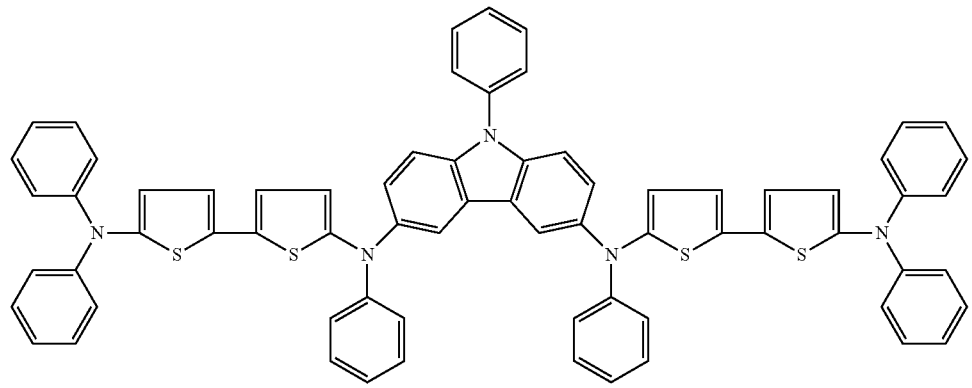

(100)

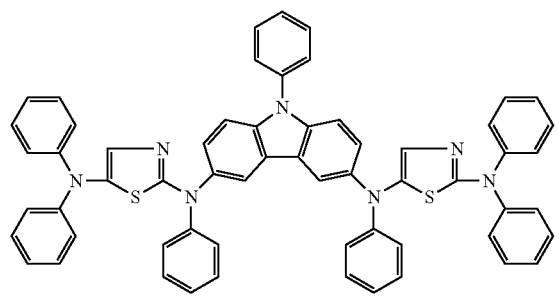

(101)

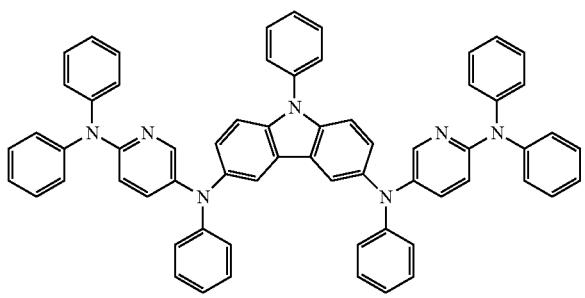

(102)

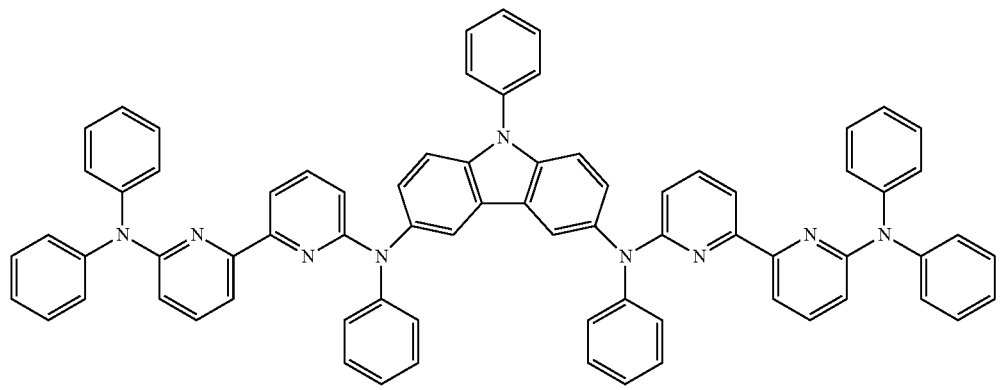

The carbazole derivatives represented by the structural formulas (25) to (38) are obtained when $R^2$ in the general formula (1) is hydrogen, and the carbazole derivatives represented by the structural formulas (39) to (52) are obtained when $R^2$ in the general formula (1) is the alkyl group.

The carbazole derivatives represented by the structural formulas (53) to (66) have structures in which the same substituents are combined with carbazole skeletons, and are easier to synthesize than the carbazole derivatives having structures in which different substituents are combined. Namely, when, $R^2$ has a structure of the general formula (2), and $Ar^1$ and $Ar^4$, $Ar^2$ and $Ar^5$, $Ar^3$ and $Ar^6$, and X and Y have identical structures, respectively, in the general formula (1), the same substituents may be combined with the carbazole skeletons. Therefore, the carbazole derivatives are easier to synthesize.

The carbazole derivative according to the present invention may have a halogen element as represented by the structural formulas (67) to (75).

The sites of substitution of X and Y in the general formulas (1) and (2) may be not only ortho positions as represented by the structural formulas (28), (42), and (56), but also meta positions as represented by the structural formulas (76) to (78). In addition, para positions may be employed.

The substituents of X and Y in the general formulas (1) and (2) may be heterocycles as represented by the structural formulas (79) to (102).

As a method for synthesizing the carbazole derivative according to the present invention, it is possible to apply various reactions. For example, a method shown in the following reaction scheme (A-1) can be cited. However, the method for synthesizing the carbazole derivative according to the present invention is not limited to this.

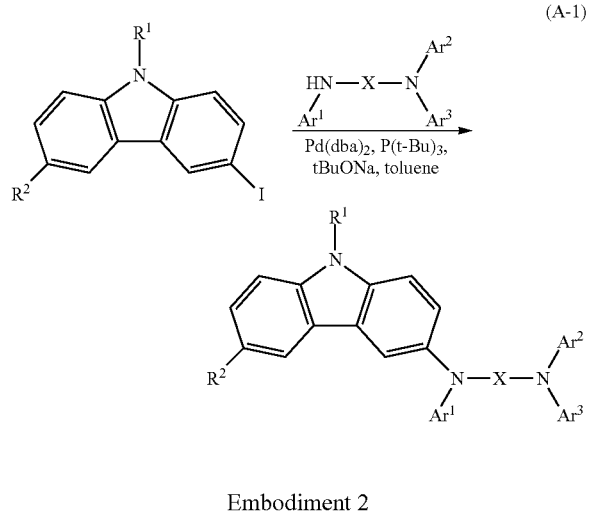

Embodiment 2

In the present embodiment, a light emitting element using the carbazole derivative shown in Embodiment 1 will be described.

A light emitting element according to the present invention has a structure in which a layer containing a light emitting material is interposed between a pair of electrodes. It is to be noted that the element structure is not particularly limited, and a known structures can be appropriately selected in accordance with the purpose.

FIG. 1 schematically shows an example of an element structure of a light emitting element according to the present invention. The light emitting element shown in FIG. 1 has a structure in which a layer containing a light emitting material 102 is provided between a first electrode 101 and a second electrode 103. In the present embodiment, the first electrode 101 functions as an anode, and the second electrode 103 functions as a cathode. A layer being in contact with the anode 104 in the layer containing the light emitting material 102 includes a carbazole derivative according to the present invention. It is to be noted that the anode in the present invention indicates an electrode which injects holes into the layer containing the light emitting material. In addition, the cathode in the present invention indicates an electrode which injects electrons into the layer containing the light emitting material.

For the anode, a known material can be used. It is preferable to use a metal, an alloy, an electrically conductive compound, a mixture thereof or the like which has a larger work function (specifically, 4.0 eV or more). Specifically, gold (Au), platinum (Pt), nickel (Ni), tungsten (W), chromium (Cr), molybdenum (Mo), iron (Fe), cobalt (Co), copper (Cu), palladium (Pd), and a nitride of a metal material (for example, titanium nitride: TiN), and the like can be used in addition to indium tin oxide (hereinafter, referred to as ITO), indium tin oxide containing silicon, and indium oxide containing 2% to 20% zinc oxide (ZnO).

On the other hand, for the cathode, a known material can be used. It is preferable to use a metal, an alloy, an electrically conductive compound, a mixture thereof, or the like which has a smaller work function (specifically, 3.8 eV or less). Specifically, a metal belonging to Group 1 or 2 of the periodic table of the elements, that is, an alkali metal such as lithium (Li) or cesium (Cs), an alkali-earth metal such as magnesium (Mg), calcium (Ca), or strontium (Sr), and an alloy (MgAg and AlLi) including the above-cited metal, a rare-earth metal such as europium (Eu) or ytterbium (Yb), an alloy including the rare-earth metal, and the like can be used. However, by using an electron injecting layer which has a high electron injecting property, a material having a higher work function, that is, a material that is normally used as the anode can also be used to form the cathode. For example, a metal conductive inorganic compound such as Al, Ag, or ITO can be used to form the cathode.

For the layer containing the light emitting material 102, known materials, and any of low molecular weight materials or polymer materials can be used. A material for forming the layer containing the light emitting material 102 may include not only a material including only an organic compound material but also a material partially including an inorganic compound. Further, the layer containing the light emitting material is formed by appropriately combining a hole injecting layer, a hole transporting layer, a hole blocking layer, a light emitting layer, an electron transporting layer, an electron injecting layer, and the like. The layer containing the light emitting material may be a single layer or have a stacked structure of a plurality of layers.

It is to be noted that it is preferable to use the carbazole derivative according to the present invention as a hole injecting material in the hole injecting layer since the carbazole derivative is excellent for the hole injecting property. The carbazole derivative according to the present invention is also excellent in the hole transporting property and, thus can be used as a hole transporting material. Specifically, the carbazole derivative according to the present invention can be used for a host transporting layer and a host material of a light emitting layer in the layer containing the light emitting material. In addition, the carbazole derivative according to the present invention can emit blue light or the like, and thus may be used as a light emitting material. Specifically, the carbazole derivative according to the present invention can be used as a guest material of the light emitting layer.

Here are specific materials to be used for a hole injecting layer, a hole transporting layer, a light emitting layer, an electron transporting layer, and an electron injecting layer.

As a hole injecting material forming a hole injecting layer, the carbazole derivative according to the present invention can be used. The carbazole derivative according to the present invention has an excellent hole injecting property. By using the carbazole derivative according to the present invention as a hole injecting material, it is possible to reduce the driving voltage of the light emitting element.

When the carbazole derivative according to the present invention is used for a hole transporting layer or a light emitting layer, a known material can be used as a hole injecting material forming a hole injecting layer. Specifically, a porphyrin-based compound is effective among organic compounds, and phthalocyanine (abbreviation: $H_2$-Pc), copper phthalocyanine (abbreviation: Cu-Pc), and the like can be used. In addition, a chemically doped polymer conductive compound can be used, such as polyethylene dioxythiophene (abbreviation: PEDOT) which is doped with polystyrene sulfonic acid (abbreviation: PSS), polyaniline (PAni), and the like. Further, as the hole injecting layer, an inorganic semiconductor film such as $VO_x$ and $MoO_x$, and an ultrathin film of an inorganic insulator such as $Al_2O_3$ are also effective.

An aromatic amine based compound (in other words, a compound having a benzene ring-nitrogen bond) is preferably used as a hole transporting material for forming the hole transporting layer. Examples of materials that are widely used include, for example, N,N'-bis(3-methylphenyl)-N,N'-diphenyl-[1,1'-biphenyl]-4,4'-diamine (hereinafter referred to as TPD), derivatives thereof such as 4,4'-bis[N-(1-naphthyl)-N- phenyl-amino]-biphenyl (hereinafter referred to as α-NPD), and star burst aromatic amine compounds such as 4,4',4"-tris (N-carbazolyl)-triphenylamine (hereinafter referred to as TCTA), 4,4',4"-tris(N,N-diphenyl-amino)-triphenylamine (hereinafter referred to as TDATA) and 4,4',4"-tris[N-(3-methylphenyl)-N-phenyl-amino]-triphenylamine (referred to as MTDATA).

In addition, the carbazole derivative according to the present invention is excellent in the hole transporting property, and thus can be used as a hole transporting material.

As a light emitting material forming the light emitting layer, specifically, various fluorescent pigments are effective in addition to metal complexes such as tris(8-quinolinolato) aluminum (hereinafter referred to as $Alq_3$), tris(4-methyl-8-quinolinolato)aluminum (hereinafter referred to as $Almq_3$), bis(10-hydroxybenzo[h]-quinolinolato)beryllium (hereinafter referred to as $BeBq_2$), bis(2-methyl-8-quinolinolato)-(4-hydroxy-biphenyl)-aluminum (hereinafter referred to as BAlq), bis[2-(2-hydroxyphenyl)-benzooxazolate]zinc (hereinafter referred to as $Zn(BOX)_2$), bis[2-(2-hydroxyphenyl)-benzothiazolate]zinc (hereinafter referred to as $Zn(BTZ)_2$).

When the light emitting layer is formed in combination with a guest material, as the guest material, triplet light emitting material materials (phosphorescence materials) such as bis(2-(2'-benzothienyl)pyridinato-$N,C^{3'}$)(acetylacetonate) iridium (abbreviation: $Ir(btp)_2(acac)$) can be used, in addition to singlet light emitting materials (luminescence materials) such as 4-(dicyanomethylene)-2-methyl-6-(p-dimethylaminostyryl)-4H-pyran (abbreviation: DCM1), 4-(dicyanomethylene)-2-methyl-6-(julolidine-4-yl-vinyl)-4H-pyran (abbreviation: DCM2), N,N-dimethylquinacridon (abbreviation: DMQd), 9,10-diphenylanthracene, 5,12-diphenyltetracene (abbreviation: DPT), coumarin 6, perylene, and rubrene.

The carbazole derivative according to the present invention is a light emitting material which can emit blue light and the like. Therefore, it is possible to use the carbazole derivative according to the present invention as a guest material of the light emitting layer. Although the case of emitting mainly blue light is described in the present embodiment, the carbazole derivative according to the present invention can provide luminescent color other than blue light. The light emitting element according to the present invention is not limited to the light emitting element that emits blue light.

In addition, the carbazole derivative according to the present invention is excellent in the hole transporting property, and thus can be used as a host material of the light emitting layer.

As an electron transporting material forming the electron transporting layer, the metal complexes mentioned above such as $Alq_3$, tris(4-methyl-8-quinolinolato)aluminum (abbreviation: $Almq_3$), bis(2-methyl-8-quinolinolato)-4-phenylphenolato-aluminum (abbreviation: BAlq), tris(8-quinolinolato)gallium (abbreviation: $Gaq_3$), bis(2-methyl-8-quinolinolato)-4-phenylphenolate-gallium (abbreviation: BGaq), bis(10-hydroxybenzo[h]-quinolinolato)beryllium (abbreviation: $BeBq_2$), bis[2-(2-hydroxyphenyl)-benzooxazolate]zinc (abbreviation: $Zn(BOX)_2$), and bis[2-(2-hydroxyphenyl)-benzothiazolate]zinc (abbreviation: $Zn(BTZ)_2$) can be used. Further, 2-(4-biphenylyl)-5-(4-tert-buthylphenyl)-1,3,4-oxadiazole (abbreviation: PBD), 1,3-bis[5-(p-tert-buthylphenyl)-1,3,4-oxadiazole-2-yl]benzene (abbreviation: OXD-7), 3-(4-tert-buthylphenyl)-4-phenyl-5-(4-biphenylyl)-1,2,4-triazole (abbreviation: TAZ), 3-(4-tert-buthylphenyl)-4-(4-ethylpheyl)-5-(4-biphenylyl)-1,2,4-triazole (abbreviation: p-EtTAZ), bathophenanthroline (abbreviation: BPhen), bathocuproin (abbreviation: BCP), and the like can be used in addition to the metal complex.

As an electron injecting material for the electron injecting layer, the electron transporting material mentioned above can be used. In addition, an ultrathin film of an insulator, for example, a halogenated alkali metal such as LiF or CsF, a halogenated alkali earth metal such as $CaF_2$, an alkali metal oxide such as $Li_2O$, or the like is often used. Alkali metal complexes such as lithium acetylacetonate (abbreviation: Li(acac)) and 8-quinolinolato-lithium (abbreviation: to Liq) are also effective. Furthermore, a layer in which the electron transporting material mentioned above and a metal having a smaller work function such as Mg, Li, and Cs are mixed can used as the electron injecting layer. In addition, a metal oxide such as molybdenum oxide (MoOx), vanadium oxide (VOx), ruthenium oxide (RuOx), and tungsten oxide (WOx), or one of a benzoxazole derivative and one or more of alkali metal, alkali earth metal, and transition metal may be included. Titanium oxide also may be used.

The carbazole derivative according to the present invention has a higher HOMO level. Thus, a barrier against the anode formed by a material having a larger work function is small, and holes are easy to inject. Therefore, by including the carbazole derivative according to the present invention in a layer being in contact with the anode, the driving voltage can be reduced.

In addition, the carbazole derivative according to the present invention also has a higher LUMO level. Thus, the electron injection barrier is higher, and it is thus possible to suppress penetration of electrons into the anode side. Accordingly, the probability of recombination of carriers is increased, and the luminous efficiency is thus improved. Namely, when the probability of recombination of the carriers is increased, less current is needed to obtain the same luminance.

Further, in addition, when lower voltage driving and lower current driving can be achieved, the advantage in that the light emitting element has longer lifetime and higher reliability can also be obtained.

Embodiment 3

In the present embodiment, a light emitting device which has the light emitting element using the carbazole derivative according to the present invention will be described.

In the present embodiment, a light emitting device which has the light emitting element according to the present invention in a pixel portion will be described with a reference to FIGS. 11A and B. FIG. 11A is a top view showing the light emitting device, and FIG. 11B is a cross sectional view along A-A' and B-B' in FIG. 11A. A portion 601 surrounded by a dotted line is a driving circuit portion (source side driving circuit), a portion 602 surrounded by another dotted line is a pixel portion, and a portion 603 surrounded by further another dotted line is a driving circuit portion (gate side driving circuit). In addition, a sealing substrate 604 and a sealing material 605 are provided. The inside surrounded by the sealing material 605 is an interspace 607.

A leading wiring 608 has a function of transmitting signals to be input to the source side driving circuit 601 and the gate side driving circuit 603, and receives signals such as a video signal, a clock signal, a start signal, and a reset signal from a FPC (Flexible Printed Circuit) 609 as an external input terminal. Although only the FPC is shown here, a printed wiring board (PWB) may be attached to the FPC. The light emitting device in the present specification includes not only the light emitting device itself but also a state in which the FPC or the PWB is attached thereto.

Next, a sectional structure will be described with reference to FIG. 11B. The driving circuit portion and the pixel portion are formed on an element substrate 610, however, the source side driving circuit 601 of the driving circuit portion and one pixel in the pixel portion 602 are shown here.

In the source side driving circuit 601, a CMOS circuit in which an n-channel TFT 623 and a p-channel TFT 624 are combined is formed. The TFT composing the driving circuit may be formed of a known CMOS circuit, PMOS circuit, or NMOS circuit. It is not always necessary to form the driving circuit on the substrate integrally as the present embodiment, and it is also possible to form the driving circuit not on the substrate but outside the substrate externally.

The pixel portion 602 includes plural pixels. Each of the pixels includes a switching TFT 611, a current controlling TFT 612, and a first electrode 613 electrically connected to a drain of the current controlling TFT 612. An insulator 614 is formed to cover an end portion of the first electrode 613. Here, a positive photosensitive acrylic resin film is used to form the insulator 614.

In addition, an upper or lower end portion of the insulator 614 is made to have a curved surface with a curvature in order to improve the coverage. For example, in the case of using positive photosensitive acrylic as a material of the insulator 614, it is preferable that only the upper end portion of the insulator 614 be made to have a curved surface with a curvature radius (0.2 µm to 3 µm). Besides, as the insulator 614, it is possible to use one of a negative photosensitive material which is insoluble in an etchant by irradiating light and a positive photosensitive material which is soluble in an etchant by irradiating light.

On the first electrode 613, a layer containing a light emitting material 616 and a second electrode 617 are formed. Here, it is preferable to use a material having a larger work function as a material to be used for the first electrode 613 which functions as an anode. For example, it is possible to use laminated structures such as a lamination layer of a titanium nitride film and a film containing aluminum as its main component, and a three-layer structure of a titanium nitride film, a film containing aluminum as its main component, and a titanium nitride film, and the like, in addition to single layers such as an ITO film, an indium tin oxide film containing silicon, an indium oxide film containing zinc oxide of 2% to 20%, a titanium nitride film, a chromium film, a tungsten film, a Zn film, and a Pt film. When a laminated structure is employed, it has a lower resistance as the wiring, favorable ohmic contact can be taken, and it is possible to function as an anode.

The layer containing the light emitting material 616 is formed by a known method such as an evaporation method with an evaporation mask, an inkjet method, and a spin coat method. The layer containing the light emitting material 616 contains the carbazole derivative according to the present invention. As a material used by being combined with the carbazole derivative according to the present invention, a low molecular weight material, an intermediate molecular weight material (including an oligomer and an dendrimer), or a polymer material may be used. In addition, as a material used for the layer containing the light emitting material, normally, an organic compound is often used as a single layer or a lamination layer. However, the present invention includes a structure in which an inorganic compound is used for a part of a film including an organic compound.

The carbazole derivative according to the present invention is excellent in the hole injecting property, and preferable to be used as a hole injecting material. In addition, the carbazole derivative according to the present invention is also excellent in the hole transporting property, and may be used as a hole transporting material.

As a material used for the second electrode (cathode) 617 formed on the layer containing the light emitting material 616, it is preferable to use a material having a smaller work function (Al, Mg, Li, Ca, an alloy or a compound thereof such as MgAg, MgIn, AlLi, $CaF_2$, LiF, and calcium nitride). When light which is generated in the layer containing the light emitting material 616 is transmitted through the second electrode 617, a lamination layer of a metal thin film with a thinned thickness and a transparent conductive film (ITO, indium oxide containing zinc oxide of 2% to 20%, indium tin oxide containing silicon, zinc oxide (ZnO), and the like) may be used as the second electrode (cathode) 617.

The sealing substrate 604 and the element substrate are bonded with the sealing material 605 to have a structure where a light emitting element 618 is provided in the interspace 607 surrounded by an element structure 610, the sealing substrate 604, and the sealing material 605. The interspace 607 is filled with a filler. There is a case in that the sealing material 605 is filled in the interspace 607 in addition to the case in that inert gas (nitrogen, argon, or the like) is filled.

It is to be noted that it is preferable to use an epoxy resin for the sealing material 605. A material which allows permeation of moisture and oxygen as little as possible is desirable. Further, as a material used for the sealing substrate 604, a plastic substrate including a material such as FRP (Fiberglass-Reinforced Plastics), PVF (polyvinyl fluoride), Mylar, polyester, or acrylic can be used in addition to a glass substrate and a quartz substrate.

As mentioned above, the light emitting device which has the light emitting element according to the present invention can be obtained.

The light emitting device according to the present invention has the carbazole derivative excellent in the hole injecting and hole transporting properties. Therefore, the diving voltage can be reduced.

The carbazole derivative according to the present invention has a high electron injection barrier, and it is possible to suppress penetration of electrons into the anode side. Thus, the probability of recombination of carriers is increased, and the luminous efficiency is improved. Namely, when the probability of recombination of carriers is increased, less current is needed to obtain the same luminance.

In addition, when lower voltage driving and lower current driving can be achieved, the advantage in that the light emitting element has longer lifetime and higher reliability can be obtained.

Since the lower voltage driving and the lower current driving are possible, lower power consumption can be realized.

Example 1

As an example of a carbazole derivative according to the present invention, a synthesis method of 3-[n-(4-diphenylaminophenyl)-N-phenylamino]-9-phenylcarbazole (abbreviation: PCzDPA1) represented by a structural formula (28) will be described.

(28)

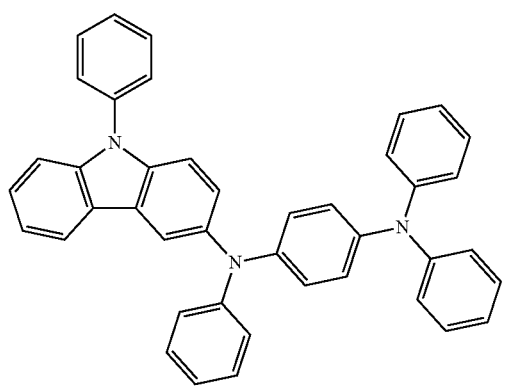

(A-3)

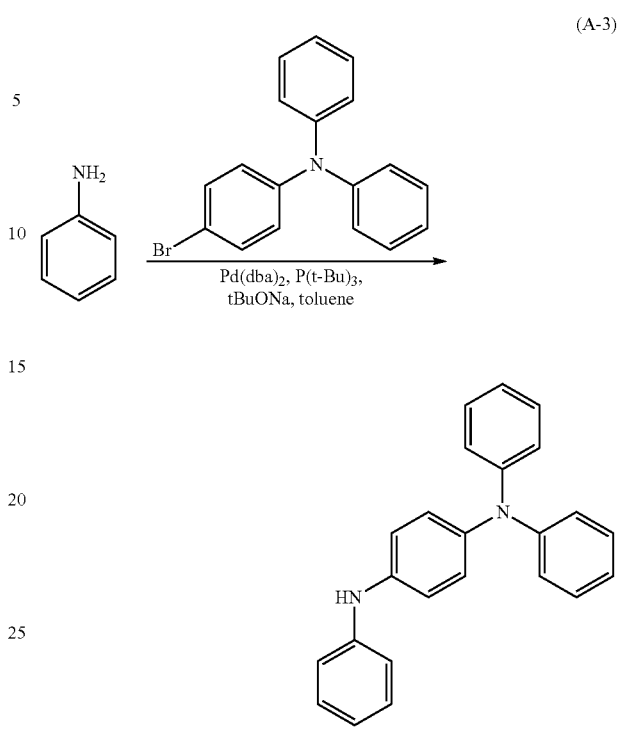

[Step 1]

First, a synthesis method of 4-brmotriphenylamine will be described. A synthesizing scheme of 4-brmotriphenylamine is shown in (A-2).

(A-2)

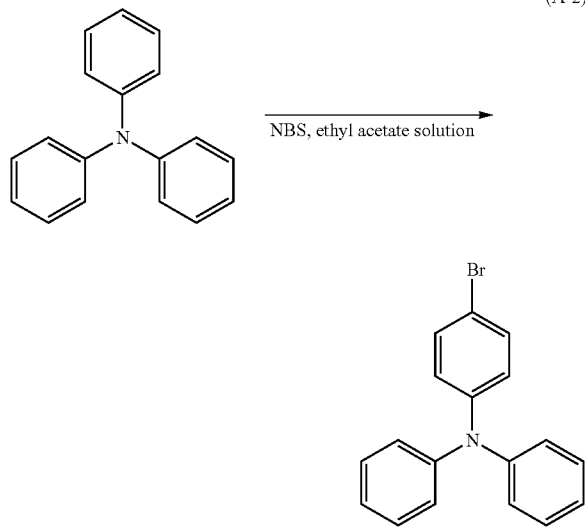

35.6 g (200 mmol) of N-bromosuccinimide (NBS) was added into 1.5 L of ethyl acetate solution of 54.0 g (220 mmol) of triphenylamine, and stirred overnight. Then, the solution was concentrated to 1 L, and washed with 1 L of 5% sodium acetate solution. After washing, the solution was further concentrated to approximately 50 mL, and 46.5 g of white powder in a yield of 73% was obtained as precipitation by adding methanol.

[Step 2]

Next, a synthesis method of N-(4-diphenylaminophenyl)-N-phenylamine will be described. A synthesizing scheme of N-(4-diphenylaminophenyl)-N-phenylamine is shown in (A-3).

A three-necked flask was charged with 559 mg (6 mmol) of 4-bromotriphenylamine, 345 mg (0.6 mmol) of dibenzylidineacetonepalladium (0), and 577 mg (6 mmol) of sodium tert-butoxide and the atmosphere in the flask was replaced by nitrogen. After that, 5 ml of dehydrated toluene was added to the flask including these, and degassing was carried out for about 3 minutes till air bubbles were not generated. 559 mg (6 mmol) of aniline, 0.37 ml (1.8 mmol) of tri-tert-buthylphosphine (10% hexane solution) were added thereto, and stirring was carried out at 80° C. for 5 hours in an atmosphere of nitrogen. Then, it was confirmed by thin film chromatography (TLC) that 4-bromotriphenylamine as a material was almost gone. A saturated aqueous solution of sodium chloride was added to finish the reaction, and a toluene layer and a water layer were obtained. The water layer was extracted with about 100 ml of ethyl acetate, and this ethyl acetate layer and the toluene layer were mixed. Magnesium sulfate was added to this mixed solution to remove moisture, and then, the magnesium sulfate was removed by filtration. After concentrating this filtrate, an object was purified by silica gel column using a solvent of ethyl acetate and hexane in a ratio of 1:20. After purifying, further condensation was carried out, hexane was added, and the object was precipitated by using an ultra sonic washing machine. When the precipitation appeared, a condensation and a precipitation were carried out again and 700 mg of cream powder was obtained in a yield of 42%.

[Step 3]

A synthesis method of 3-iodine-9-phenylcarbazole will be described. A synthesizing scheme of N-phenyl-3-iodinecarbazole is shown in (A-4).

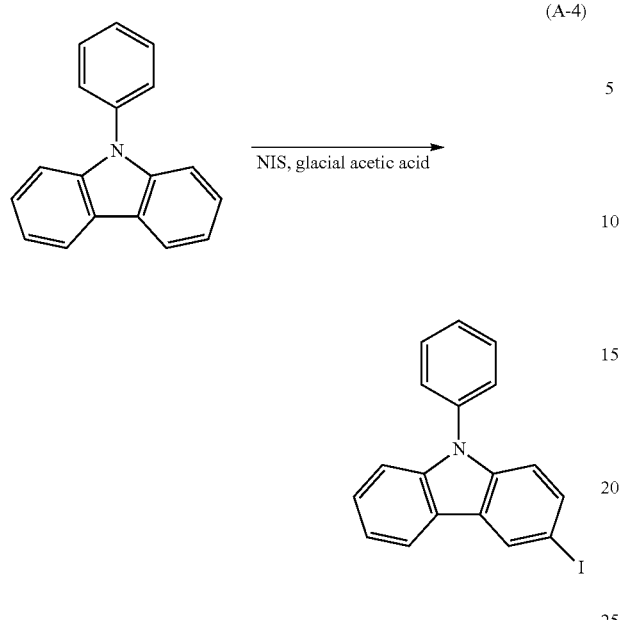

(A-4)

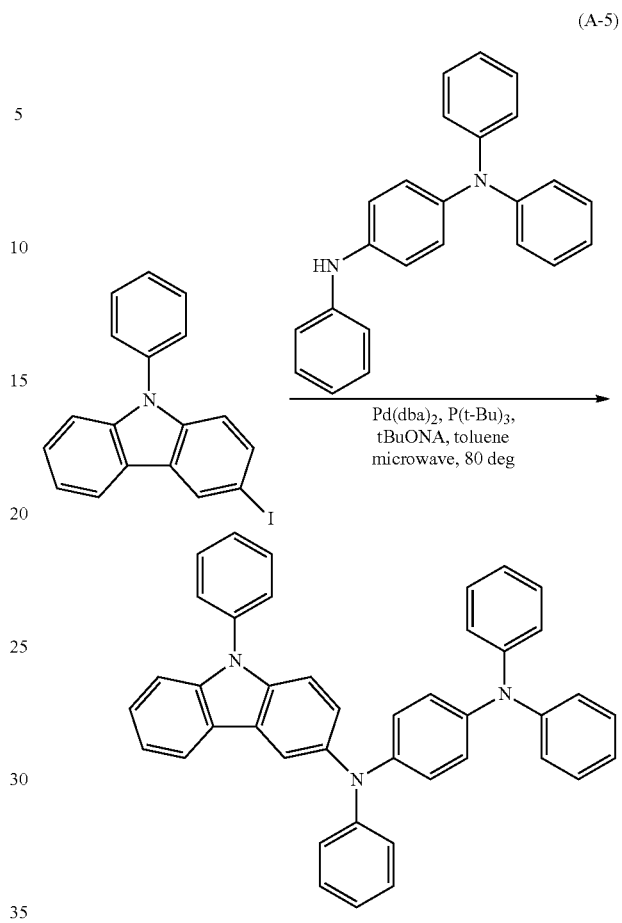

(A-5)

4.9 g (20 mmol) of N-phenylcarbazole was dissolved in 100 ml of glacial acetic acid, 4.48 g (20 mmol) of N-iodine-succinimide was gradually added thereto, and then stirring was carried out at a room temperature overnight. The solution became clouded at 2.5 hours from the reaction started, and was suspended by a light orange precipitate at 3.5 hours from the reaction started. This suspension was dropped to 300 ml of the saturated aqueous solution of sodium chloride to obtain a light salmon pink block object. After washing this block object three times with water, 200 ml of ethyl acetate was added to dissolve the block object, and washing was carried out with sodium hydrogen carbonate and then with water. After magnesium sulfate was added to remove moisture, magnesium sulfate was removed by filtration. Recrystallization was carried out to obtain 5 g of white powder in a yield of 68% by heating this solution to which hexane was added.

Alternatively, 3-iodine-9-phenylcarbazole also can be synthesized by the following method. 24.3 g (100 mmol) of N-phenylcarbazole was dissolved in 600 ml of glacial acetic acid, 22.5 g (100 mmol) of N-iodinesuccinimide was gradually added thereto, and stirring was carried out at a room temperature overnight. The solution became clouded at 2.5 hours from the reaction started, and was suspended by a light orange precipitate at 3.5 hours from the reaction started. This suspension was filtered. The filtrated object was washed with sodium hydrogen carbonate, then with water. Finally, the filtrated was washed with methanol to obtain 24.7 g of white powder in a yield of 67%.

[Step 4]

A synthesis method of 3-[N-(4-diphenylaminophenyl)-N-phenylamino]-9-phenylcarbazole (abbreviation: PCzDPA1) will be described. A synthesizing scheme of PCzDPA1 is shown in (A-5).

Figure 13:
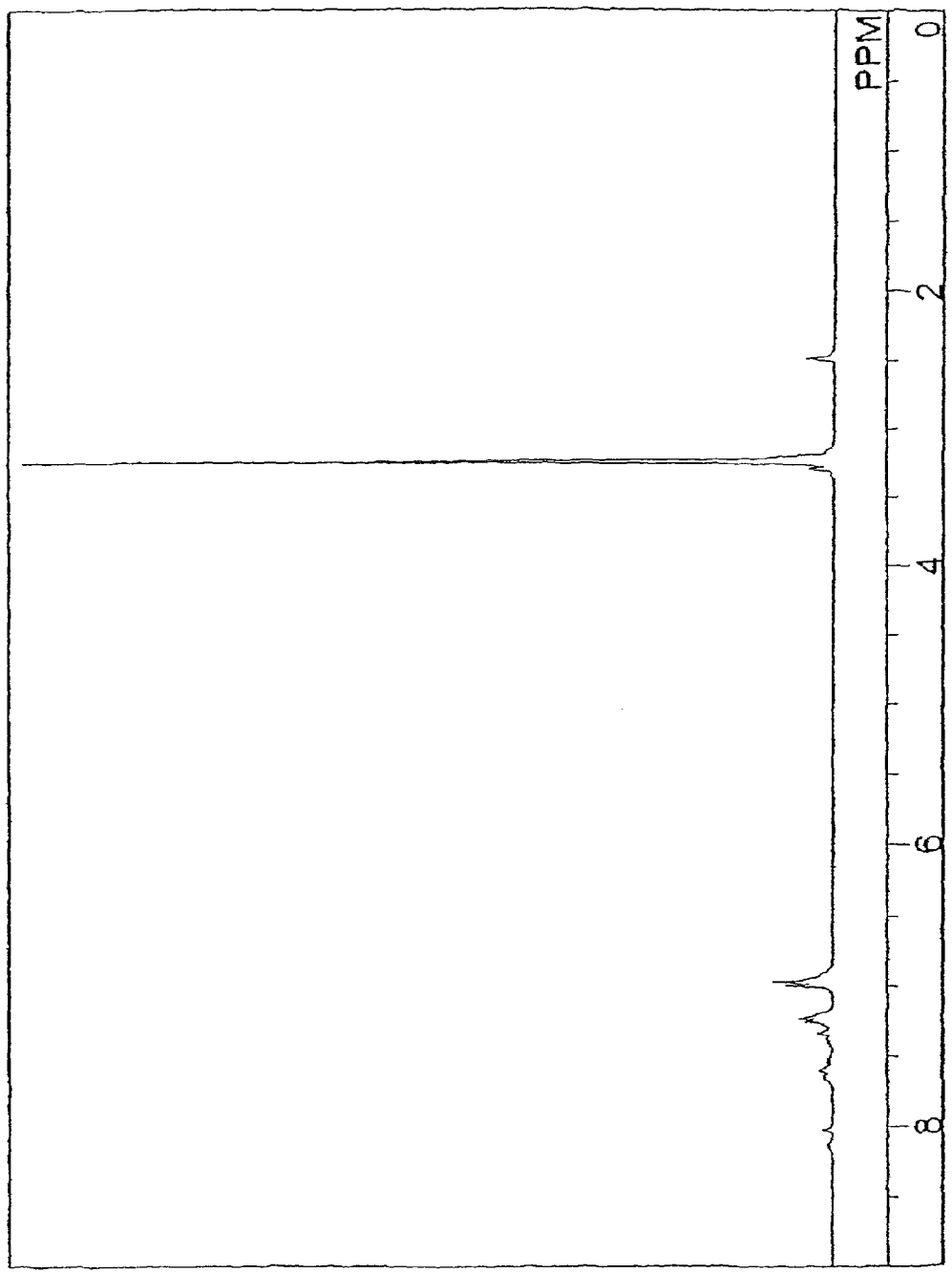
FIG. 13 is a chart of $^1$H NMR of 3-[N-(4-diphenylaminophenyl)-N-phenylamino]-9-phenylcarbazole which is a carbazole derivative according to the present invention.
Figure 14:
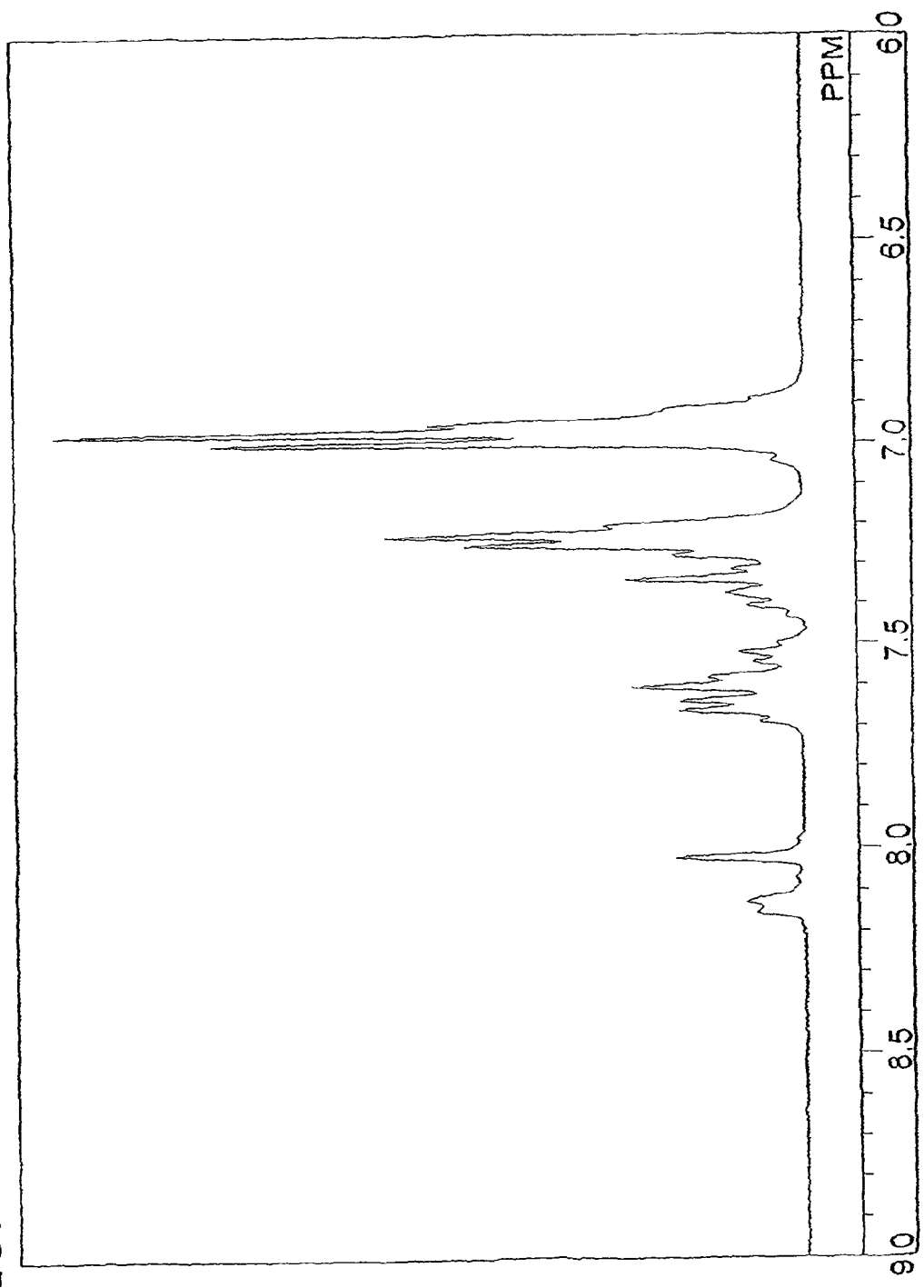
FIG. 14 is a chart of $^1$H NMR of 3-[N-(4-diphenylaminophenyl)-N-phenylamino]-9-phenylcarbazole which is a carbazole derivative according to the present invention.

627.64 mg (1.7 mmol) of 3-iodine-9-phenylcarbazole, 672.86 mg (2.0 mmol) of N-(4-diphenylaminophenyl)-N-phenylamine, 57.5 mg (0.1 mmol) of dibenzylideneacetone-palladium, and 335 mg (3.5 mmol) of sodium tert-butoxide were put into a three-necked flask, and the atmosphere in the flask was replaced by nitrogen. 3.5 ml of dehydrated toluene was added thereto and degassing was carried out for 3 minutes. After adding 0.4 ml of tri-tert-butylphosphine (10 w % hexane solution), the flask was shaked lightly up and down to stir the content. The solution was heated and stirred at 80° C. for 10 minutes with irradiating by a microwave at 200 W. After the reaction, saturated aqueous solution of sodium chloride was added, and the extraction with 100 ml of ethyl acetate was carried out. Further, magnesium sulfate was added to remove moisture, and then, magnesium sulfate was removed by filtration. Filtrate was condensed and purified by silica gel column using a solution of ethyl acetate and hexane in a ratio of 1:1. Hexane was added to the purified solution, and recrystallization was carried out to obtain 650 mg of cream powder in a yield of 65%. The NMR data are indicated below. $^1$H NMR (300 MHz, DMSO-d); δ=6.89-7.05 (m, 13H), 7.21-7.28 (m, 9H), 7.32-7.43 (m, 3H), 7.50-7.69 (m, 5H), 8.02 (s, 1H), 8.14 (d, j=7.2, 1H). In addition, FIG. 13 shows a chart of $^1$H NMR, and FIG. 14 shows an enlarged view of the portion of 6.0 to 9.0 ppm in FIG. 13.

Thermogravimetry-differential thermal analysis (TG-DTA) of the obtained PCzDPA1 was carried out. A thermogravimetric/differential thermal analyzer (manufactured by Seiko Instruments Inc., TG/DTA-320) was used for the measurement, and thermophysical property of the obtained PCzDPA1 was evaluated at a programming rate of 10° C./min in an atmosphere of nitrogen. As a result, temperature at which the weight was reduced to be 95% or less of the weight at the beginning of the measurement under normal pressure was 375° C. from a relation between weight and temperature (thermogravimetric analysis).

In addition, melting point was observed at from 185° C. to 186° C. in a measurement using a melting point apparatus (manufactured by As One Corporation, ATM-01).

Figure 3:
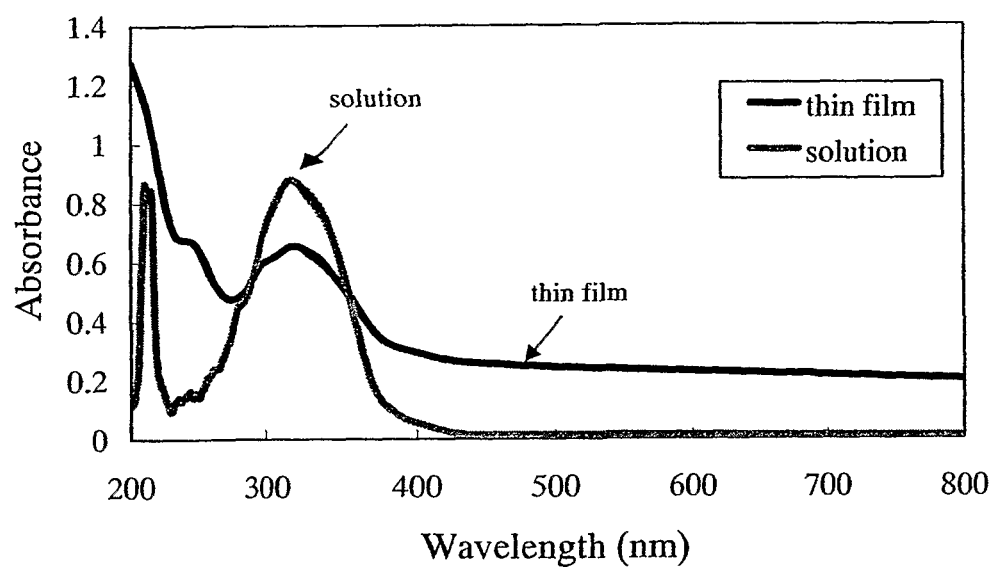
FIG. 3 is a diagram showing an absorption spectrum of 3-[N-(4-diphenylaminophenyl)-N-phenylamino]-9-phenylcarbazol which is a carbazol derivative according to the present invention.
Figure 4:
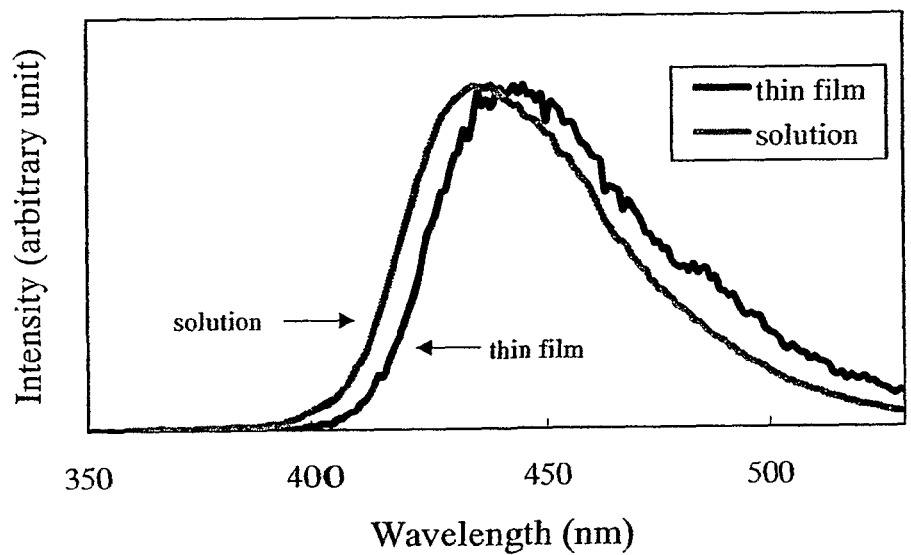
FIG. 4 is a diagram showing an emission spectrum of 3-[N-(4-diphenylaminophenyl)-N-phenylamino]-9-phenylcarbazole which is a carbazole derivative according to the present invention.

Absorption spectra of the toluene solution of PCzDPA1 and a thin film of PCzDPA1 are shown in FIG. 3. An UV/VIS spectrophotometer (manufactured by JASCO Corporation, V-550) was used for the measurement. In FIG. 3, a horizontal axis indicates wavelength (nm) and a vertical axis indicates absorbance. The largest absorption wavelength was 318 nm in the case of the toluene solution, and 321 nm in the case of the thin film. Emission spectra of the toluene solution (excitation wavelength 330 nm) of PCzDPA1 and the thin film (excitation wavelength 321 nm) of PCzDPA1 are shown in FIG. 4. In FIG. 4, a horizontal axis indicates wavelength (nm) and a vertical axis indicates emission intensity (arbitrary unit). The highest emission wavelength was 445 nm (excitation wavelength 330 nm) in the case of the toluene solution, and 445 nm (excitation wavelength 321 nm) in the case of the thin film.

Further, the HOMO level and LUMO level of PCzDPA1 in a state of a thin film was measured. A value of the HOMO level was obtained by converting a value of ionization potential measured by a photoelectron spectrometer (manufactured by Riken Keiki Co., Ltd., AC-2) into a negative value. A value of the LUMO level was obtained by using absorption edge of the thin film in FIG. 3 as an energy gap and adding the value of the absorption edge to the value of the HOMO level. As a result, the HOMO level and the LUMO level were −5.16 eV and −2.01 eV, respectively.

In the present example, the method of synthesizing 3-[N-(4-diphenylaminophenyl)-N-phenylamino]-9-phenylcarbazole (abbreviation: PCzDPA1) with the use of 3-iodine-9-phenylcarbazole is described. However, PCzDPA1 can be synthesized when 3-bromo-9-phenylcarbazole is used. A material for 3-bromo-9-phenylcarbazole is cheaper than that of 3-iodine-9-phenylcarbazole. On the other hand, 3-iodine-9-phenylcarbazole can make reaction time shorter than 3-bromo-9-phenylcarbazole, and make the reaction proceed even when the catalyst amount is reduced to about 1/10.

Example 2

As an example of a carbazole derivative according to the present invention, a synthesis example of 3,6-bis[N-(4-diphenylaminophenyl)-N-phenylamino]-9-phenylcarbazole (abbreviation: PCzDPA2) represented by the structural formula (56) will be described.

[Step 1]

A synthesis method of 3,6-diiodo-9-phenylcarbazole is described. A synthesis scheme of 3,6-diiodo-9-phenylcarbazole is shown in (A-6).

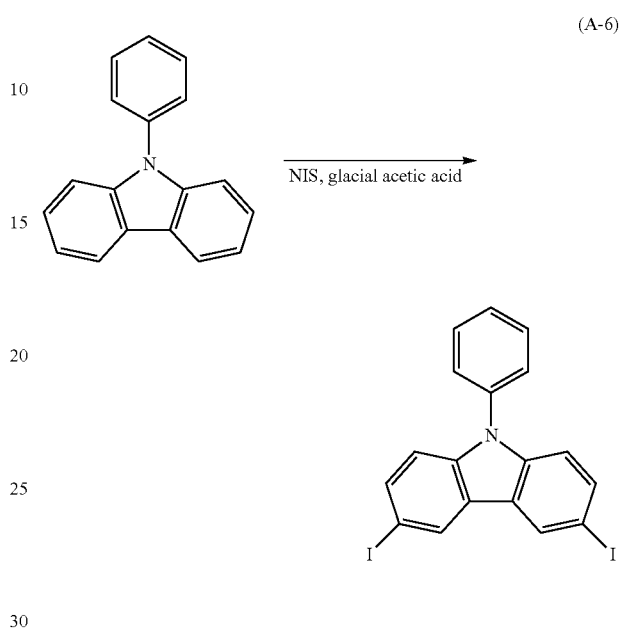

(A-6)

24.3 g (100 mmol) of N-phenylcarbazole was dissolved in 700 ml of glacial acetic acid, 44.9 g (200 mmol) of N-iodine-succinimide was gradually added thereto, and then stirring was carried out at a room temperature overnight. The solution became clouded at 2.5 hours from the reaction started, and precipitation started at 3.5 hours from the reaction started. The obtained precipitate was filtered and was suspended in the aqueous solution of sodium hydrogencarbonate to be neutralized. The solution was filtered. And the obtained material was washed with water and dried to obtain 47 g of off-white powder in a yield of 95%.

[Step 2]

A synthesis method of 3,6-bis[N-(4-diphenylaminophenyl)-N-phenylamino]-9-phenylcarbazole (abbreviation: PCzDPA2) is described. A synthesis scheme of PCzDPA2 is shown in (A-7).

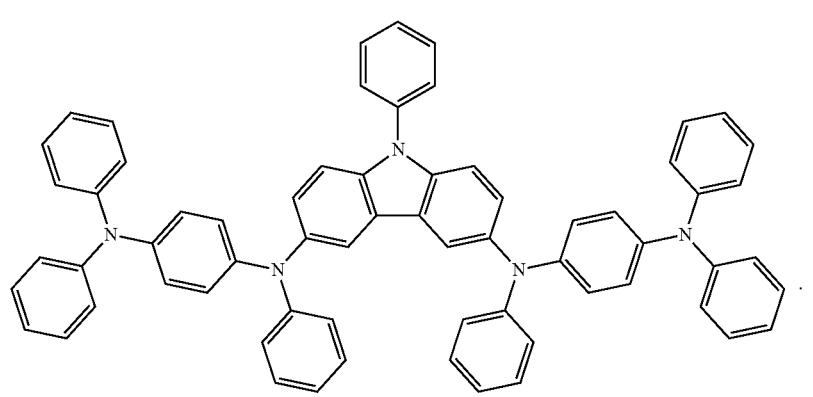

(56)

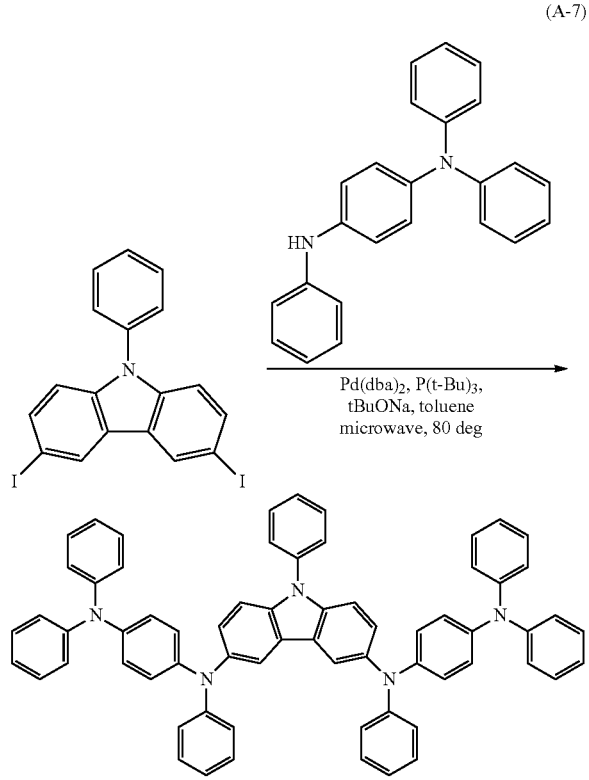

(A-7)

Figure 15:
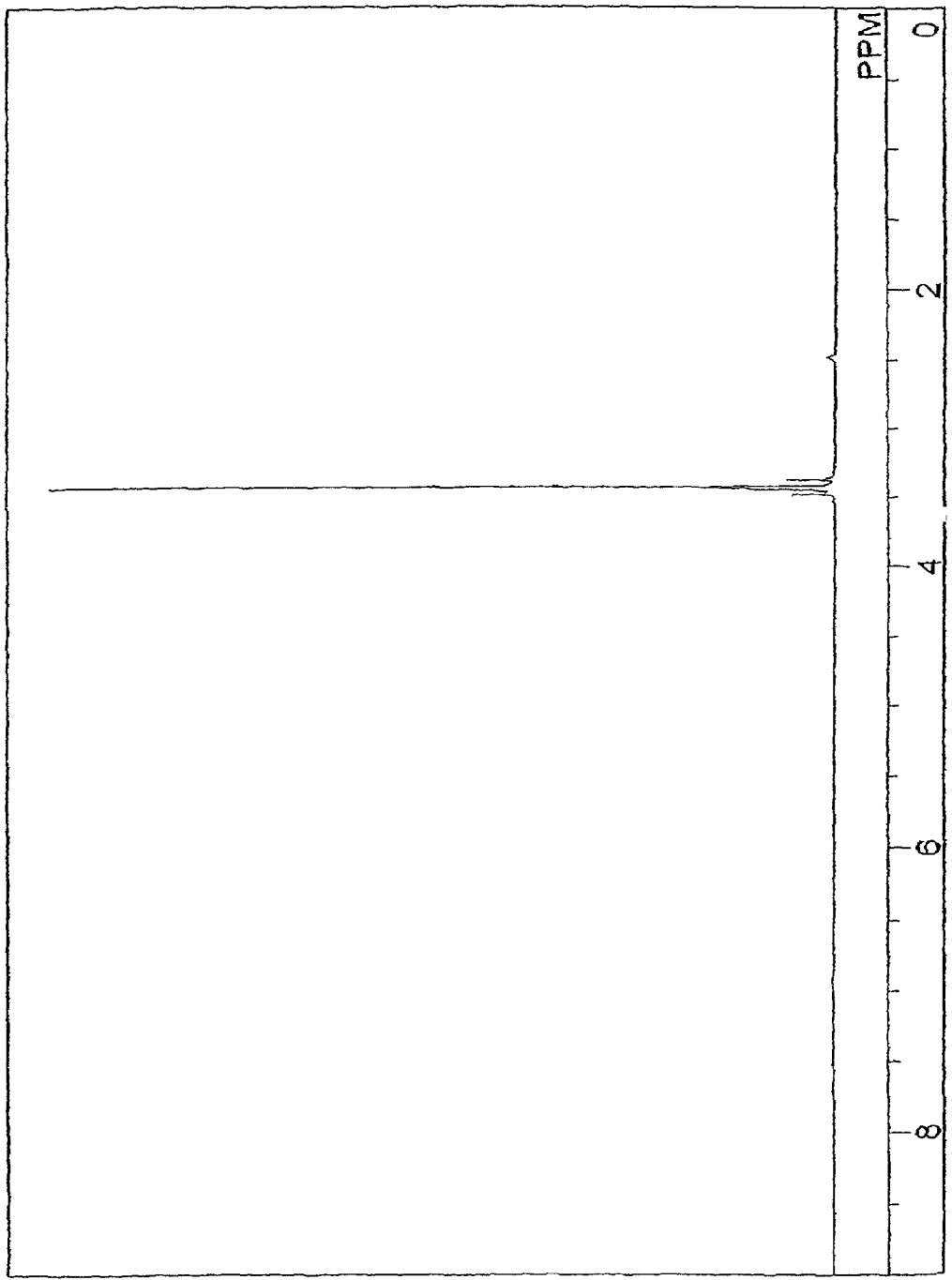
FIG. 15 is a chart of $^1$H NMR of 3,6-bis[N-(4-diphenylaminophenyl)-N-phenylamino]-9-phenylcarbazole which is a carbazole derivative according to the present invention.
Figure 16:
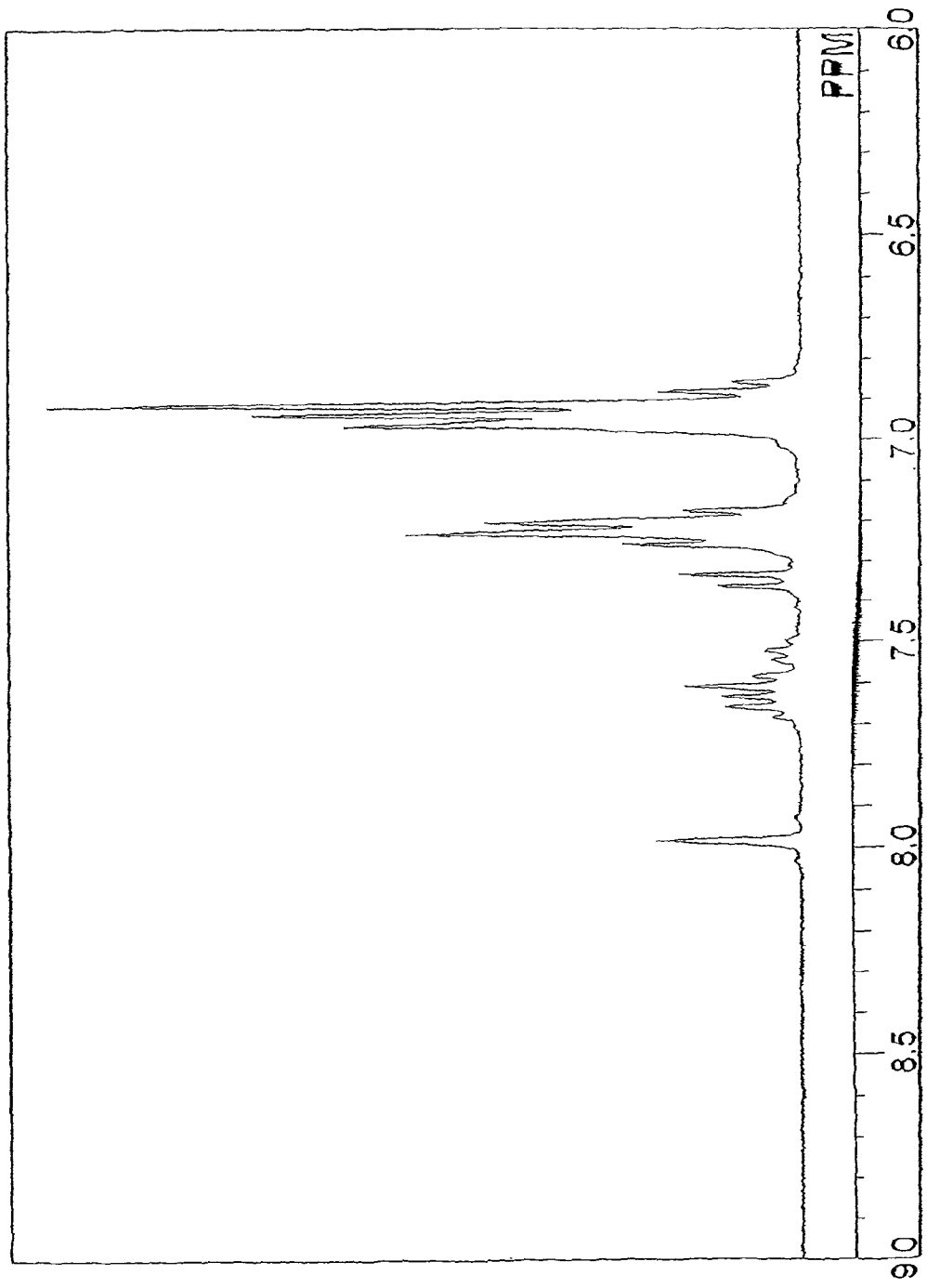
FIG. 16 is a chart of $^1$H NMR of 3,6-bis[N-(4-diphenylaminophenyl)-N-phenylamino]-9-phenylcarbazole which is a carbazole derivative according to the present invention.

A three-necked flask was charged with 5.44 g (11 mmol) of 3,6-diiodo-9-phenylcarbazole, 9 g (27 mmol) of N-(4-diphenylaminophenyl)-N-phenylamine, 500 mg (0.87 mmol) of dibenzylideneacetonepalladium, and 3.35 g (35 mmol) of sodium tert-butoxide and the atmosphere in the flask was replaced by nitrogen. 100 ml of dehydrated toluene was added thereto and degassing was carried out for 3 minutes. After adding 4 ml of tri-tert-butylphosphine (10 w % hexane solution), the solution was stirred for 16 hours at 80° C. in an atmosphere of nitrogen. After the reaction, a saturated aqueous solution of sodium chloride was added and the solution was extracted with 200 ml of ethyl acetate. Magnesium sulfate was added thereto to remove moisture. Then, the solution was filtered to remove magnesium sulfate. The filtrate was condensed and was added by drops to a solution of ethyl acetate and hexane in a ratio of 1:10 to be suspended. Supernatant liquid of the suspension was collected. Then the collected supernatant liquid was purified by silica gel column with the solvent of ethyl acetate and hexane in a ratio of 1:10 and was condensed to obtain cream-colored powder. Insoluble constituent of the suspension was purified using solvent of toluene and hexane in a ratio of 5:1 by a silica gel column to obtain cream-colored powder. Thus obtained cream-colored powder is the object and was 6.5 g in a yield of 75% in total. The NMR data of the object are indicated below.
$^1$H NMR (300 MHz, DMSO-d); δ=6.86-6.97 (m, 26H), 7.18-7.36 (m, 14H), 7.35 (d, j=9.0, 2H), 7.52-7.66 (m 5H), 7.99 (s, 2H). FIG. 15 shows a chart of $^1$H NMR and FIG. 16 shows an enlarged view of the portion from 6.0 to 9.0 ppm in FIG. 15.

Thermogravimetry-differential thermal analysis (TG-DTA) of the obtained PCzDPA2 was carried out. The thermogravimetric/differential thermal analyzer (manufactured by Seiko Instruments Electronics Inc., TG/DTA 320) was used for the measurement. A thermophysical property of the obtained PCzDPA2 was evaluated at a programming rate of 10° C./min in an atmosphere of nitrogen. From the relation between weight and temperature (thermogravimetric analysis), the temperature at which the weight was reduced to be 95% or less of the weight at the beginning of the measurement under normal pressure was 460° C.

The melting point was observed at from 173 to 181° C. in a measurement using a melting point apparatus (manufactured by As One Corporation, ATM-01).

Figure 5:
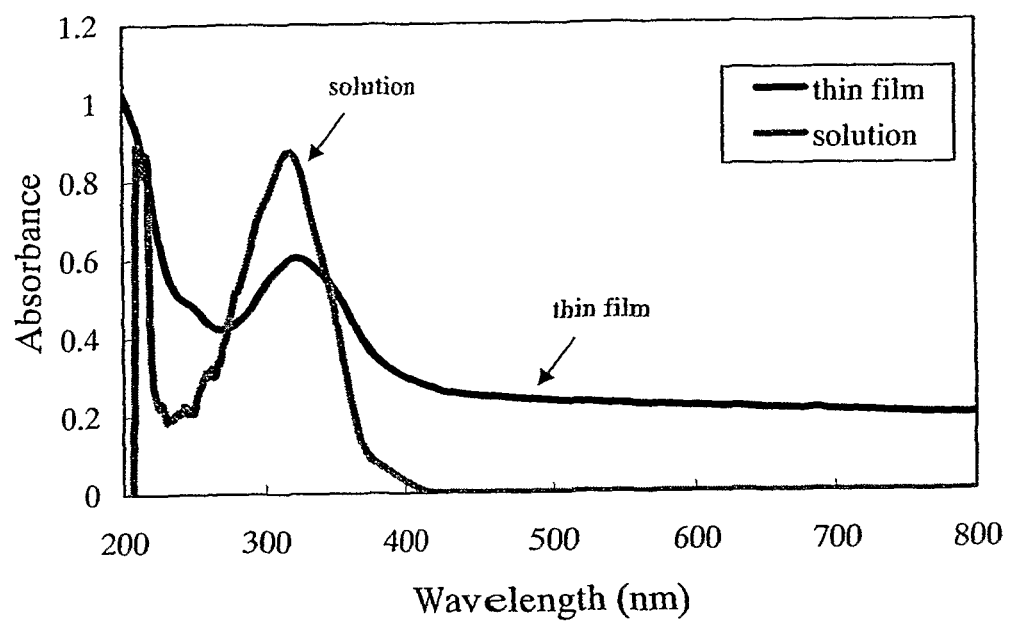
FIG. 5 is a diagram showing an absorption spectrum of 3,6-bis[N-(4-diphenylaminophenyl)-N-phenylamino]-9-phenylcarbazole which is a carbazole derivative according to the present invention.
Figure 6:
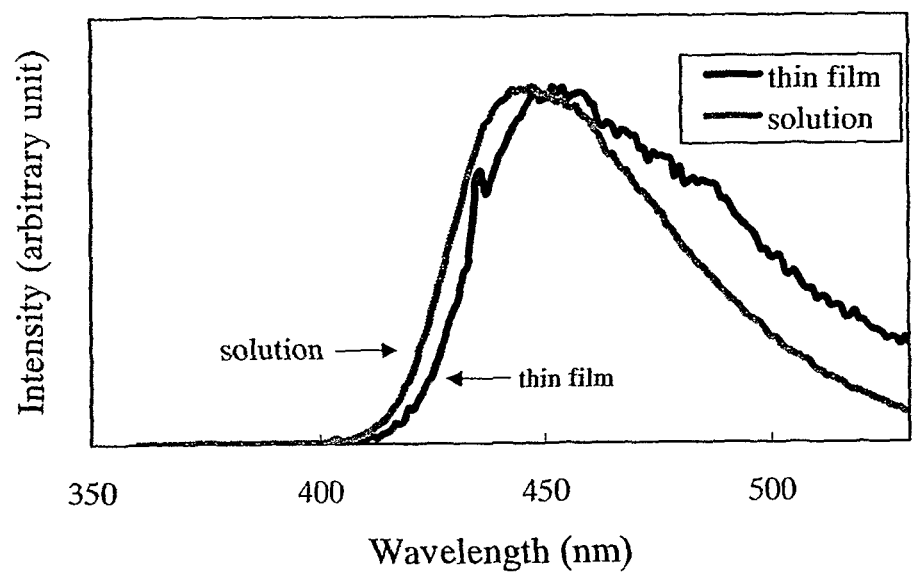
FIG. 6 is a diagram showing an emission spectrum of 3,6-bis[N-(4-diphenylaminophenyl)-N-phenylamino]-9-phenylcarbazole which is a carbazole derivative according to the present invention.

Absorption spectra of the toluene solution of PCzDPA2 and a thin film of PCzDPA2 are shown in FIG. 5. The UV/VIS spectrometer (manufactured by JASCO Corporation, V-550) was used for the measurement. In FIG. 5, a horizontal axis shows wavelength (nm) and a vertical axis shows absorbance. The largest absorption wavelength was 318 nm in the case of the toluene solution and the largest absorption wavelength was 323 nm in the case of the thin film. Emission spectra of the toluene solution of PCzDPA2 (excitation wavelength of 335 nm) and the thin film of PCzDPA2 (excitation wavelength of 323 nm) are shown in FIG. 6. In FIG. 6, a horizontal axis shows wavelength (nm) and a vertical axis shows emission intensity (arbitrary unit). The highest emission wavelength was 445 nm (excitation wavelength of 335 nm) in the case of the toluene solution and the highest emission wavelength was 452 nm (excitation wavelength of 323 nm) in the case of the thin film.

Measurement of HOMO level and LUMO level of PCzDPA2 in the state of a thin film was carried out. A value of the HOMO level was obtained by converting a value of ionization potential measured by the photoelectron spectrometer (manufactured by Riken Keiki Co., Ltd., AC-2) into a negative value. On the other hand, a value of the LUMO level was obtained by using the value of absorption edge of the thin film in FIG. 5 as an energy gap to be added to the value of the HOMO level. As a result, the HOMO level and the LUMO level were −5.16 eV and −2.16 eV, respectively.

Example 3

Figure 2:
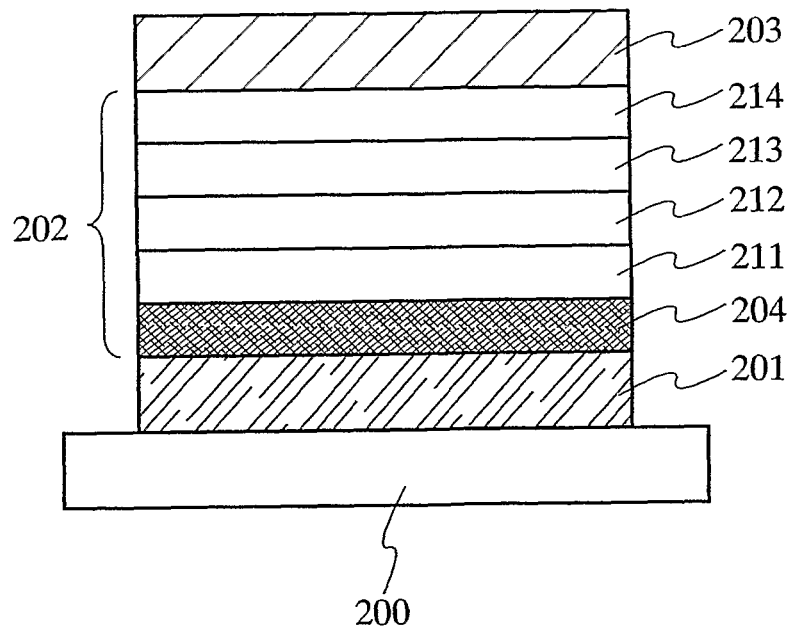
FIG. 2 is an explanatory view of a light-emitting element according to the present invention.

In this example, a light emitting element having a carbazole derivative PCzDPA1 represented by the structural formula (28) and synthesized in Example 1 will be described with reference to FIG. 2.

A first electrode 201 of the light emitting element was formed over a substrate 200. In this example, the first electrode functions as an anode. The anode was formed by a sputtering method using indium tin oxide containing silicon oxide which is a material for a transparent conductive film to have a thickness of 110 nm.

Then, a layer containing a light emitting material 202 was formed over the first electrode 201. In this example, the layer containing the light emitting material 202 was formed by stacking a hole injecting layer 204, a hole transporting layer 211, a light emitting layer 212, an electron transporting layer 213, and an electron injecting layer 214.

The substrate provided with the first electrode 201 was fixed in a substrate holder in a commercially available vacuum vapor deposition equipment so that the surface provided with the first electrode 201 faces downward. The carbazole derivative according to the present invention was provided to a deposition source in the vacuum vapor deposition equipment to form the hole injecting layer 204 by a vapor deposition method with a resistance heating method to have a thickness of 50 nm. As a material for forming the hole injecting layer 204, PCzDPA1 represented by the structural formula (28) was used in this example.

Then, the hole transporting layer 211 was formed with a material which is excellent in a hole transporting property. As a material for the hole transporting layer 211, a known hole transporting material can be used. In this example, the hole transporting layer 211 was formed by the same method as that of the hole injecting layer 204 using α-NPD to have a thickness of 10 nm.

The light emitting layer 212 was formed. In the light emitting layer 212, holes and electrons recombine with each other and emit light. In this example, a host material of $Alq_3$ and a guest material of coumarin 6 were co-evaporated to form the light emitting layer 212 to have a thickness of 40 nm including coumarin 6 in $Alq_3$ at 1 wt %.

The electron transporting layer 213 was formed. As a material for the electron transporting layer 213, a known electron transporting material can be used. In this example, the electron transporting layer was formed by a vapor deposition method using $Alq_3$ to have a thickness of 30 nm.

Thereafter, the electron injecting layer 214 was formed. As the electron injecting layer 214, a known electron injecting material can be used. In this example, the electron injecting layer was formed by a vapor deposition method using calcium fluoride to have a thickness of 1 nm.

After the layer containing the light emitting material 202 was formed by stacking the hole injecting layer 204, the hole transporting layer 211, the light emitting layer 212, the electron transporting layer 213, and the electron injecting layer 214, a second electrode 203 was formed by a sputtering method or a vapor deposition method. In this example, the second electrode functions as a cathode. In this example, the second electrode was formed by a vapor deposition method using Al to have a thickness of 200 nm.

Thus, a light emitting element of this example was formed.

In the light emitting element of this example, a hole injection barrier can be reduced since a layer being in contact with the anode includes the carbazole derivative which is excellent in the hole injecting property. Consequently, the driving voltage is reduced and a light emitting element with improved reliability can be provided.

Example 4

In this example, a light emitting element having a carbazol carbazole derivative PCzDPA2 represented by the structural formula (56) will be described.

Like Example 3, an anode was formed by indium tin oxide containing silicon oxide to have a thickness of 110 nm, a hole injecting layer was formed by a carbazol carbazole derivative PCzDPA2 according to the present invention represented by the structural formula (56) to have a thickness of 50 nm, a hole transporting layer was formed by α-NPD to have a thickness of 10 nm, and a light emitting layer was formed by $Alq_3$ and coumarin 6 to have a thickness of 40 nm including coumarin 6 in $Alq_3$ at 1 wt % over a substrate. Then, an electron transporting layer was formed by $Alq_3$ to have a thickness of 30 nm, an electron injecting layer was formed by calcium fluoride to have a thickness of 1 nm, and a cathode was formed by Al to have a thickness of 200 nm.

Thus, a light emitting element of this example was formed.

Comparative Example 1

As a comparative example, a light emitting element was formed using 4,4'-bis(N-{4-[N,N-bis(3-methylphenyl)amino]phenyl}-N-phenylamino)biphenyl (abbreviation: DNTPD) for a hole injecting layer.

Like Example 3, an anode was formed by indium tin oxide containing silicon oxide to have a thickness of 110 nm, a hole injecting layer was formed by DNTPD to have a thickness of 50 nm, a hole transporting layer was formed by α-NPD to have a thickness of 10 nm, and a light emitting layer was formed by $Alq_3$ and coumarin 6 to have a thickness of 40 nm including coumarin 6 in $Alq_3$ at 1 wt % over a substrate. Then, an electron transporting layer was formed by $Alq_3$ to have a thickness of 30 nm, an electron injecting layer was formed by calcium fluoride to have a thickness of 1 nm, and a cathode was formed by Al to have a thickness of 200 nm.

Figure 7:
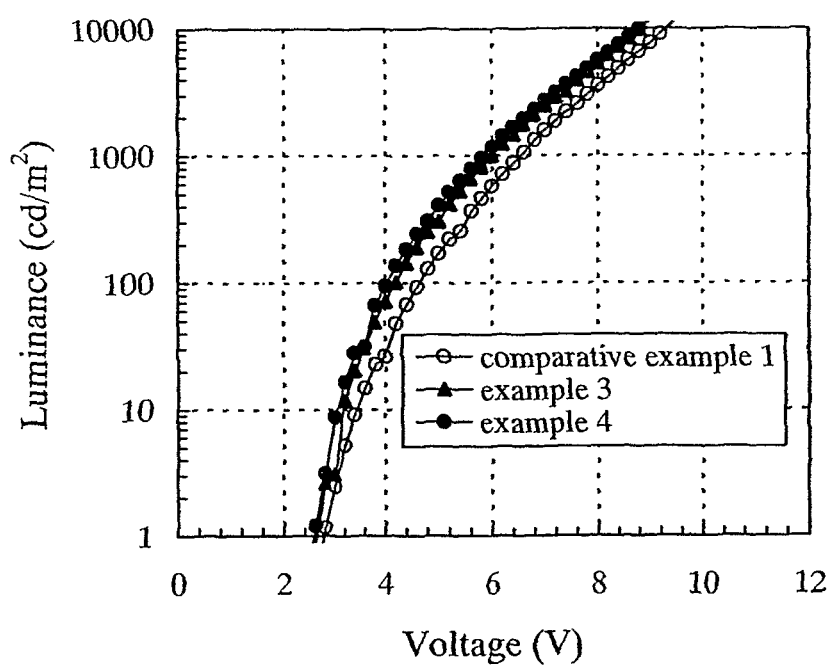
FIG. 7 is a diagram showing luminance-voltage characteristics of light emitting elements manufactured in Example 3, Example 4, and Comparative Example 1.
Figure 8:
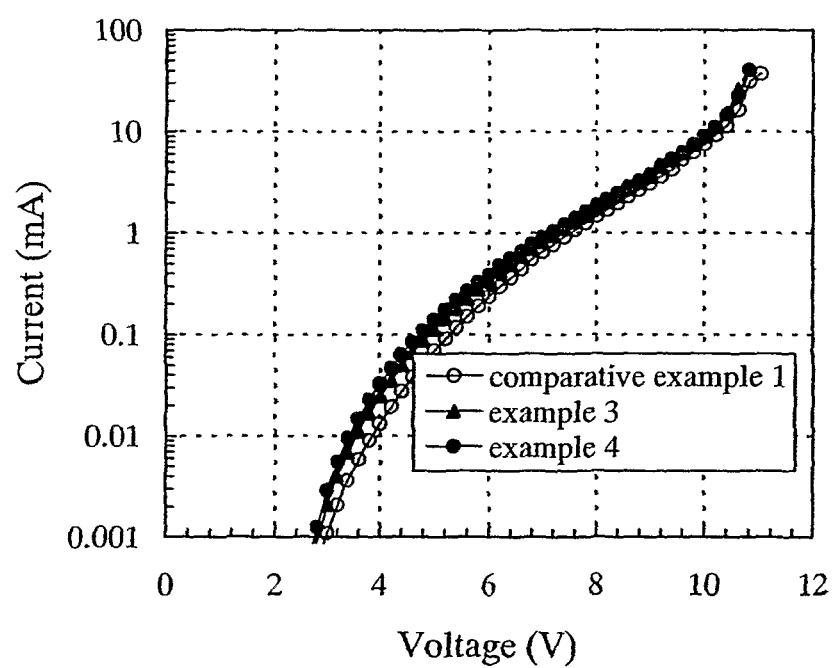
FIG. 8 is a diagram showing current-voltage characteristics of a light emitting elements manufactured in Example 3, Example 4, and Comparative Example 1.

FIG. 7 shows luminance-voltage characteristics and FIG. 8 shows current-voltage characteristics of the light emitting elements manufactured in Example 3, Example 4, and Comparative Example 1.

According to FIGS. 7 and 8, it can be said that a driving voltage for obtaining light emission at the certain luminance from a light emitting element having the carbazole derivative according to the present invention can be reduced. Specifically, voltage required for luminance of 1000 $cd/m^2$ was 6.0 V in the case of the light emitting element manufactured in Example 3 and an electric current density at this time was 8.5 $mA/cm^2$. Similarly, voltage required for luminance of 1000 $cd/m^2$ was 5.8 V in the case of the light emitting element manufactured in Example 4 and an electric current density at this time was 8.2 $mA/cm^2$. In the case of the light emitting element manufactured in Comparative Example 1, a required voltage was 6.6 V and an electric current density at this time was 11.0 $mA/cm^2$. That is, low voltage driving and low current driving can be realized by using the carbazol carbazole derivative according to the present invention for a light emitting element.

Figure 9:
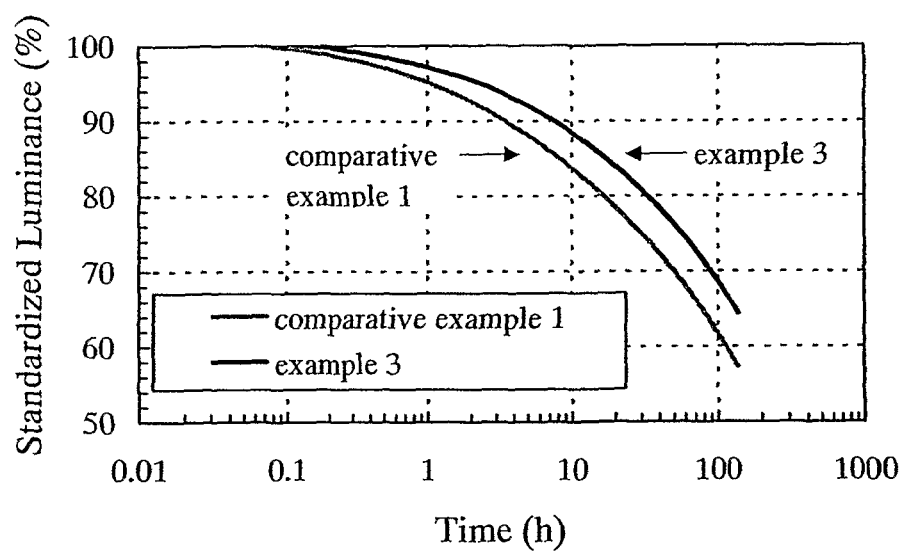
FIG. 9 is a diagram showing changes in standardized luminance over time of a light emitting elements manufactured in Example 3 and Comparative Example 1.
Figure 10:
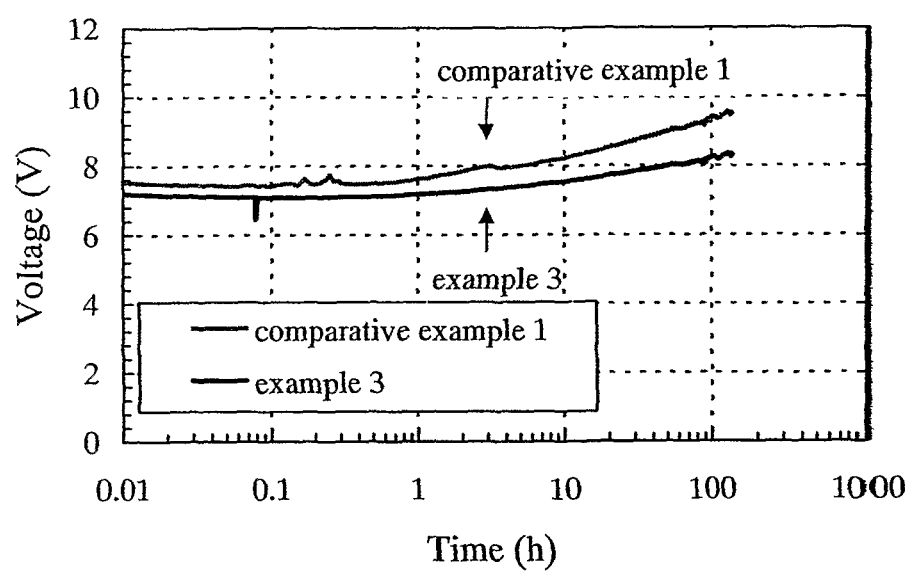
FIG. 10 is a diagram showing changes of voltage over time of a light emitting elements manufactured in Example 3 and Comparative Example 1.

FIG. 9 shows changes in standardized luminance over time and FIG. 10 shows changes in voltage over time of the light emitting elements manufactured in Example 3 and Comparative Example 1. As a measuring method, the initial luminance was set at 3000 $cd/m^2$ and the change in the luminance over time and the change in the voltage over time were measured while a constant current being supplied.

According to FIG. 9, the luminance of the light emitting element manufactured in Example 3 was not reduced over time as much as that of the light emitting element manufactured in Comparative Example 1. Further, according to FIG. 10, in the light emitting element manufactured in Example 3, the voltage hardly increased over time. Therefore, the light emitting element having the carbazole derivative according to the present invention has a long life time and improved reliability.

As shown in Example 1 and Example 2, HOMO level of PCzDPA1 represented by the structural formula (28) was −5.16 eV and HOMO level of PCzDPA2 represented by the structural formula (56) was −5.16 eV. On the other hand, HOMO level of DNTPD shown in Comparative Example was −5.15 eV which was approximately same as that of PCzDPA1 and PCzDPA2 as measured by the same method. Consequently, the carbazole derivative according to the present invention has an approximately same hole injecting property as that of DNTPD. Therefore, a hole injection barrier against the anode can be reduced, and so the driving voltage can be reduced.

Further, a result of the measurement shows that a driving voltage of the light emitting element having the carbazole derivative according to the present invention can be lower than that of the light emitting element having DNTPD. It is because that the carbazole derivative according to the present invention is superior to the DNTPD in terms of the hole transporting property. As the hole transporting property of the layer is improved, carriers can be easily moved in the layer containing the light emitting material. Therefore a driving voltage of the light emitting element having the carbazole derivative can be lowered than that of the light emitting element having DNTPD.

Further, a life of the light emitting element according to the present invention is longer than that of the light emitting element having DNTPD. The carbazole derivative according to the present invention has high LUMO level, and a high electron injection barrier. That leads to prevent electrons from going into an anode side. Therefore, the probability of recombination of carriers becomes high and luminous efficiency is improved. That is, current required to realize light emission at the certain luminance is lowered, and so a low current driving can be realized.

The reliability is also improved since a low voltage and low current driving can be realized. As the result of the actual measurement shown in FIGS. 9 and 10, the light emitting elements manufactured in Example 3 and Example 4 have longer lives and are improved reliabilities than those of the light emitting element manufactured in Comparative Example 1.

Example 5

In this example, a light emitting element having a carbazole derivative according to the present invention as a hole injecting material and as a hole transporting material will be described.

Like Example 3, an anode is formed by indium tin oxide containing silicon oxide to have a thickness of 110 nm.

A layer which functions as both of a hole injecting layer and a hole transporting layer is formed by the carbazole derivative PCzDPA1 according to the present invention represented by the structural formula (28) to have a thickness of 60 nm, and a light emitting layer is formed by $Alq_3$ and coumarin 6 to have a thickness of 40 nm including coumarin 6 in $Alq_3$ at 1 wt %. Then an electron transporting layer is formed by $Alq_3$ to have a thickness of 30 nm, an electron injecting layer is formed by calcium fluoride to have a thickness of 1 nm, and a cathode is formed by Al to have a thickness of 200 nm.

Thus, the light emitting element of this example is formed.

In the light emitting element according to the present invention, a hole injection barrier against the anode can be reduced since a layer being in contact with the anode includes a carbazole derivative which is excellent in a hole injecting property. Consequently, the driving voltage can be reduced.

Since the carbazole derivative according to the present invention is excellent in the hole transporting property, a driving voltage can be further lowered by using the carbazole derivative for a hole transporting layer of the light emitting element. The carbazole derivative according to the present invention has an effect of preventing electron from going into an anode side. Therefore, the probability of recombination of carriers becomes high and luminous efficiency is improved. As a result, a light emitting element with improved reliability can be realized.

Example 6

In this example, various kinds of electrical apparatuses including the light emitting device manufactured by using the light emitting element according to the present invention as their parts will be described.

As the electrical apparatus manufactured by using the light emitting device having the light emitting element according to the present invention, a camera such as a video camera and a digital camera, a goggle type display, a navigation system, a sound reproduction device (such as an in-car audio system or an audio set), a personal computer, a game machine, a portable information terminal (a mobile computer, a portable telephone, a portable game machine, an electronic book or the like), an image reproduction device equipped with a recording medium (specifically, a device equipped with a display device, which can reproduce a recording medium such as a Digital Versatile Disc (DVD) and display the image), and the like can be given. FIGS. 12A to 12E show specific examples of these electronic appliances.

Figure 12A:
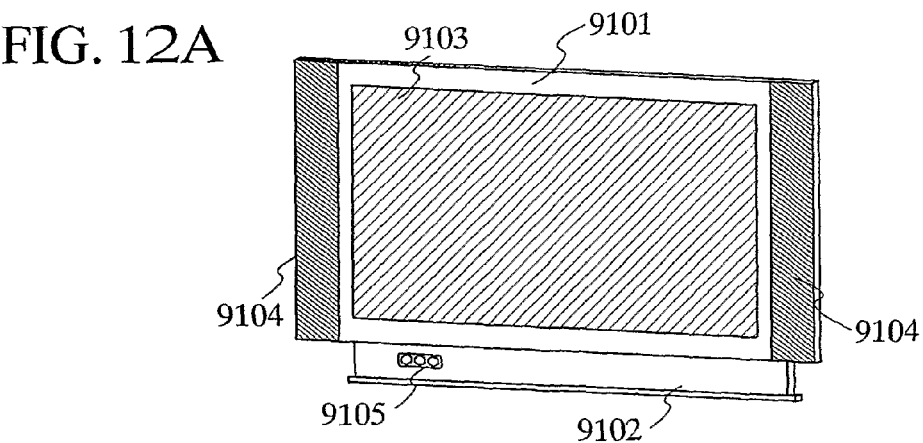
FIGS. 12A to 12E are explanatory views of electronic appliances.

FIG. 12A shows a television receiver including a housing 9101, a support base 9102, a display portion 9103, a speaker portion 9104, a video input terminal 9105, and the like. A light emitting device having a light emitting element according to the present invention is used for the display portion 9103 to manufacture the television receiver. The television receiver includes all devices for displaying information such as for a personal computer, for receiving TV broad casting, and for displaying an advertisement.

Figure 12B:
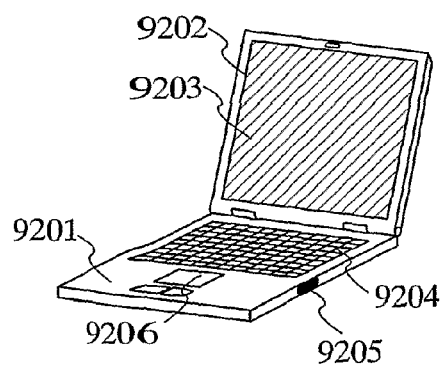

FIG. 12B shows a personal computer including a main body 9201, a housing 9202, a display portion 9203, a keyboard 9204, an external connection port 9205, a pointing mouse 9206, and the like. A light emitting device having a light emitting element according to the present invention is used for the display portion 9203.

Figure 12C:
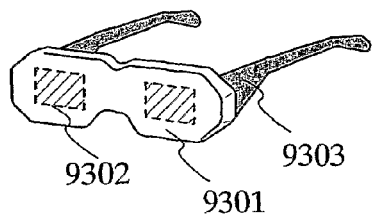

FIG. 12C shows a goggle type display including a main body 9301, a display portion 9302, and an arm portion 9303 and the like. A light emitting device having a light emitting element according to the present invention is used for the display portion 9302.

Figure 12D:
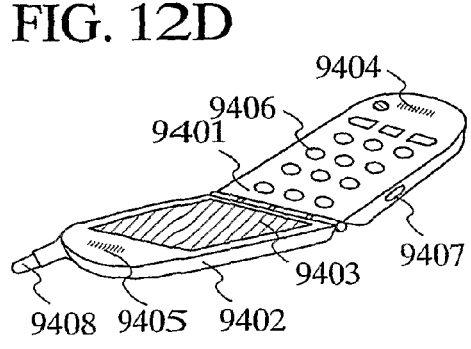

FIG. 12D shows a portable telephone including a main body 9401, a housing 9402, a display portion 9403, an audio input portion 9404, an audio output portion 9405, an operation key 9406, an external connecting port 9407, an antenna 9408, and the like. A light emitting device having a light emitting element according to the present invention is used for the display portion 9403. Power consumption of the portable telephone can be suppressed by displaying white text on the black background in the display portion 9403.

Figure 12E:
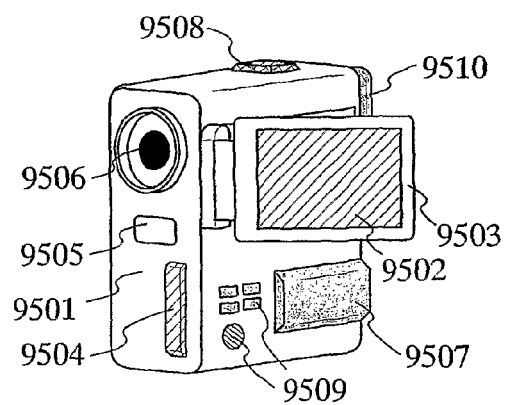

FIG. 12E shows a camera including a main body 9501, a display portion 9502, a housing 9503, an external connecting port 9504, a remote control receiving portion 9505, an image receiving portion 9506, a battery 9507, an audio input portion 9508, operation keys 9509, an eye piece portion 9510, and the like. A light emitting device having a light emitting element according the present invention is used for the display portion 9502.

As described above, the applicable range of a light emitting device formed according to the invention is extremely wide and the light emitting device can be applied to various fields of electrical apparatus. By using the light emitting device having the light emitting element according to the present invention, electrical apparatus which has a long life and low power consumption can be provided.

Example 7

As an example of the carbazole derivative according to the present invention, a synthesis example of the 3-[N-(4-diphenylaminophenyl)-N-(1-naphthyl)amino]-9-phenylcarbazole (abbreviation: PCzDPN1) represented by the structural formula (33) will be described.

(33)

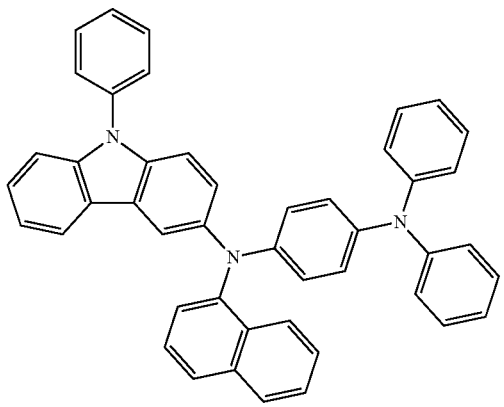

[Step 1]
A synthesis method of N-(4-diphenylaminophenyl)-N-(1-naphthyl)amine is described. A synthesis scheme of N-(4-diphenylaminophenyl)-N-(1-naphthyl)amine is shown in (A-8).

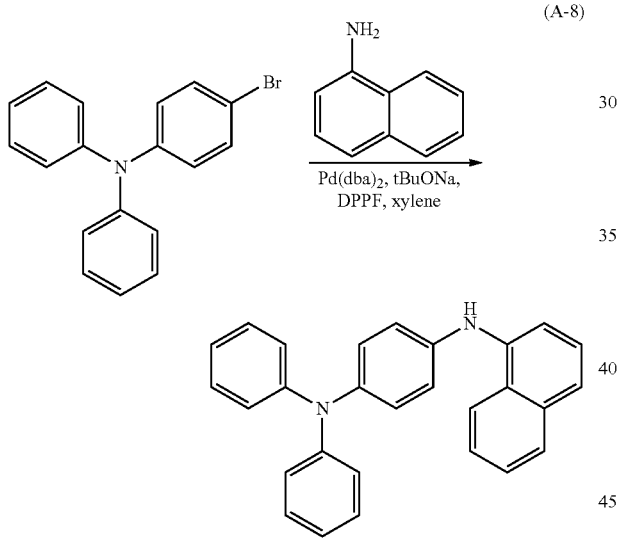

(A-8)

Figure 21:
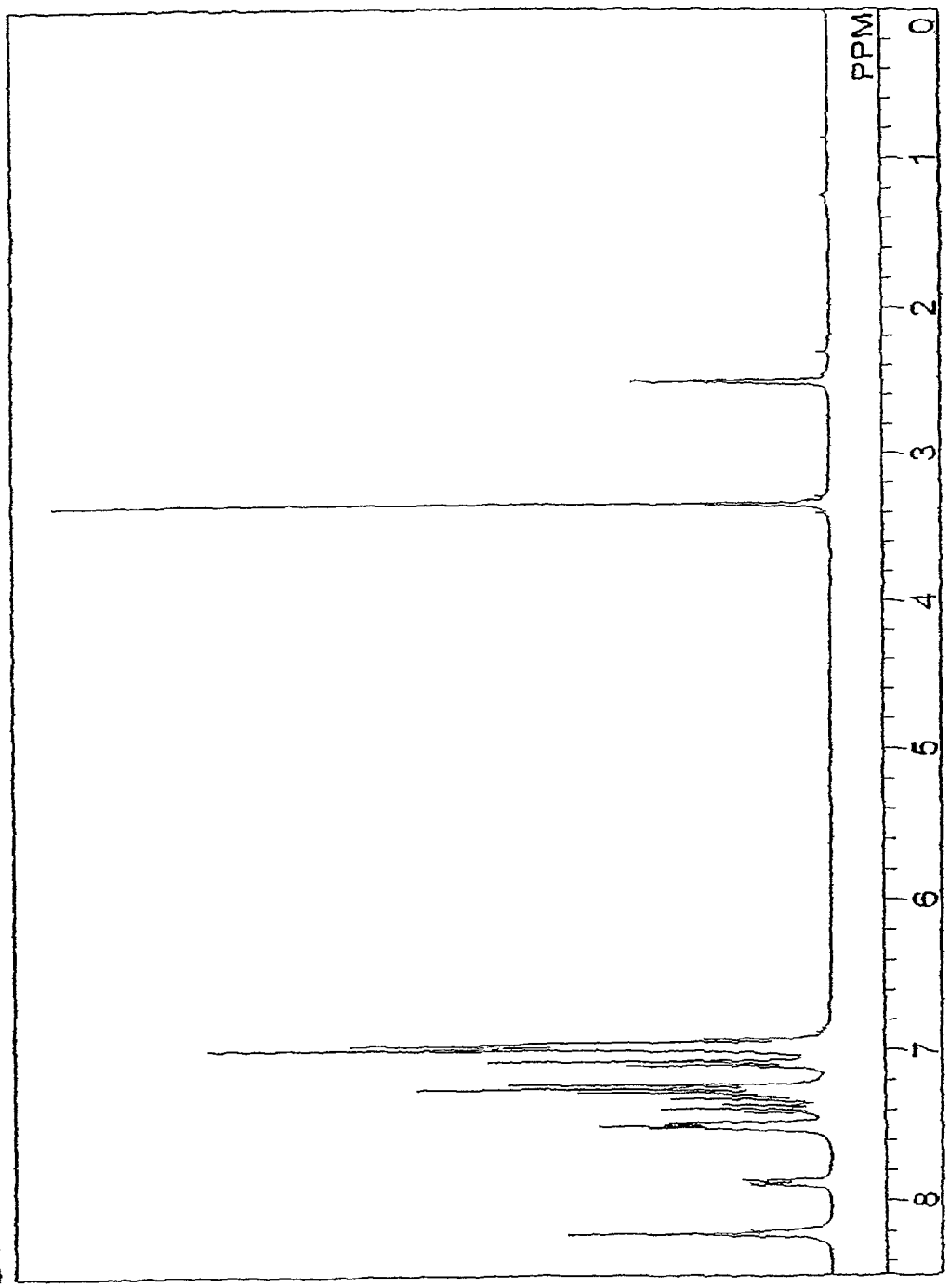
FIG. 21 is a chart of $^1$H-NMR of N-(4-diphenylaminophenyl)-N-(1-naphthyl)amine.
Figure 22:
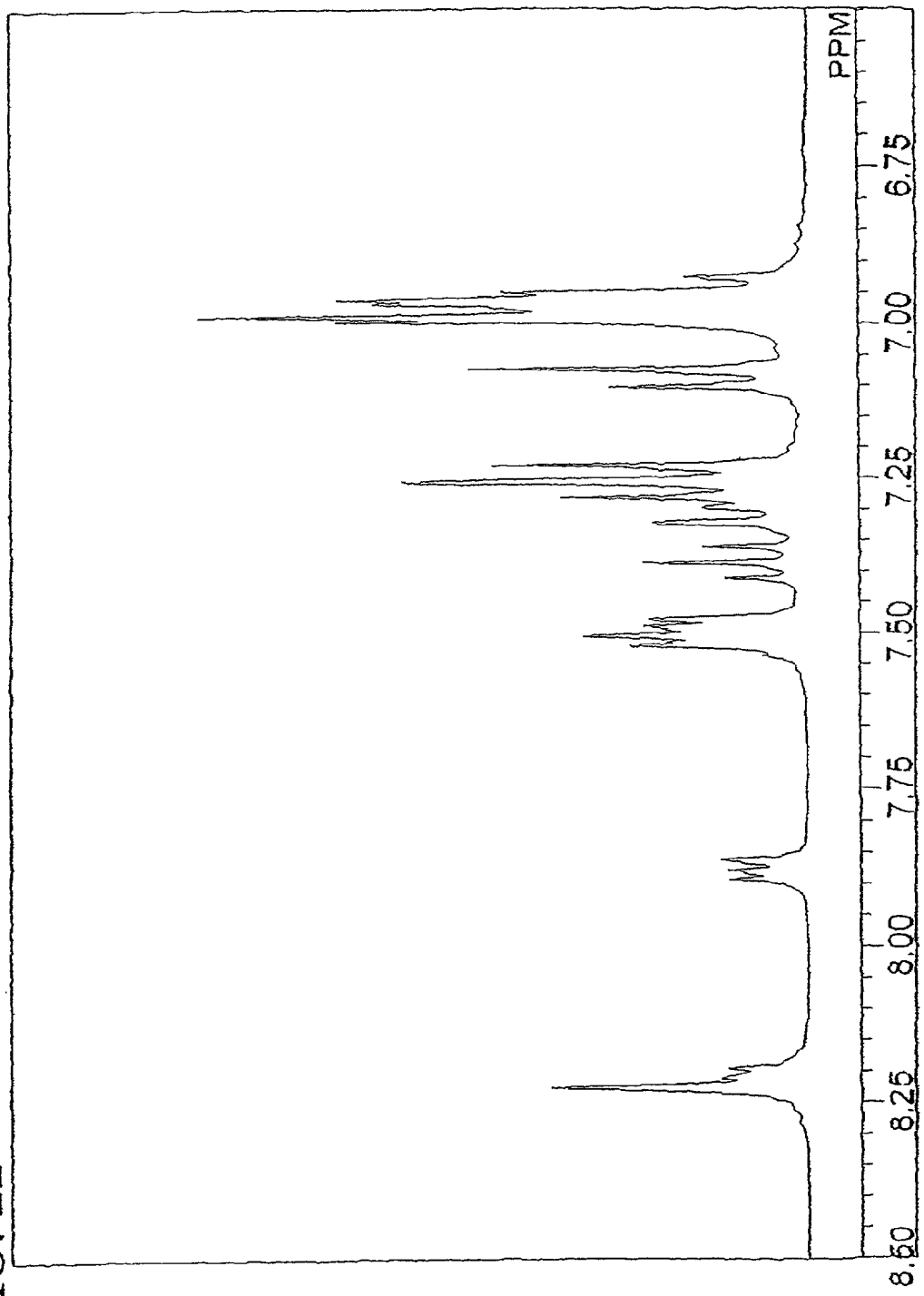
FIG. 22 is a chart of $^1$H-NMR of N-(4-diphenylaminophenyl)-N-(1-naphthyl)amine.
Figure 23:
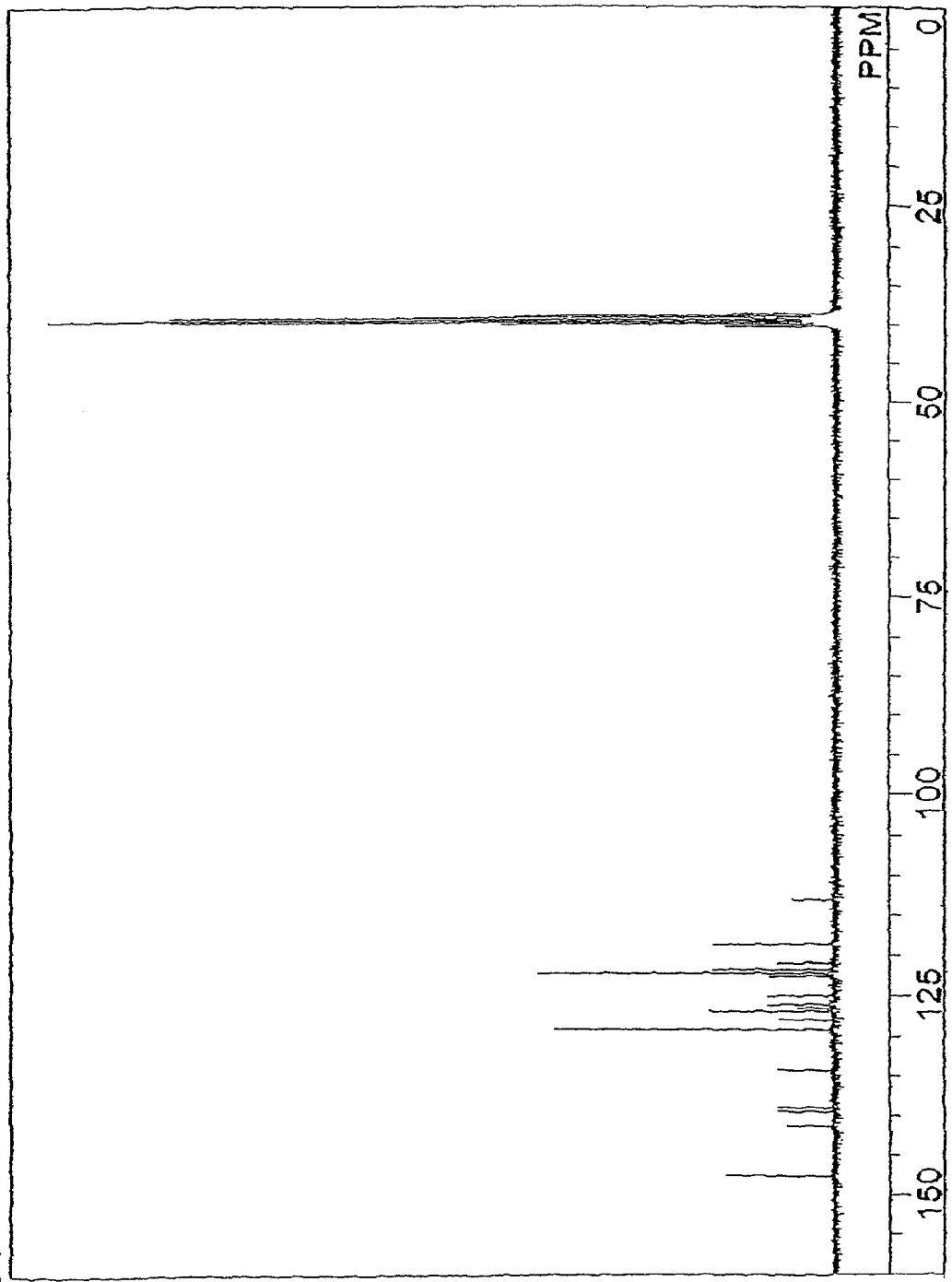
FIG. 23 is a chart of $^{13}$C-NMR of N-(4-diphenylaminophenyl)-N-(1-naphthyl)amine.

A flask was charged with 3.2 g (10 mmol) of 4-bromotriphenylamine, 1.4 g (10 mmol) of 1-aminonaphthalene, 58 mg (0.1 mmol) of dibenzylideneacetonepalladium(0), and 3.0 g (30 mmol) of sodium tert-butoxide and the atmosphere in the flask was replaced by nitrogen. 40 ml of dehydrated xylene was added thereto. Degassing was carried out for approximately 3 minutes until no more air bubbles were generated. 540 mg (1.0 mmol) of 1,1-bis(diphenylphosphino)ferrocene was added thereto and the solution was stirred for 6.5 hours at 90° C. in an atmosphere of nitrogen. After approximately 300 ml of toluene was added thereto, the solution was filtered through florisil, alumina, and celite. The obtained filtrate was washed with water and a saturated aqueous solution of sodium chloride. The organic layer was dried by magnesium sulfate. The obtained material was filtered, then, condensed, and then, purified by silica gel column chromatography (toluene and hexane in a ratio of 3:7). The obtained solution was condensed, then, hexane was added thereto and the object was precipitated by using an ultra sonic washing machine. The obtained solid was filtered to obtain 1.8 g of N-(4-diphenylaminophenyl)-N-(1-naphthyl)amine as white powder in a yield of 46%. The NMR data of the object are indicated below. $^1$H NMR (300 MHz, DMSO-d); δ=6.93-7.00 (m, 8H); 7.09 (d, j=8.7, 2H), 7.23-7.32 (m, 5H), 7.39 (t, j=7.8, 1H), 7.48-7.52 (m, 3H), 7.86-7.90 (m, 1H), 8.20-8.23 (m, 2H). $^{13}$C NMR (60 MHz, DMSO-d); δ=113.2, 118.6, 120.9, 121.7, 122.2, 122.6, 125.0, 126.0, 126.2, 126.6, 127.0, 128.1, 129.3, 134.4, 139.1, 139.6, 141.4, 147.6. FIG. 21 shows a chart of $^1$H NMR and FIG. 22 shows an enlarged view of the portion from 6.5 to 8.5 ppm in FIG. 21. FIG. 23 shows a chart of $^{13}$C NMR.

[Step 2]
A synthesis method of 3-[N-(4-diphenylaminophenyl)-N-(1-naphthyl)amino]-9-phenylcarbazole (abbreviation: PCzTPN1) is described. A synthesis scheme of 3-[N-(4-diphenylaminophenyl)-N-(1-naphthyl)amino]-9-phenylcarbazole (abbreviation: PCzTPN1) is described in (A-9).

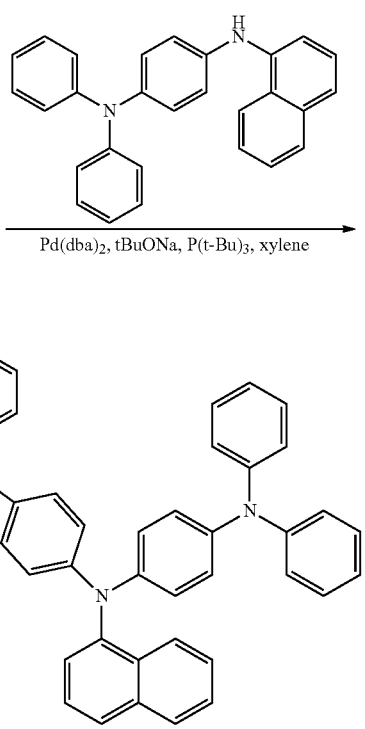

(A-9)

Figure 24:
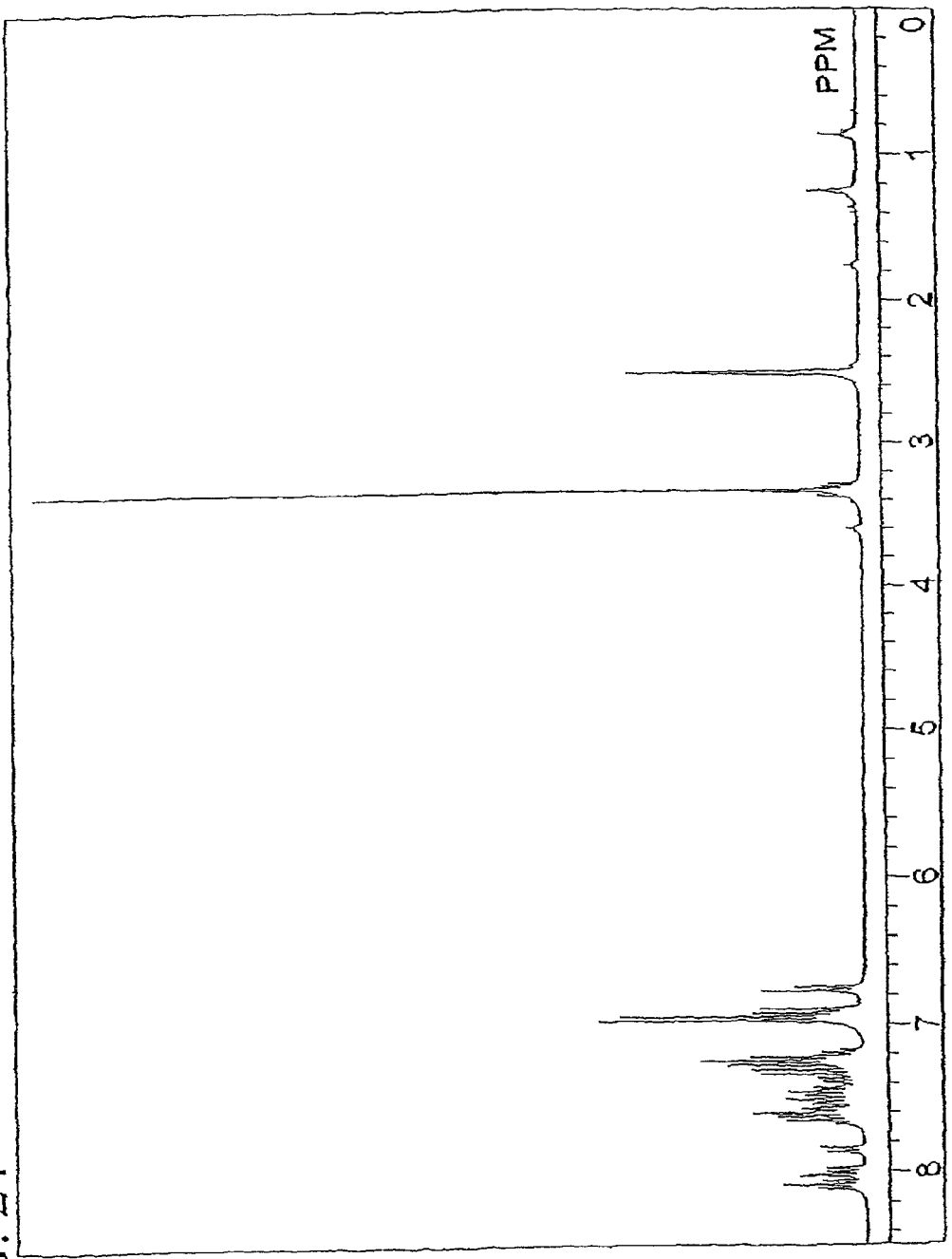
FIG. 24 is a chart of $^1$H-NMR of 3-[N-(4-diphenylaminophenyl)-N-(1-naphthyl)amino]-9-phenylcarbazole.
Figure 25:
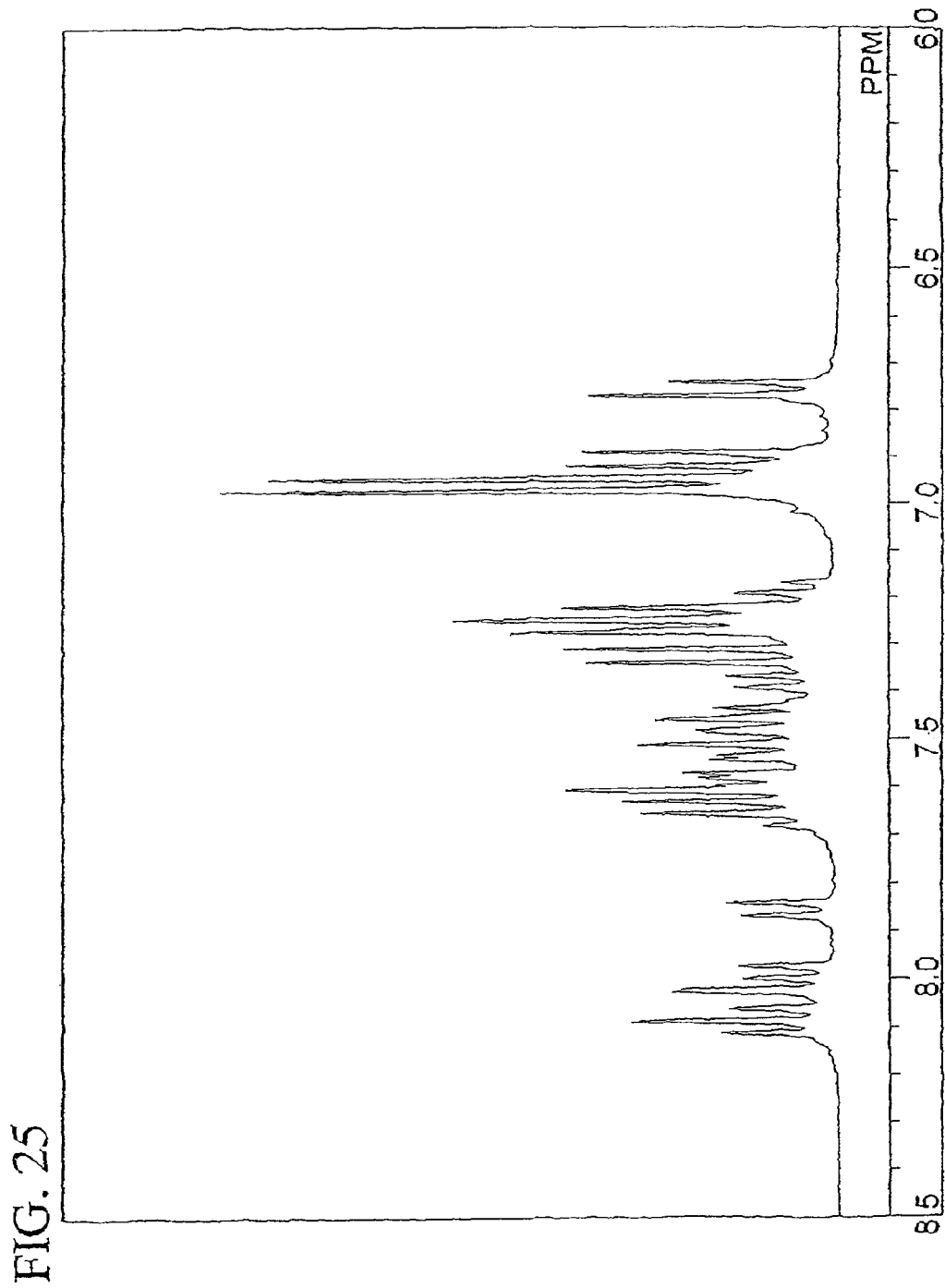
FIG. 25 is a chart of $^1$H-NMR of 3-[N-(4-diphenylaminophenyl)-N-(1-naphthyl)amino]-9-phenylcarbazole.

A flask was charged with 740 mg (2.0 mmol) of 3-iodo-9-phenylcarbazole, 700 mg (1.8 mmol) of N-(4-diphenylaminophenyl)-N-(1-naphthyl)amine, 12 mg (0.02 mmol) of dibenzylideneacetonepalladium, and 600 mg (6.0 mmol) of sodium tert-butoxide and the atmosphere in the flask was replaced by nitrogen. 5 ml of dehydrated xylene was added thereto and degassing was carried out for 3 minutes. After 0.1 ml (0.05 mmol) of tri-tert-butylphosphine (10 w % hexane solution) was added thereto, the solution was stirred for 5.5 hours at 90° C. in an atmosphere of nitrogen. Toluene of approximately 100 ml was added thereto and the solution was filtered through florisil, alumina, and celite. The obtained filtrate was washed with water and a saturated aqueous solution of sodium chloride. The organic layer was dried by magnesium sulfate. The obtained material was filtered, and condensed, then, purified by silica gel column chromatography (toluene and hexane in a ratio of 3:7). The obtained solution was condensed. Then, hexane was added thereto and the object was precipitated by using an ultra sonic washing machine. The obtained solid was filtered to obtain 500 mg of PCzTPN1 as yellow powder in a yield of 44%. The NMR data of the object are indicated below. $^1$H NMR (300 MHz, DMSO-d); δ=6.74 (d, j=8.7, 2H), 6.88-7.00 (m, 8H), 7.16-7.67 (m, 23H), 7.84 (d, j=8.4, 1H), 7.97 (d, j=8.1, 1H), 8.02 (s, 1H), 8.08 (t, j=7.8, 2H). FIG. 24 shows chart of $^1$H NMR and FIG. 25 shows an enlarged view of the portion from 6.0 to 8.5 ppm in FIG. 24.

Thermogravimetry-differential thermal analysis (TG-DTA) of the obtained PCzTPN1 was carried out. The thermogravimetric/differential thermal analyzer (manufactured by Seiko Instruments Electronics Ltd., TG/DTA 320) was used for the measurement. A thermophysical property of the obtained PCzTPN1 was evaluated with 10° C./min of programming rate in an atmosphere of nitrogen. From the relation between weight and temperature (thermogravimetric analysis), the temperature at which the weight was reduced to be 95% or less of the weight at the beginning of the measurement under normal pressure was 380° C.

Figure 17:
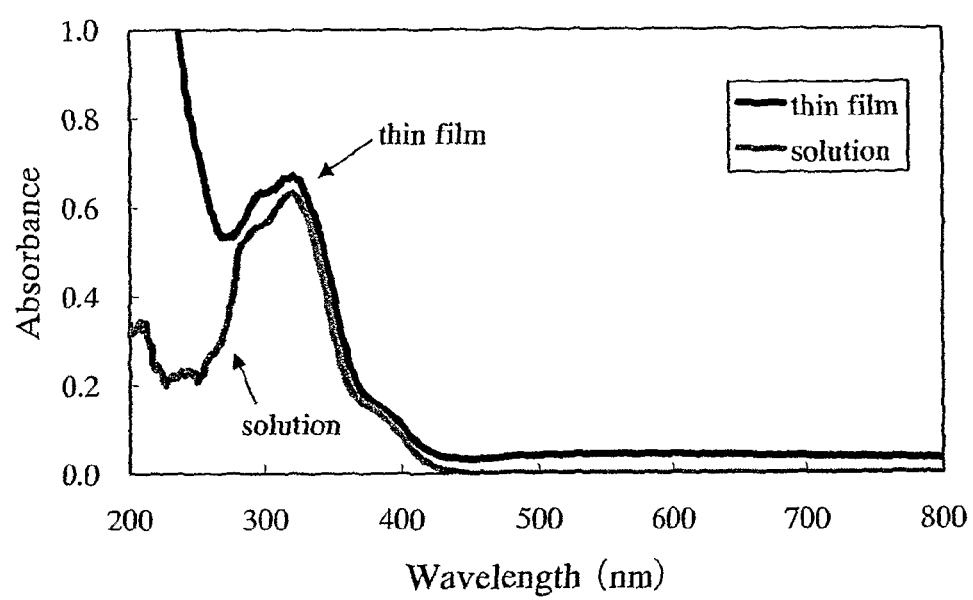
FIG. 17 is a diagram showing an absorption spectrum of 3-[N-(4-diphenylaminophenyl)-N-(1-naphthyl)amino]-9-phenylcarbazole which is a carbazole derivative according to the present invention.
Figure 18:
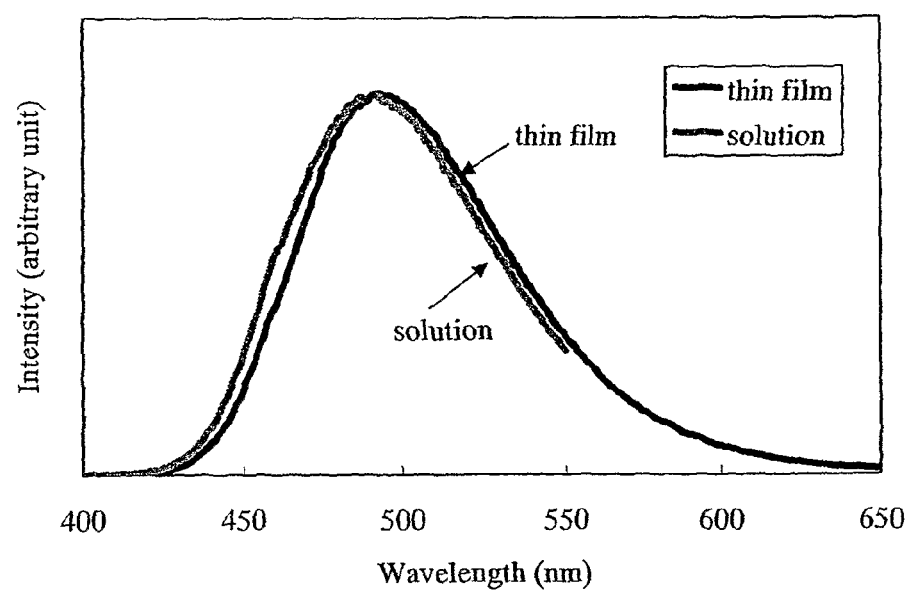
FIG. 18 is a diagram showing an emission spectrum of 3-[N-(4-diphenylaminophenyl)-N-(1-naphthyl)amino]-9-phenylcarbazole which is a carbazole derivative according to the present invention.

Absorption spectra of the toluene solution of PCzTPN1 and a thin film of PCzTPN1 are shown in FIG. 17. The UV/VIS spectrometer (manufactured by JASCO Corporation, V-550) was used for the measurement. In FIG. 17, a horizontal axis shows wavelength (nm) and a vertical axis shows absorbance. The largest absorption wavelength was 314 nm in the case of the toluene solution and the largest absorption wavelength was 314 nm in the case of the thin film. Emission spectra of the toluene solution of PCzTPN1 (excitation wavelength of 330 nm) and the thin film of PCzTPN1 (excitation wavelength of 350 nm) are shown in FIG. 18. In FIG. 18, a horizontal axis shows wavelength (nm) and a vertical axis shows emission intensity (arbitrary unit). The highest emission wavelength was 490 nm (excitation wavelength of 330 nm) in the case of toluene solution and the highest emission wavelength was 500 nm (excitation wavelength of 350 nm) in the case of the thin film.

Measurement of HOMO level and LUMO level of PCzTPN1 in the state of a thin film was carried out. A value of the HOMO level was obtained by converting a value of ionization potential measured by the photoelectron spectrometer (manufactured by Riken Keiki Co., Ltd., AC-2) into a negative value. On the other hand, a value of the LUMO level was obtained by using the value of absorption edge of the thin film in FIG. 17 as an energy gap to be added to the value of the HOMO level. As a result, the HOMO level and the LUMO level were −5.21 eV and −2.28 eV, respectively.

Example 8

A synthesis method of 3,6-bis[N-(4-diphenylaminophenyl)-N-(1-naphthyl)amino]-9-phenylcarbazole (abbreviation: PCzTPN2) represented by a structural formula (61) will be described.

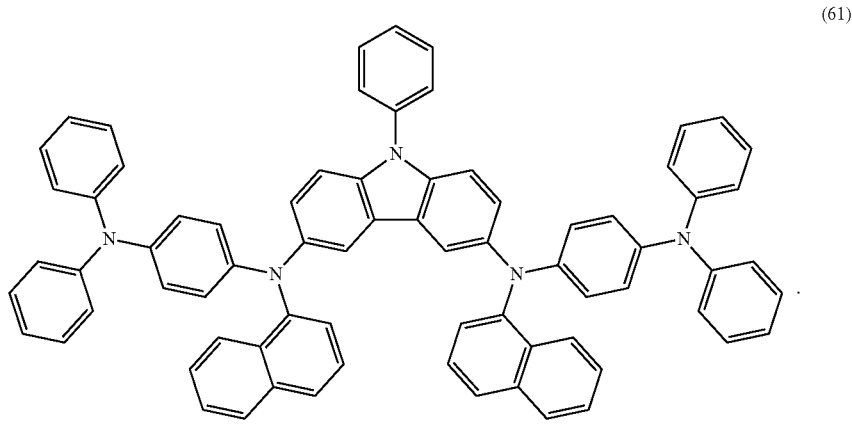 [SMILES: c1ccc(N(c2ccccc2)c2ccc(N(c3ccc4c(c3)c3cc(N(c5ccc(N(c6ccccc6)c6ccccc6)cc5)c5cccc6ccccc56)ccc3n4-c3ccccc3)c3cccc4ccccc34)cc2)cc1]

(61)

[Step 1]

A synthesis scheme of 3,6-bis-[N-(4-diphenylaminophenyl)-N-(1-naphthyl)amino]-9-phenylcarbazole (abbreviation: PCzTPN2) is described in (A-10).

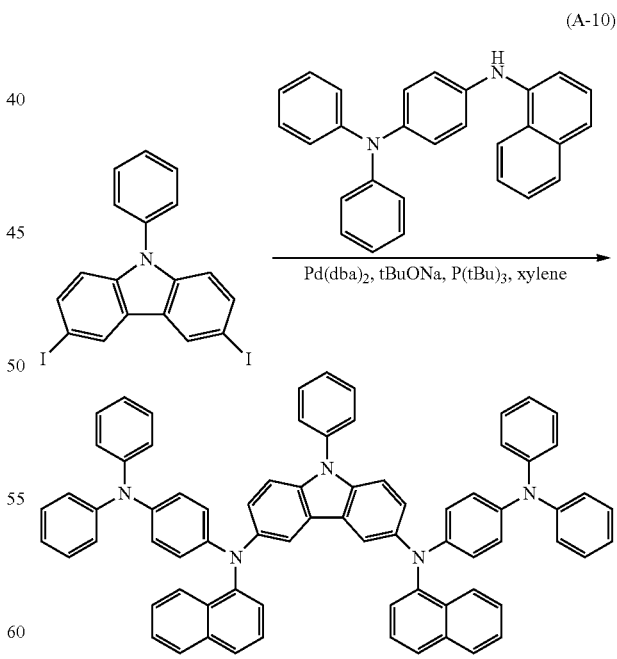

(A-10)

Figure 26:
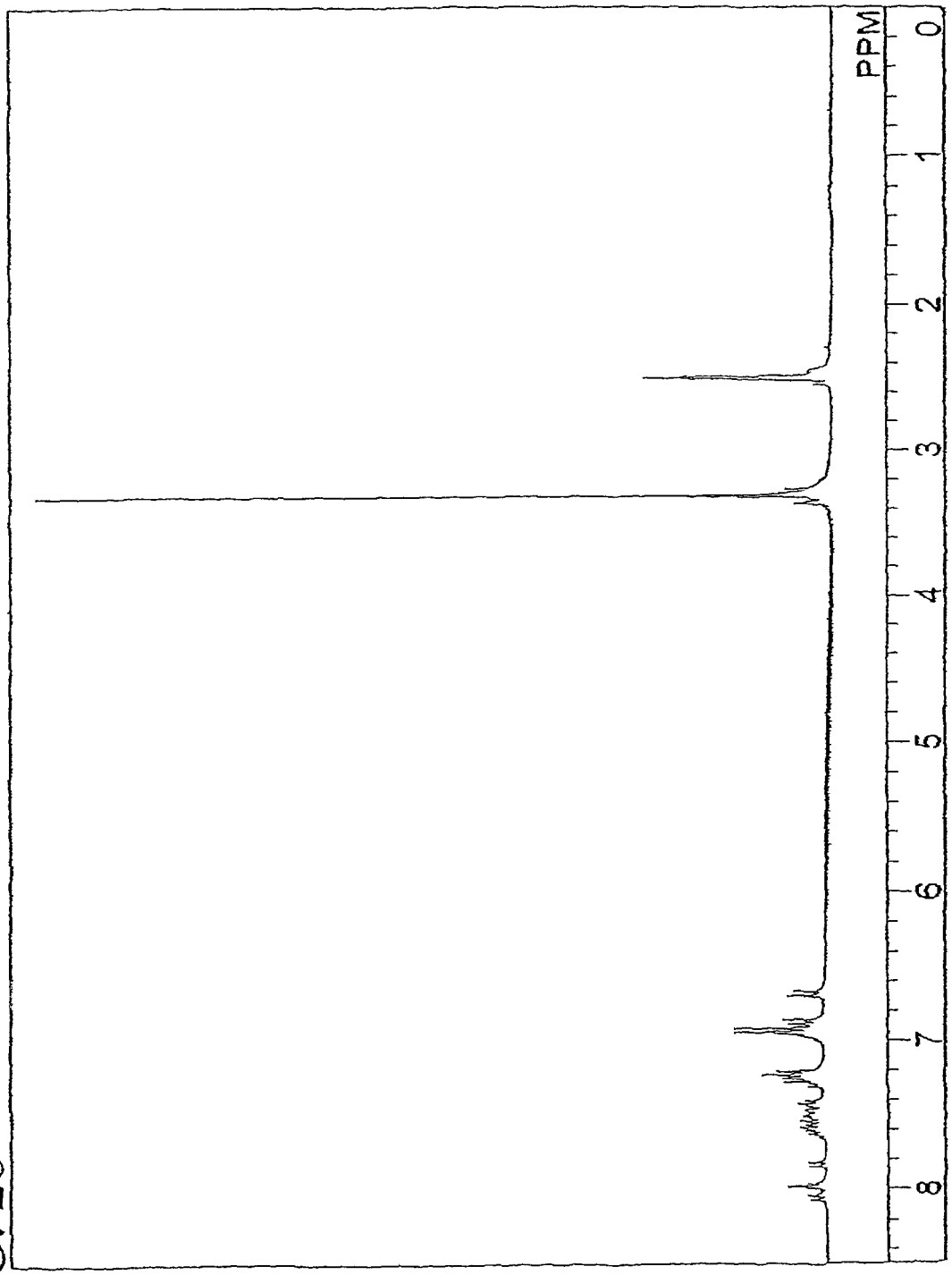
FIG. 26 is a chart of $^1$H-NMR of 3,6-bis[N-(4-diphenylaminophenyl)-N-(1-naphthyl)amino]-9-phenylcarbazole.
Figure 27:
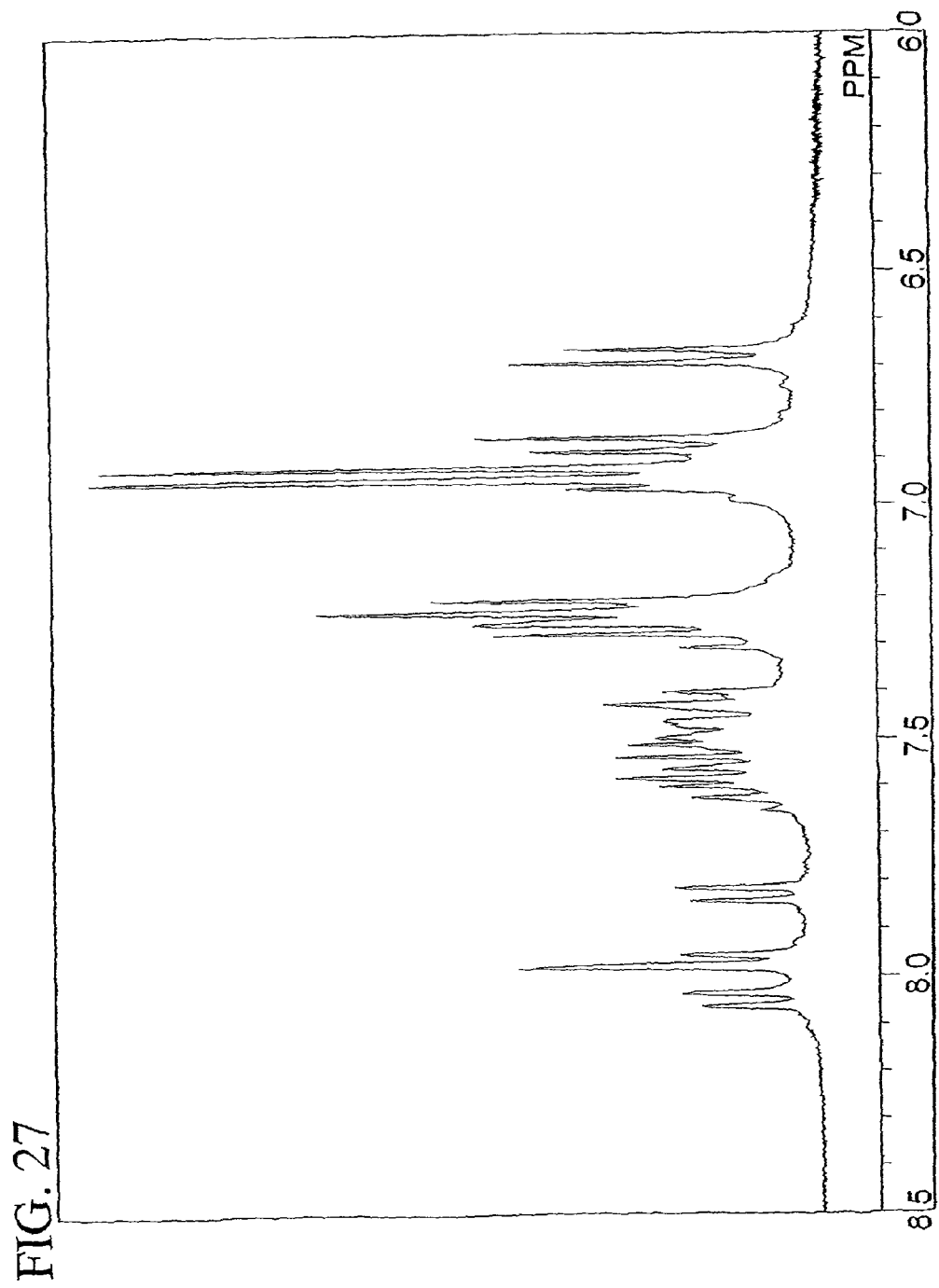
FIG. 27 is a chart of $^1$H-NMR of 3,6-bis[N-(4-diphenylaminophenyl)-N-(1-naphthyl)amino]-9-phenylcarbazole.

A flask was charged with 740 mg (1.5 mmol) of 3,6-diiodo-9-phenylcarbazole, 1.2 g (3 mmol) of N-(4-diphenylaminophenyl)-N-(1-naphthyl)amine, 18 mg (0.03 mmol) of dibenzylideneacetonepalladium, and 1.0 g (10 mmol) of sodium tert-butoxide, and the atmosphere in the flask was replaced by nitrogen. 7.5 ml of dehydrated xylene was added thereto and degassing was carried out for 3 minutes. After 0.2 ml (0.1 mmol) of tri-tert-butylphosphine (10 w % hexane solution) was added thereto, the solution was stirred for 7 hours at 90° C. in an atmosphere of nitrogen. Toluene of approximately 300 ml was added thereto and the solution was filtered through florisil, alumina, and celite. The obtained filtrate was washed with water and a saturated aqueous solution of sodium chloride. The organic layer was dried by magnesium sulfate. The obtained material was filtered, and condensed, then, purified by silica gel column chromatography (toluene and hexane in a ratio of 3:7). The obtained solution was condensed. Then, hexane was added thereto and the object was precipitated by using an ultra sonic washing machine. The obtained solid was filtered to obtain 1.0 mg of PCzTPN2 as yellow powder in a yield of 66%. The NMR data of the object are indicated below. $^1$H NMR (300 MHz, DMSO-d); δ=6.68 (d, j=9.0, 4H), 6.86-6.97 (m, 16H), 7.20-6.97 (m, 16H), 7.20-7.65 (m, 25H), 7.83 (d, j=8.1, 2H), 7.95-7.98 (m, 4H), 8.05 (d, j=8.4, 2H). FIG. 26 shows a chart of $^1$H NMR and FIG. 27 shows an enlarged view of the portion from 6.0 to 8.5 ppm in FIG. 26.

Thermogravimetry-differential thermal analysis (TG-DTA) of the obtained PCzTPN2 was carried out. The thermogravimetric/differential thermal analyzer (manufactured by Seiko Instruments Electronics Ltd., TG/DTA 320) was used for the measurement. A thermophysical property of the obtained PCzTPN2 was evaluated with 10° C./min of programming rate in an atmosphere of nitrogen. From the relation between weight and temperature (thermogravimetric analysis), the temperature at which the weight was reduced to be 95% or less of the weight at the beginning of the measurement under normal pressure was 470° C.

Figure 19:
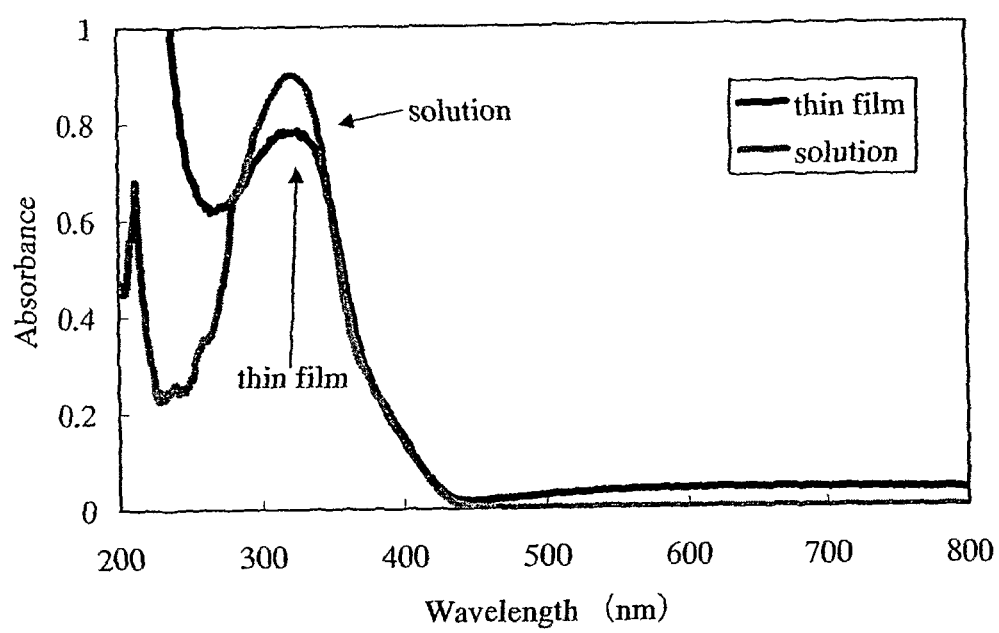
FIG. 19 is a diagram showing an absorption spectrum of 3,6-bis[N-(4-diphenylaminophenyl)-N-(1-naphthyl)amino]-9-phenylcarbazole which is a carbazole derivative according to the present invention.
Figure 20:
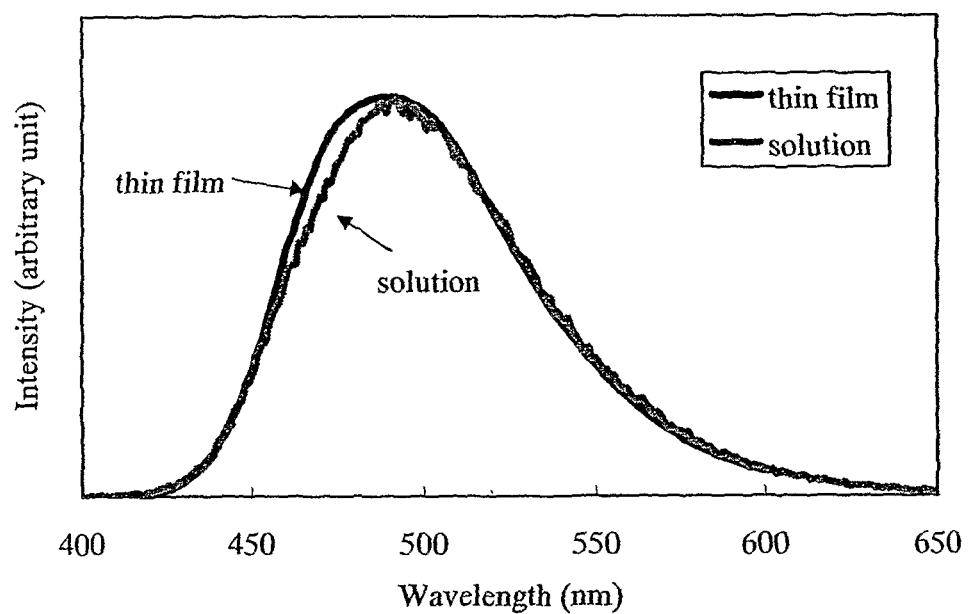
FIG. 20 is a diagram showing an emission spectrum of 3,6-bis[N-(4-diphenylaminophenyl)-N-(1-naphthyl)amino]-9-phenylcarbazole which is a carbazole derivative according to the present invention.

Absorption spectra of the toluene solution of PCzTPN2 and a thin film of PCzTPN2 are shown in FIG. 19. The UV/VIS spectrometer (manufactured by JASCO Corporation, V-550) was used for the measurement. In FIG. 19, a horizontal axis shows wavelength (nm) and a vertical axis shows absorbance. The largest absorption wavelength was 320 nm in the case of the toluene solution and the largest absorption wavelength was 393 nm in the case of the thin film. Emission spectra of the toluene solution of PCzTPN2 (excitation wavelength of 335 nm) and the thin film of PCzTPN2 (excitation wavelength of 320 nm) are shown in FIG. 20. In FIG. 20, a horizontal axis shows wavelength (nm) and a vertical axis shows emission intensity (arbitrary unit). The highest emission wavelength was 493 nm (excitation wavelength of 335 nm) in the case of the toluene solution and the highest emission wavelength was 488 nm (excitation wavelength of 320 nm) in the case of the thin film.

Measurement of HOMO level and LUMO level of PCzTPN2 in the state of a thin film was carried out. A value of the HOMO level was obtained by converting a value of ionization potential measured by the photoelectron spectrometer (manufactured by Riken Keiki Co., Ltd., AC-2) into negative value. On the other hand, a value of the LUMO level was obtained by using the value of absorption edge of the thin film in FIG. 19 as an energy gap to be added to the value of the HOMO level. As a result, the HOMO level and the LUMO level were −5.13 eV and −2.24 eV, respectively.

Example 9

In this example, an oxidation reaction property of 3-[N-(4-diphenylaminophenyl)-N-(1-naphthyl)amino]-9-phenylcarbazole (abbreviation: PCzTPN1) which is represented by the structural formula (33) was measured by cyclic voltammetry (CV) measurement using an electrochemical analyzer (manufactured by BAS Inc., ALS model 600A).

The solution for the CV measurement was prepared by dissolving supporting electrolyte of tetra-n-butylammonium perchlorate (n-Bu$_4$NClO$_4$) (manufactured by Tokyo Kasei Kogyo., LTD., catalog number: T0836) so that the material reaches a concentration of 100 mmol/L and by dissolving the material to be measured so that the material reaches a concentration of 1 mmol/L using dehydrated dimethylformamide (DMF) (manufactured by Aldrich Corp., 99.8%, catalog number: 22705-6) as solvent. A platinum electrode (manufactured by BAS Inc., PTE platinum electrode) as an indicator electrode, a platinum electrode (manufactured by BAS Inc., Pt counter electrode for VC-3, 5 cm Peek) as an auxiliary electrode, and an Ag/Ag$^+$ electrode (manufactured by BAS Inc., RE-5 Reference electrode for nonaqueous solvent) as a reference electrode were used. The measurement was carried out at a room temperature.

An oxidation reaction property of PCzTPN1 was measured as follows: The electric potential of the indicator electrode to the reference electrode was changed from −0.03 to 0.4 V, and then, from 0.4 to −0.03 V. If scanning for changing from −0.03 to 0.4 V, and from 0.4 to −0.03 V was one cycle, 100 cycles of the oxidation reaction property of PCzTPN1 was measured. The CV measurement was carried out with a scan speed of 0.1 V/s.

Figure 28:
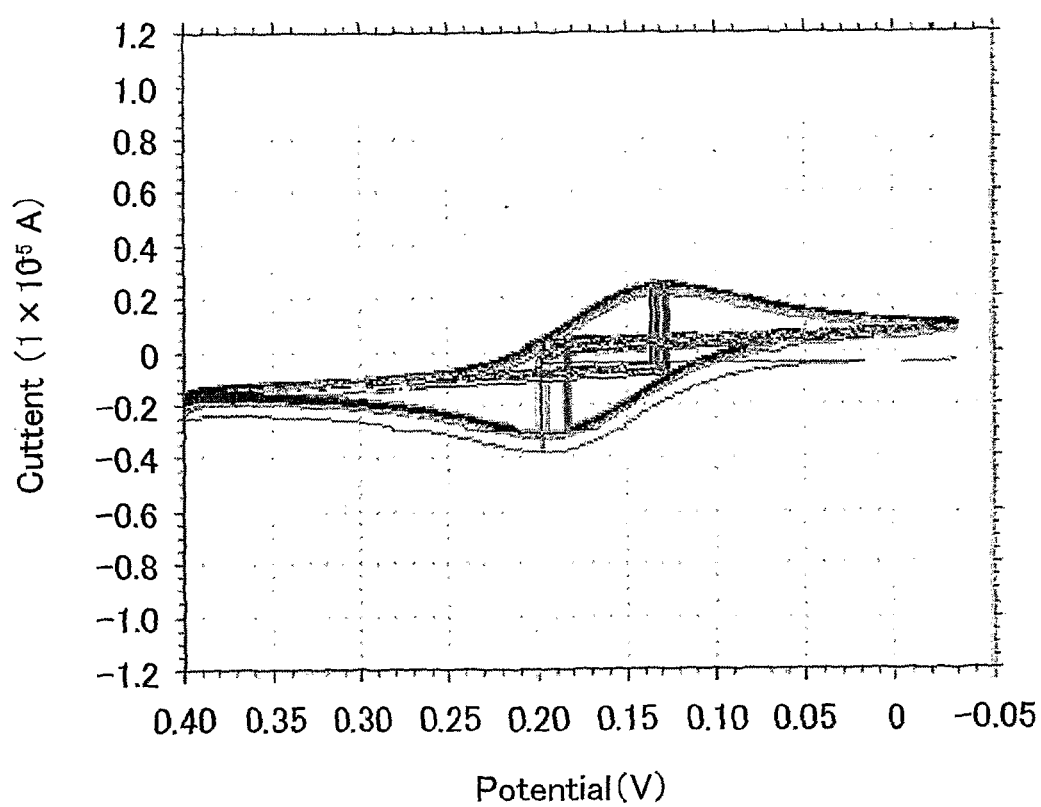
FIG. 28 is a diagram showing the result of the CV measurement of 3-[N-(4-diphenylaminophenyl)-N-(1-naphthyl)amino]-9-phenylcarbazole.

FIG. 28 shows the result of the measurement of the oxidation reaction property of PCzTPN1. In FIG. 28 a horizontal axis shows potential (V) of the reference electrode to the indicator electrode and a vertical axis shows current ($1\times10^{-5}$ A) between the reference electrode and the auxiliary electrode.

FIG. 28 shows that the oxidation potential was 0.20 V (vs. Ag/Ag$^+$electrode). After the 100 cycles of scanning were carried out, the peak position and the peak intensity of the CV carve hardly changed. Therefore, it can be said that a carbazole derivative according to the present invention is quite stable of oxidation reaction.

Example 10

In this example, an oxidation reaction property of 3,6-bis [N-(4-diphenylaminophenyl)-N-(1-naphthyl)amino]-9-phenylcarbazole (abbreviation: PCzTPN2) which is represented by the structural formula (61) was measured by cyclic voltammetry (CV) measurement using the electrochemical analyzer (manufactured by BAS Inc., ALS model 600A).

The solution for the CV measurement was prepared by dissolving supporting electrolyte of tetra-n-butylammonium perchlorate (n-Bu$_4$NClO$_4$) (manufactured by Tokyo Kasei Kogyo., LTD., catalog number: T0836) so that the material reaches a concentration of 100 mmol/L and by dissolving the material to be measured so that the material reaches a concentration of 1 mmol/L using dehydrated dimethylformamide (DMF) (manufactured by Aldrich Corp., 99.8%, catalog number: 22705-6) as solvent. A platinum electrode (manufactured by BAS Inc., PIE platinum electrode) as an indicator electrode, a platinum electrode (manufactured by BAS Inc., Pt counter electrode for VC-3, 5 cm Peek) as an auxiliary electrode, and an Ag/Ag$^+$ electrode (manufactured by BAS Inc., RE-5 Reference electrode for nonaqueous solvent) as a reference electrode were used. The measurement was carried out at a room temperature.

An oxidation reaction property of PCzTPN2 was measured as follows. The electric potential of the indicator electrode to the reference electrode was changed from −0.36 to 0.4 V, and then, from 0.4 to −0.36 V. If scanning for changing from −0.36 to 0.4 V and from 0.4 to −0.36 V is 1 cycle, 100 cycles of the oxidation reaction property of PCzTPN1 was measured. The CV measurement was carried out with a scan speed of 0.1 V/s.

Figure 29:
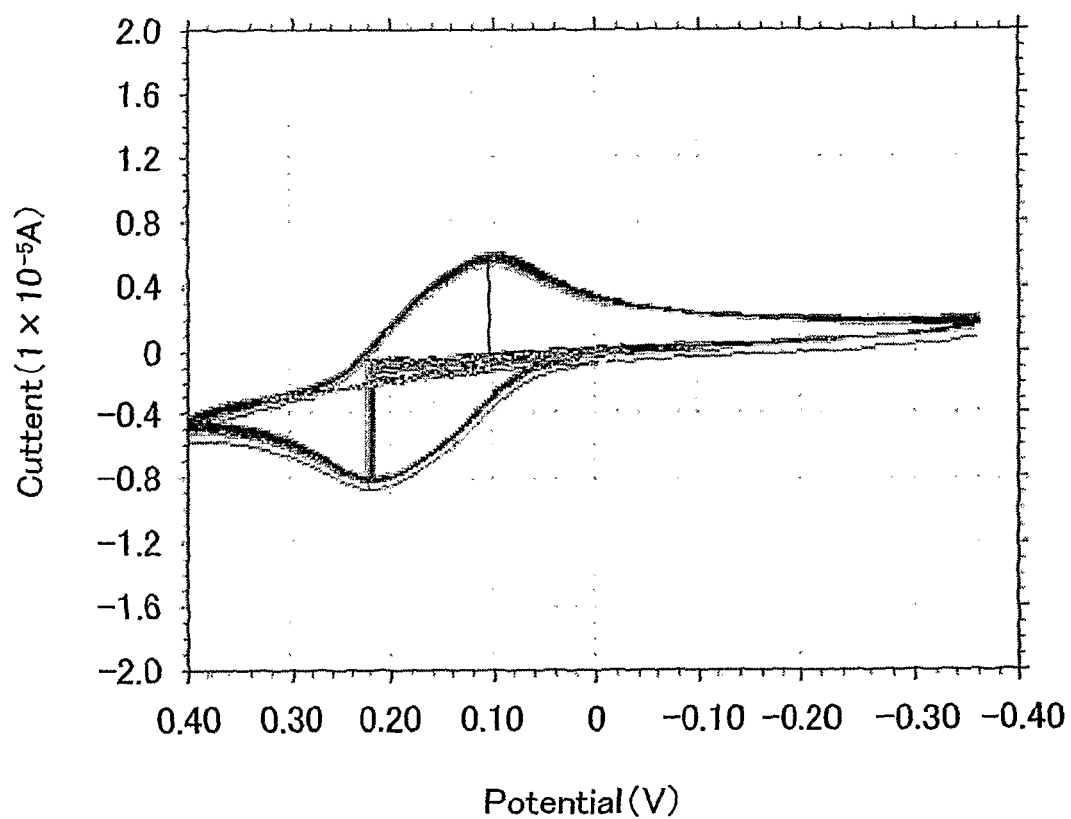
FIG. 29 is a diagram showing the result of the CV measurement of 3,6-bis[N-(4-diphenylaminophenyl)-N-(1-naphthyl)amino]-9-phenylcarbazole.

FIG. 29 shows the result of the measurement of the oxidation reaction property of PCzTPN2. In FIG. 29 a horizontal axis shows potential (V) of the reference electrode to the indicator electrode and a vertical axis shows current ($1 \times 10^{-5}$ A) between the reference electrode and the auxiliary electrode.

FIG. 29 shows that the oxidation potential was 0.22 V (vs. Ag/Ag$^+$electrode). After the 100 cycles of scanning were carried out, the peak position and the peak intensity of the CV carve hardly changed. Therefore, it can be said that a carbazole derivative according to the present invention is quite stable of oxidation reaction.

Example 11

Figure 30:
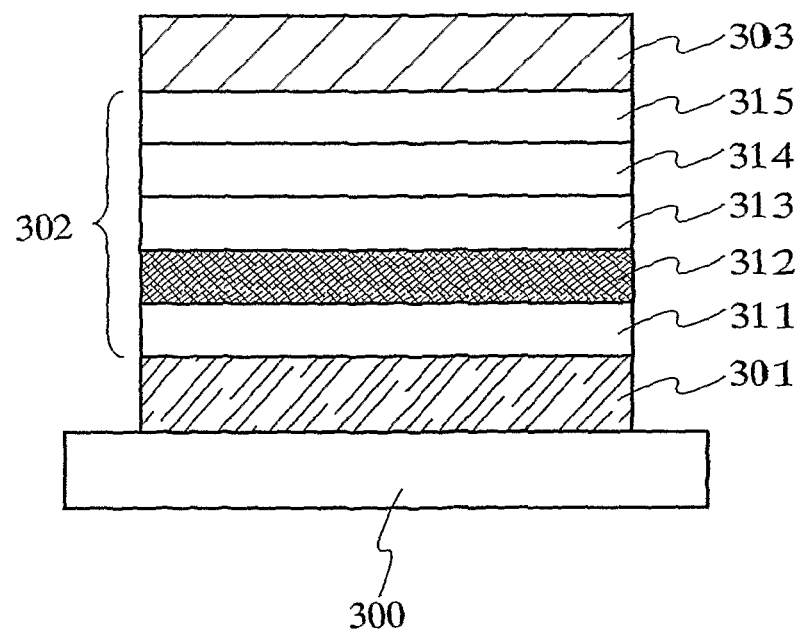
FIG. 30 is an explanatory view of a light-emitting element according to the present invention.

In this example, a light emitting element having a carbazole derivative PCzDPA1 represented by the structural formula (28) and synthesized in Example 1 will be described with reference to FIG. 30.

A first electrode 301 of the light emitting element was formed over a substrate 300. In this example, the first electrode functions as an anode. The anode was formed by a sputtering method using indium tin oxide containing silicon oxide which is a material for a transparent conductive film to have a thickness of 110 nm.

Then, a layer containing a light emitting material 302 was formed over the first electrode 301. In this example, the layer containing the light emitting material 302 was formed by stacking a hole injecting layer 311, a hole transporting layer 312, a light emitting layer 313, an electron transporting layer 314, and an electron injecting layer 315.

The substrate provided with the first electrode 301 was fixed in a substrate holder in a commercially available vacuum vapor deposition equipment so that the surface provided with the first electrode 301 faces downward. DNTPD was provided to a deposition source in the vacuum vapor deposition equipment to form the hole injecting layer 311 by a vapor deposition method with a resistance heating method to have a thickness of 50 nm.

Then, the hole transporting layer 312 was formed with a material which is excellent in a hole transporting property. In this example, the hole transporting layer 211 was formed by the same method as that of the hole injecting layer using PCzDPA1 represented by the structural formula (28) to have a thickness of 10 nm.

The light emitting layer 313 was formed. In the light emitting layer 313, holes and electrons recombine with each other and emit light. In this example, a host material of Alq$_3$ and a guest material of coumarin 6 were co-evaporated to form the light emitting layer 313 to have a thickness of 40 nm so that the weight ratio can be 1:0.08 (=Alq$_3$:coumarin 6). Thereby coumarin 6 was dispersed in the layer made of Alq$_3$.

The electron transporting layer 314 was formed. As a material for the electron transporting layer 314, various kinds of electron transporting materials can be used. In this example, the electron transporting layer was formed by a vapor deposition method using Alq$_3$ to have a thickness of 30 nm.

Thereafter, the electron injecting layer 315 was formed. As the electron injecting layer 315, various kinds of electron injecting materials can be used. In this example, the electron injecting layer was formed by a vapor deposition method using calcium fluoride to have a thickness of 1 nm.

After the layer containing the light emitting material 302 was formed by stacking the hole injecting layer 311, the hole transporting layer 312, the light emitting layer 313, the electron transporting layer 314, and the electron injecting layer 315, a second electrode 303 was formed by a sputtering method or a vapor deposition method. In this example, the second electrode functions as a cathode. In this example, the cathode was formed by a vapor deposition method using Al to have a thickness of 200 nm.

Thus, a light emitting element of this example was formed.

Example 12

In this example, a light emitting element having the carbazole derivative PCzDPA2 represented by the structural formula (56) will be described.

Like Example 9, an anode was formed using indium tin oxide containing silicon oxide to have a thickness of 110 nm, a hole injecting layer was formed using DNTPD to have a thickness of 50 nm, a hole transporting layer was formed using the carbazole derivative PCzDPA2 according to the present invention represented by the structural formula (56) to have a thickness of 50 nm, a light emitting layer was formed using Alq$_3$ and coumarin 6 so that the weight ratio can be 1:0.08 (=Alq$_3$:coumarin 6) to have a thickness of 40 nm over a substrate. Then, an electron transporting layer was formed using Alq$_3$ to have a thickness of 30 nm, an electron injecting layer was formed using calcium fluoride to have a thickness of 1 nm, and a cathode was formed using Al to have a thickness of 200 nm.

Figure 31:
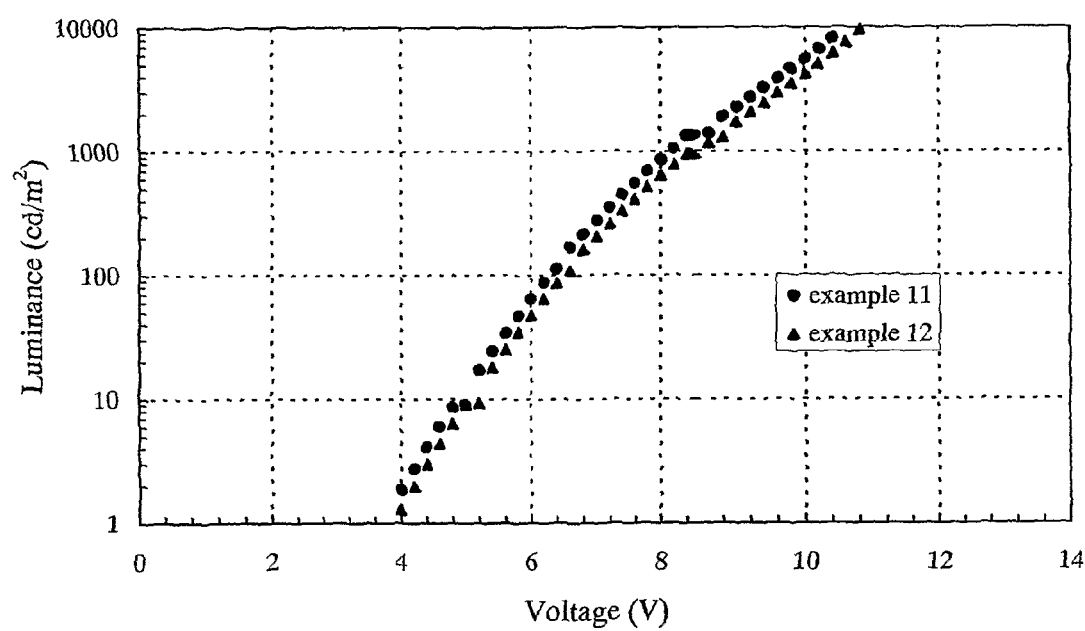
FIG. 31 is a diagram showing luminance-voltage characteristics of light emitting elements manufactured in Example 11 and Example 12.
Figure 32:
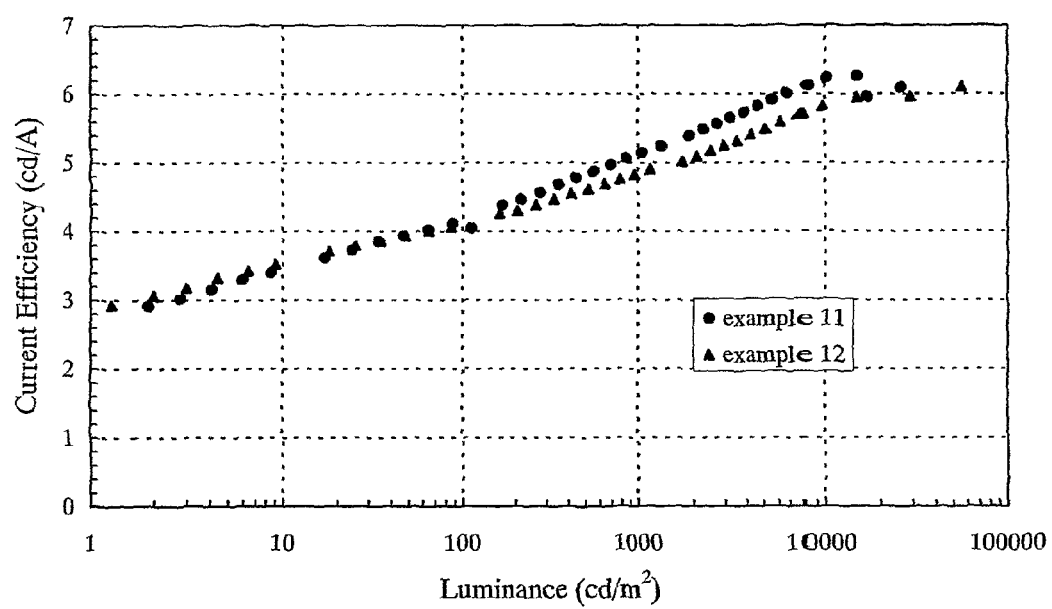
FIG. 32 is a diagram showing current efficiency-luminance characteristics of the light emitting elements manufactured in Example 11 and Example 12.
Figure 33:
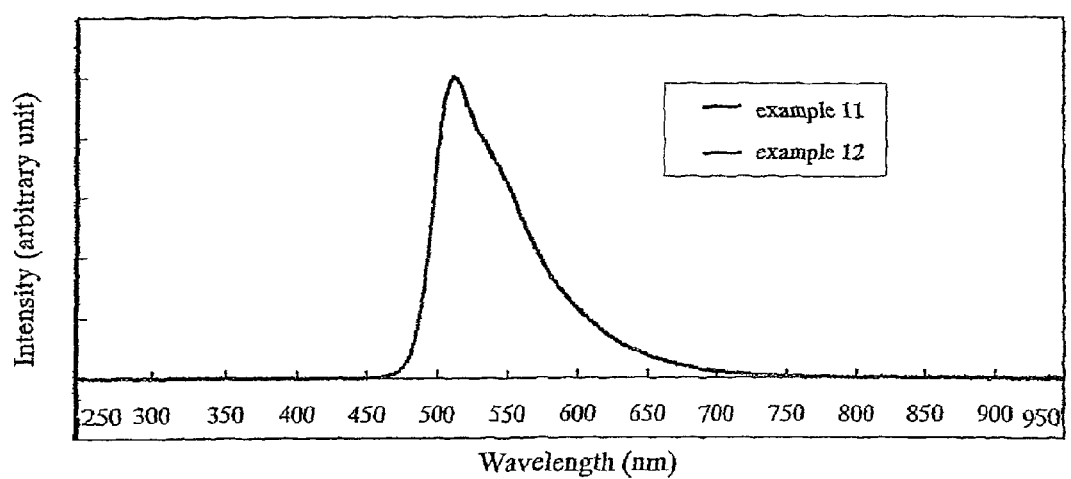
FIG. 33 is a diagram showing emission spectra of light emitting elements manufactured in Example 11 and Example 12.

Thus, a light emitting element of this example was formed. FIG. 31 shows luminance-voltage characteristics and FIG. 32 shows current efficiency-luminance characteristics of the light emitting elements manufactured in Example 11 and Example 12. FIG. 33 shows emission spectra of the light emitting elements manufactured in Example 11 and Example 12 when 1 mA of current was supplied.

According to FIGS. 31 and 32, the carbazole derivative according to the present invention was excellent in the hole transporting property and can be used for a hole transporting layer of a light emitting element. Specifically, in the case of the light emitting element manufactured in Example 11, voltage required for light emission at luminance of 1054 cd/m$^2$ was 8.2 V and a current at this time was 0.82 mA (an electric current density was 20.5 mA/cm$^2$). Current efficiency was 5.15 mA/cm$^2$ and the choromaticity coordinates were (x, y)=(0.30, 0.64). Similarly, in the case of the light emitting element manufactured in Example 12, a voltage required for luminance of 963 cd/m$^2$ was 8.4 V and a current at this time was 0.80 mA (an electric current density was 19.9 mA/cm$^2$). Current efficiency was 4.8 mA/cm$^2$ and the chromaticity coordinates were (x, y)=(0.30, 0.64).

As shown in FIG. 33, light emission is hardly observed from the hole transporting layer and an electron transporting layer which are in contact with the light emitting layer but is observed from coumarin 6 of the light emitting layer. That is, carriers are recombined with each other in the light emitting layer efficiently. By using the carbazole derivative according to the present invention, a light emitting element with improved carrier balance can be manufactured.

Example 13

Figure 34:
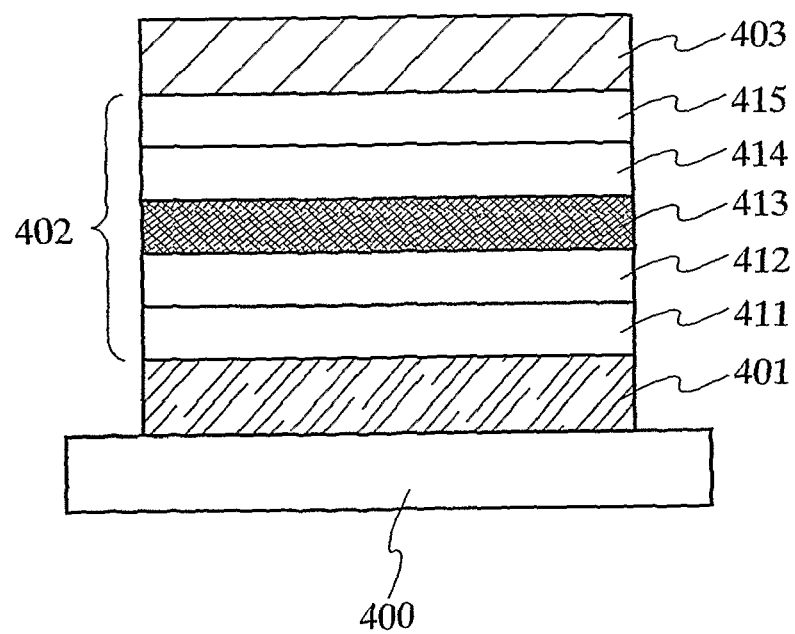
FIG. 34 is an explanatory view of a light-emitting element according to the present invention.

In this example, a light emitting element having a carbazole derivative PCzDPA2 represented by the structural formula (56) will be described with reference of FIG. 34.

A first electrode 401 of the light emitting element was formed over a substrate 400. In this example, the first electrode functions as an anode. The anode was formed by a sputtering method using indium tin oxide containing silicon oxide which is a material for a transparent conductive film to have a thickness of 110 nm.

Then, a layer containing a light emitting material 402 was formed over the first electrode 401. In this example, the layer containing the light emitting material 402 was formed by stacking a hole injecting layer 411, a hole transporting layer 412, a light emitting layer 413, an electron transporting layer 414, and an electron injecting layer 415.

The substrate provided with the first electrode 401 was fixed in a substrate holder in a commercially available vacuum vapor deposition equipment so that the surface provided with the first electrode 401 faces downward. DNTPD was provided to a deposition source in the vacuum vapor deposition equipment to form the hole injecting layer 411 by a vapor deposition method with a resistance heating method to have a thickness of 50 nm.

Then, the hole transporting layer 412 was formed with a material which is excellent in a hole transporting property. As a material for the hole transporting layer 412, various kinds of hole transporting materials can be used. In this example, the hole transporting layer 412 was formed by the same method as that of the hole injecting layer using α-NPD to have a thickness of 30 nm.

The light emitting layer 413 was formed. In the light emitting layer 413, holes and electrons recombine with each other and emit light. In this example, a host material of 2-tert-butyl-9,10-di(2-naphthyl)anthracene (abbreviation: t-BuDNA) and a guest material of PCzDPA2 represented by the structural formula (56) were co-evaporated to form the light emitting layer 413 having a thickness of 40 nm so that the weight ratio can be 1:0.05 (=t-BuDNA:PCzDPA2). Thereby PCzDPA2 was dispersed in the layer made of t-BuDNA.

The electron transporting layer 414 was formed. As a material for the electron transporting layer 414, various kinds of electron transporting materials can be used. In this example, the electron transporting layer was formed by a vapor deposition method using $Alq_3$ to have a thickness of 30 nm.

Thereafter, the electron injecting layer 415 was formed. As the electron injecting layer 415, various kinds of electron injecting materials can be used. In this example, the electron injecting layer was formed by a vapor deposition method using calcium fluoride to have a thickness of 1 nm.

After the layer containing the light emitting material 402 was formed by stacking the hole injecting layer 411, the hole transporting layer 412, the light emitting layer 413, the electron transporting layer 414, and the electron injecting layer 415, a second electrode 403 was formed by a sputtering method or a vapor deposition method. In this example, the second electrode functions as a cathode. In this example, the cathode was formed by a vapor deposition method using Al to have a thickness of 200 nm.

Thus, a light emitting element of this example was formed.

Figure 35:
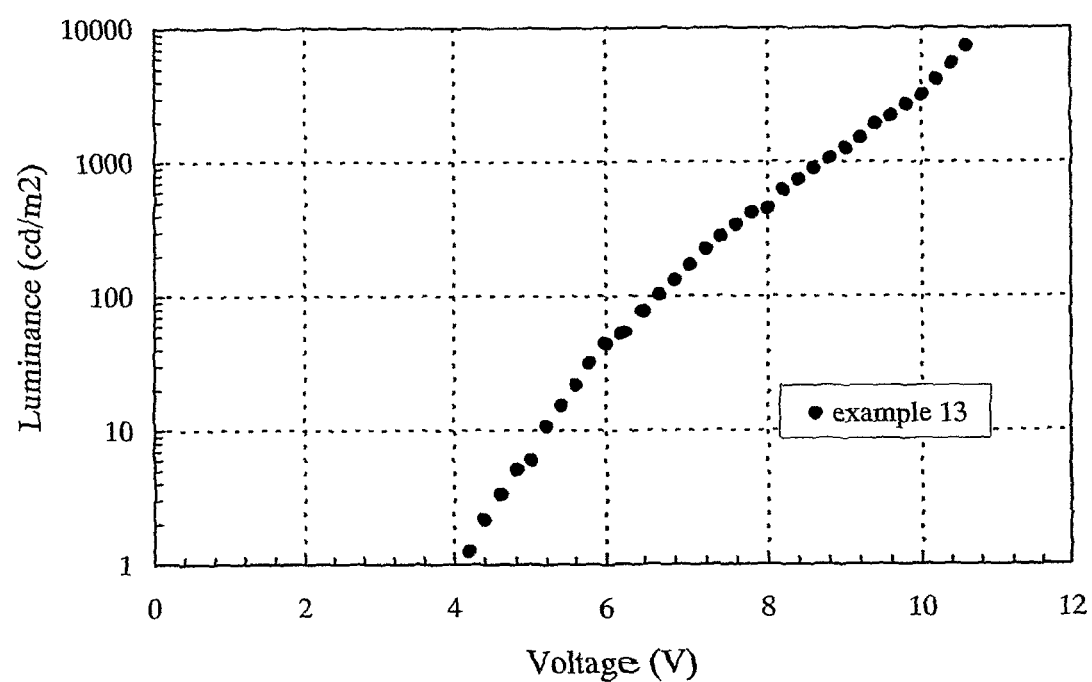
FIG. 35 is a diagram showing luminance-voltage characteristics of a light emitting element manufactured in Example 13.
Figure 36:
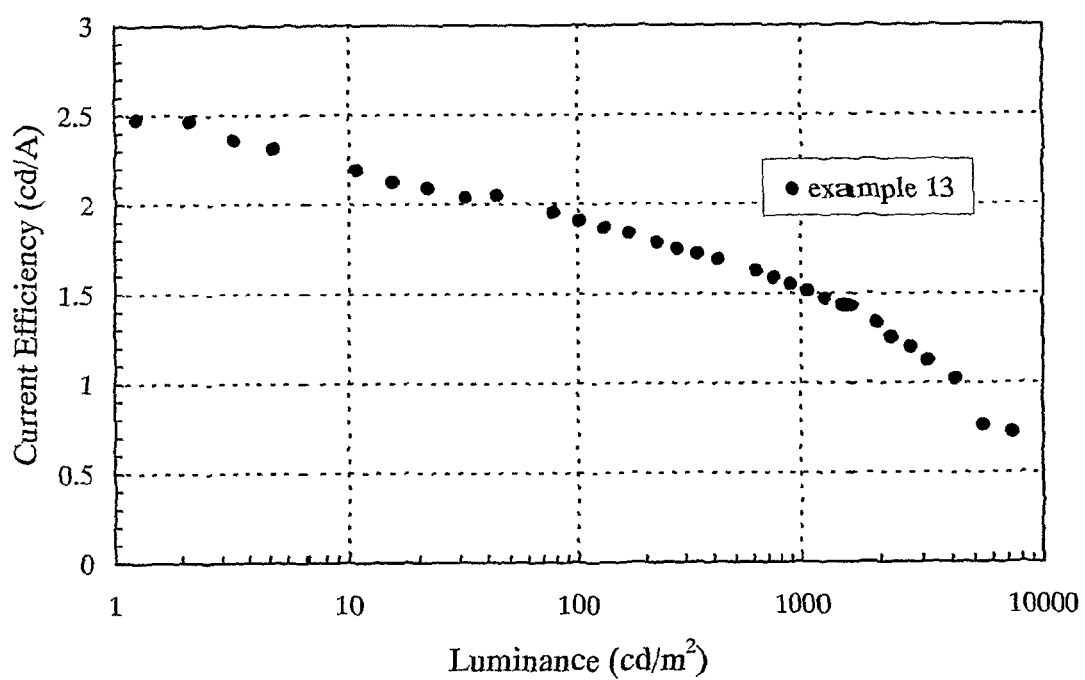
FIG. 36 is a diagram showing current efficiency-luminance characteristics of a light emitting element manufactured in Example 13.
Figure 37:
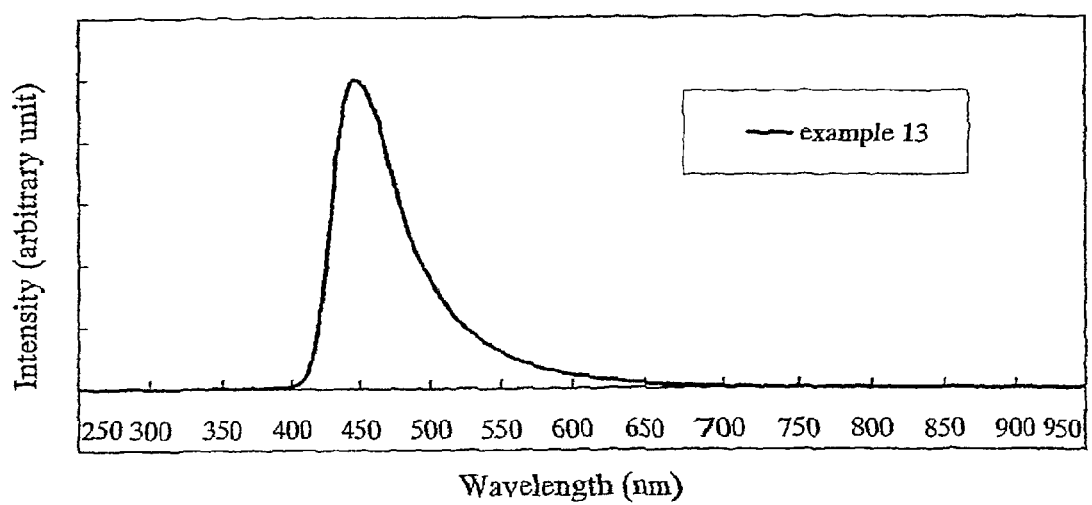
FIG. 37 is a diagram showing an emission spectrum of a light emitting element manufactured in Example 13.

FIG. 35 shows a luminance-voltage characteristic and FIG. 36 shows a current efficiency-luminance characteristic of the light emitting element manufactured in Example 13. FIG. 37 shows an emission spectrum of the light emitting element manufactured in Example 13 when 1 mA of current was supplied.

According to FIGS. 35 and 36, the carbazole derivative according to the present invention can be used as a guest material of the light emitting layer. Specifically, in the case of the light emitting element manufactured in Example 13, voltage required for light emission at luminance of 615 cd/m² was 8.2 V and a current at this time was 1.51 mA (an electric current density was 30.3 mA/cm²). Current efficiency was 1.62 mA/cm² and the chromaticity coordinates were (x, y)= (0.16, 0.12).

As shown in FIG. 37, the light emitting element manufactured in Example 13 has a sharp emission spectrum. Consequently, a light emitting element which emits blue light can be manufactured by using the carbazol carbazole derivative according to the present invention as a light emitting material.

Example 14

In this example, a light emitting element having a carbazol carbazole derivative PCzDPA2 represented by the structural formula (56) will be described with reference of FIG. 34.

A first electrode 401 of the light emitting element was formed over a substrate 400. In this example, the first electrode functions as an anode. The anode was formed by a sputtering method using indium tin oxide containing silicon oxide which was a material for a transparent conductive film to have a thickness of 110 nm.

Then, a layer containing a light emitting material 402 was formed over the first electrode 401. In this example, the layer containing the light emitting material 402 was formed by stacking a hole injecting layer 411, a hole transporting layer 412, a light emitting layer 413, an electron transporting layer 414, and an electron injecting layer 415.

The substrate provided with the first electrode 401 was fixed in a substrate holder in a commercially available vacuum vapor deposition equipment so that the surface provided with the first electrode 401 faces downward. DNTPD was provided to a deposition source in the vacuum vapor deposition equipment to form the hole injecting layer 411 by a vapor deposition method with a resistance heating method to have a thickness of 50 nm.

Then, the hole transporting layer 412 was formed with a material which is excellent in a hole transporting property. As a material for the hole transporting layer 412, various kinds of hole transporting materials can be used. In this example, the hole transporting layer 412 was formed by the same method as that of the hole injecting layer using 2,2',7,7'-tetra(diphenylamino)-spiro-9,9'-bifluorene (abbreviation: spiro-TAD) to have a thickness of 30 nm.

The light emitting layer 413 was formed. In the light emitting layer 413, holes and electrons recombine with each other and emit light. In this example, a host material of 2-tert-butyl-9,10-di(2-naphthyl)anthracene (abbreviation: t-BuDNA) and a guest material of PCzDPA2 represented by the structural formula (56) were co-evaporated to form the light emitting layer 413 having a thickness of 40 nm so that the weight ratio can be 1:0.05 (=t-BuDNA:PCzDPA2). Thereby PCzDPA2 was dispersed in the layer made of t-BuDNA.

The electron transporting layer 414 was formed. As a material for the electron transporting layer 414, various kinds of electron transporting materials can be used. In this example, the electron transporting layer was formed by a vapor deposition method using $Alq_3$ to have a thickness of 30 nm.

Thereafter, the electron injecting layer 415 was formed. As the electron injecting layer 415, various kinds of electron injecting materials can be used. In this example, the electron injecting layer was formed by a vapor deposition method using calcium fluoride to have a thickness of 1 nm.

After the layer containing the light emitting material 402 was formed by stacking the hole injecting layer 411, the hole transporting layer 412, the light emitting layer 413, the electron transporting layer 414, and the electron injecting layer 415, a second electrode 403 was formed by a sputtering method or a vapor deposition method. In this example, the second electrode functions as a cathode. In this example, the cathode was formed by a vapor deposition method using Al to have a thickness of 200 nm.

Thus, a light emitting element of this example was formed.

Figure 38:
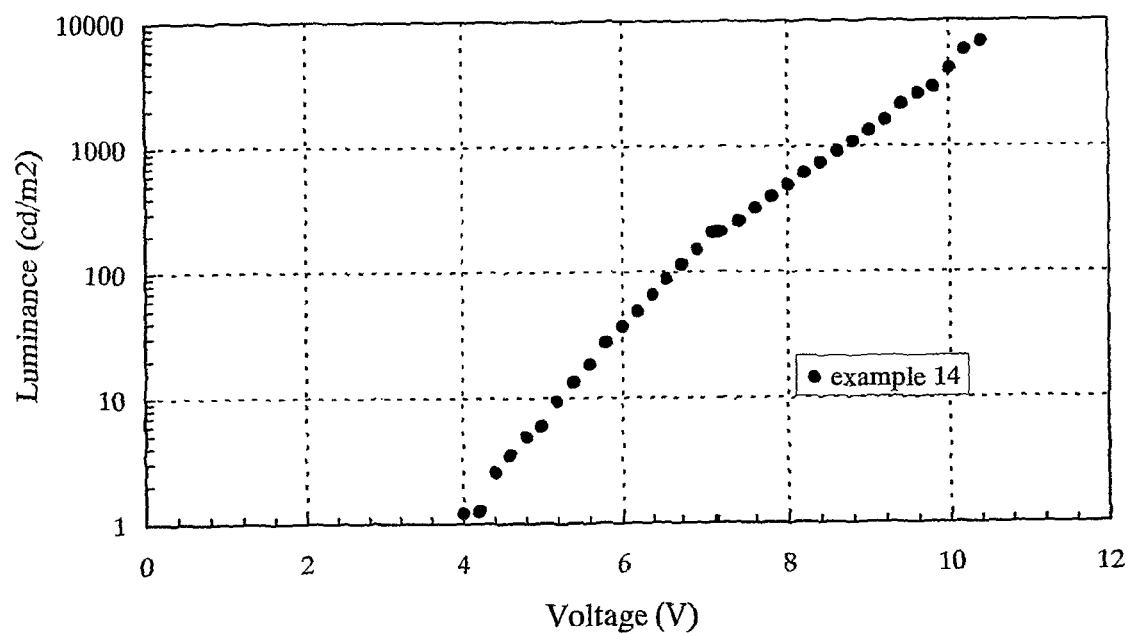
FIG. 38 is a diagram showing luminance-voltage characteristics of a light emitting element manufactured in Example 14.
Figure 39:
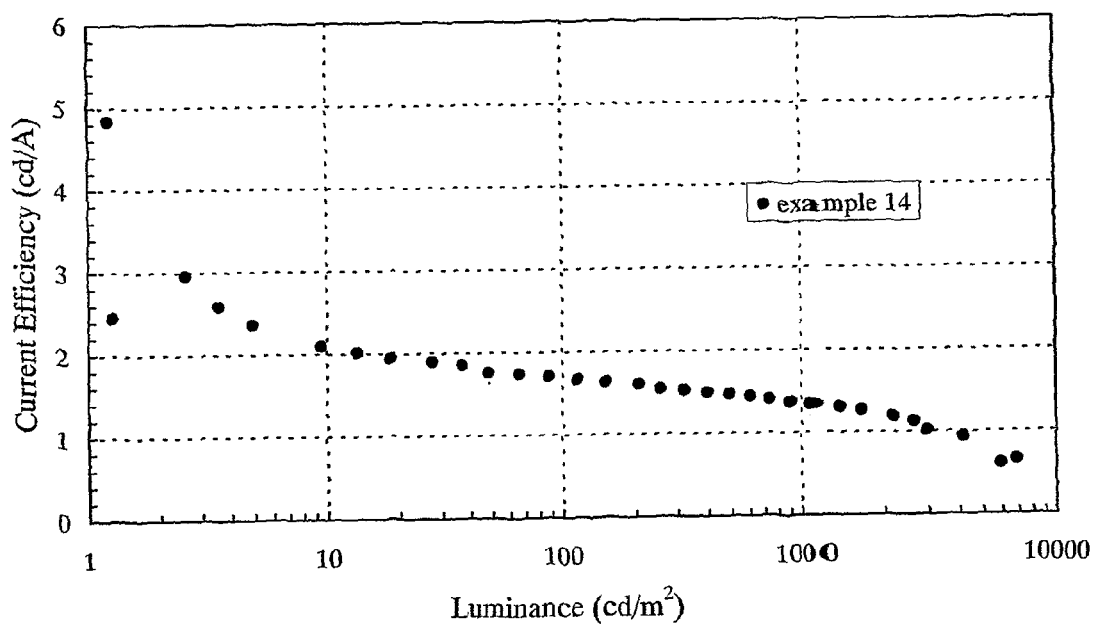
FIG. 39 is a diagram showing current efficiency-luminance characteristics of a light emitting element manufactured in Example 14.
Figure 40:
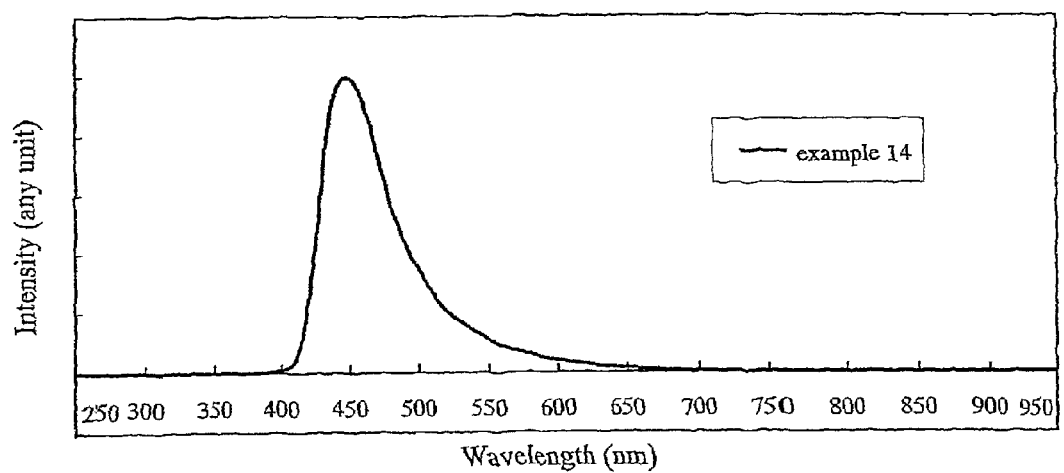
FIG. 40 is a diagram showing an emission spectrum of a light emitting element manufactured in Example 14.

FIG. 38 shows a luminance-voltage characteristic and FIG. 39 shows a current efficiency-luminance characteristic of the light emitting element manufactured in Example 14. FIG. 40 shows an emission spectrum of the light emitting element manufactured in Example 14 when 1 mA of current was supplied.

According to FIGS. 38 and 39, the carbazole derivative according to the present invention can be used as a guest material of the light emitting layer. Specifically, in the case of the light emitting element manufactured in Example 14, voltage required for light emission at luminance of 494 cd/m$^2$ was 8.0 V and a current at this time was 1.34 mA (an electric current density was 33.5 mA/cm$^2$). Current efficiency was 1.47 mA/cm$^2$ and the chromaticity coordinates were (x, y)= (0.16, 0.12).

As shown in FIG. 40, the light emitting element manufactured in Example 14 has a sharp emission spectrum. Consequently, a light emitting element which emits blue light can be manufactured by using the carbazole derivative according to the present invention as a light emitting material.

EXPLANATION OF REFERENCE

101: first electrode, 102: layer containing light emitting material, 103: second electrode, 104: layer being in contact with anode, 200: substrate, 201: first electrode, 202: layer containing light emitting material, 203: second electrode, 204: hole injecting layer, 211: hole transporting layer, 212: light emitting layer, 213: electron transporting layer, 214: electron injecting layer, 300: substrate, 301: first electrode, 302: layer containing light emitting material, 303: second electrode, 311: hole injecting layer, 312: hole transporting layer, 313: light emitting layer, 314: electron transporting layer, 315: electron injecting layer, 400: substrate, 401: first electrode, 402: layer containing light emitting material, 403: second electrode, 411: hole injecting layer, 412: hole transporting layer, 413: light emitting layer, 414: electron transporting layer, 415: electron injecting layer, 601: source side driving circuit, 602: pixel

What is claimed is:

1. A lighting installation comprising a light emitting element, the light emitting element comprising;
a layer interposed between an anode and a cathode, the layer comprising a carbazole derivative represented by a general formula (1),

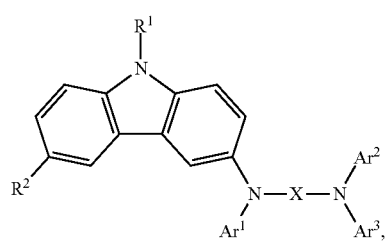

(1)

wherein R$^1$ is selected from hydrogen, an aryl group having 6 to 25 carbon atoms, a heteroaryl group having 5 to 9 carbon atoms, and an acyl group having 1 to 7 carbon atoms, wherein R$^2$ is a substituent represented by a general formula (2),

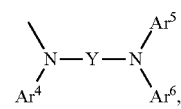

(2)

wherein each of Ar$^1$ to Ar$^6$ is selected from an aryl group having 6 to 25 carbon atoms and a heteroaryl group having 5 to 9 carbon atoms, and wherein each of X and Y is selected from a bivalent aromatic hydrocarbon group having 6 to 25 carbon atoms and a bivalent heterocyclic group having 5 to 10 carbon atoms.

2. The lighting installation according to claim 1, wherein Ar$^1$ and Ar$^4$, Ar$^2$ and Ar$^5$, Ar$^3$ and Ar$^6$, and X and Y have identical structures, respectively.

3. The lighting installation according to claim 1, wherein the layer is in contact with the anode.

4. The lighting installation according to claim 1, wherein the layer further comprises a phosphorescent material.

5. The lighting installation according to claim 1,
wherein the light emitting element further comprises a hole injection layer over and in contact with the anode, and
wherein the layer is formed between the hole injection layer and the cathode.

6. A lighting installation comprising a light emitting element, the light emitting element comprising;
a layer interposed between an anode and a cathode, the layer comprising a carbazole derivative represented by a general formula (3),

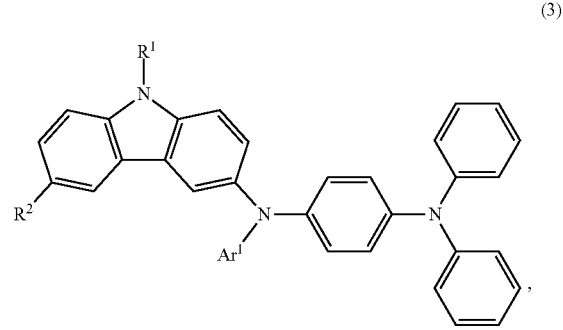

(3)

wherein R$^1$ is selected from hydrogen, an aryl group having 6 to 25 carbon atoms, a heteroaryl group having 5 to 9 carbon atoms, and an acyl group having 1 to 7 carbon atoms, wherein R$^2$ is a substituent represented by a general formula (4),

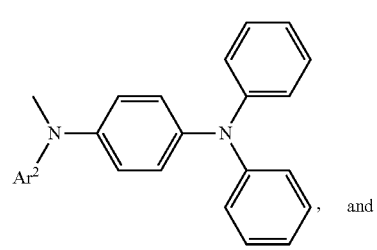

(4)

, and wherein each of Ar$^1$ and Ar$^2$ is selected from an aryl group having 6 to 25 carbon atoms and a heteroaryl group having 5 to 9 carbon atoms.

7. The lighting installation according to claim 6, wherein Ar¹ and Ar² have an identical structure.

8. The lighting installation according to claim 6, wherein the layer is in contact with the anode.

9. The lighting installation according to claim 6, wherein the layer further comprises a phosphorescent material.

10. The lighting installation according to claim 6,
wherein the light emitting element further comprises a hole injection layer over and in contact with the anode, and
wherein the layer is formed between the hole injection layer and the cathode.

11. A lighting installation comprising a light emitting element, the light emitting element comprising:
a layer interposed between an anode and a cathode, the layer comprising a carbazole derivative represented by a general formula (5),

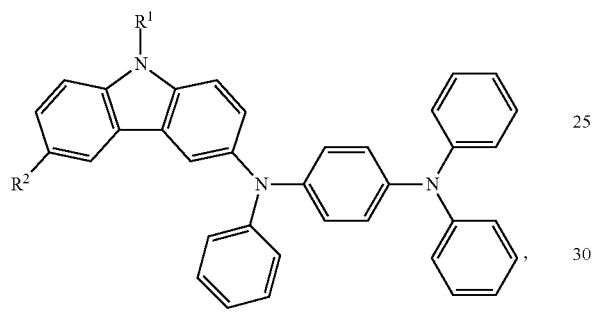
(5)

wherein $R^1$ is selected from hydrogen, an aryl group having 6 to 25 carbon atoms, a heteroaryl group having 5 to 9 carbon atoms, and an acyl group having 1 to 7 carbon atoms, and
wherein $R^2$ is a substituent represented by a general formula (6),

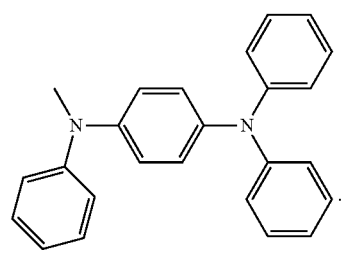
(6)

12. The lighting installation according to claim 11, wherein the layer is in contact with the anode.

13. The lighting installation according to claim 11, wherein the layer further comprises a phosphorescent material.

14. The lighting installation according to claim 11,
wherein the light emitting element further comprises a hole injection layer over and in contact with the anode, and
wherein the layer is formed between the hole injection layer and the cathode.

15. A lighting installation comprising a light emitting element, the light emitting element comprising:
a layer interposed between an anode and a cathode, the layer comprising a carbazole derivative represented by a general formula (103),

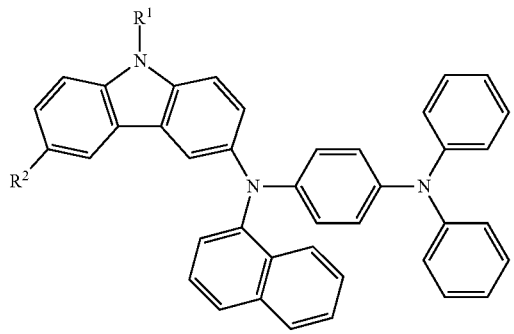
(103)

wherein $R^1$ is selected from hydrogen, an aryl group having 6 to 25 carbon atoms, a heteroaryl group having 5 to 9 carbon atoms, and an acyl group having 1 to 7 carbon atoms, and
wherein $R^2$ is a substituent represented by a general formula (104),

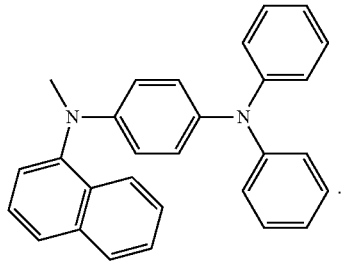
(104)

16. The lighting installation according to claim 15, wherein the layer is in contact with the anode.

17. The lighting installation according to claim 15, wherein the layer further comprises a phosphorescent material.

18. The lighting installation according to claim 15,
wherein the light emitting element further comprises a hole injection layer over and in contact with the anode, and
wherein the layer is formed between the hole injection layer and the cathode.

19. A light emitting element comprising a layer containing a light emitting material interposed between a pair of electrodes,
wherein the layer containing the light emitting material comprises a carbazole derivative represented by a general formula (1) as a host material,

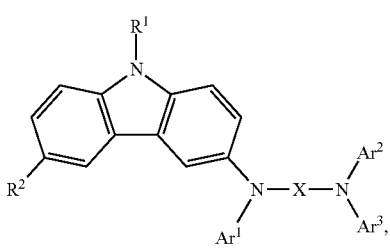
(1)

wherein $R^1$ is one selected from the group consisting of hydrogen, an alkyl group having 1 to 6 carbon atoms, an aryl group having 6 to 25 carbon atoms, a heteroaryl group having 5 to 9 carbon atoms, an arylalkyl group, and an acyl group having 1 to 7 carbon atoms;

wherein $R^2$ is one selected from the group consisting of hydrogen, an alkyl group having 1 to 6 carbon atoms, and a substituent represented by a general formula (2),

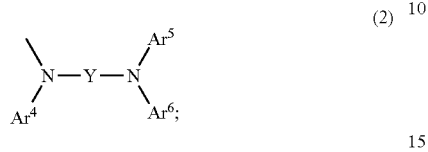

(2)

wherein each of $Ar^1$ to $Ar^6$ is one selected from the group consisting of an aryl group having 6 to 25 carbon atoms and a heteroaryl group having 5 to 9 carbon atoms; and wherein each of X and Y is one selected from the group consisting of a bivalent aromatic hydrocarbon group having 6 to 25 carbon atoms and a bivalent heterocyclic group having 5 to 10 carbon atoms.

20. The light emitting element according to claim 19, wherein $R^1$ is one selected from the group consisting of a methyl group, an ethyl group, a tert-butyl group, and a phenyl group.

21. The light emitting element according to claim 19, wherein $R^2$ is hydrogen or a tert-butyl group.

22. The light emitting element according to claim 19,
wherein $R^2$ has a structure of the general formula (2), and
wherein $Ar^1$ and $Ar^4$, $Ar^2$ and $Ar^5$, $Ar^3$ and $Ar^6$, and X and Y have identical structures, respectively.

23. A lighting installation comprising the light emitting element according to claim 19.

24. A light emitting element comprising a layer containing a light emitting material interposed between a pair of electrodes,
wherein the layer containing the light emitting material comprises a carbazole derivative represented by a general formula (3) as a host material,

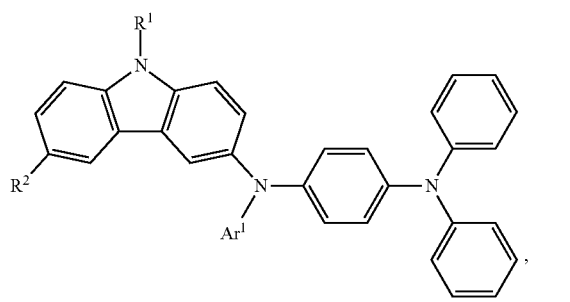

(3)

wherein $R^1$ is one selected from the group consisting of hydrogen, an alkyl group having 1 to 6 carbon atoms, an aryl group having 6 to 25 carbon atoms, a heteroaryl group having 5 to 9 carbon atoms, an arylalkyl group, and an acyl group having 1 to 7 carbon atoms;

wherein $R^2$ is one selected from the group consisting of hydrogen, an alkyl group having 1 to 6 carbon atoms, and a substituent represented by a general formula (4),

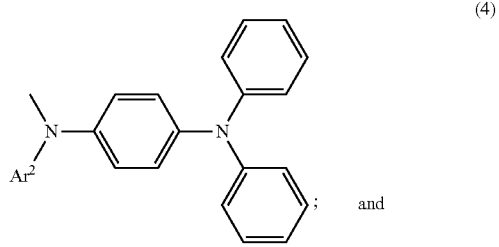

(4)

; and wherein each of $Ar^1$ and $Ar^2$ is one selected from the group consisting of an aryl group having 6 to 25 carbon atoms and a heteroaryl group having 5 to 9 carbon atoms.

25. The light emitting element according to claim 24, wherein $R^1$ is one selected from the group consisting of a methyl group, an ethyl group, a tert-butyl group, and a phenyl group.

26. The light emitting element according to claim 24, wherein $R^2$ is hydrogen or a tert-butyl group.

27. The light emitting element according to claim 24,
wherein $R^2$ has a structure of the general formula (4), and
wherein $Ar^1$ and $Ar^2$ have identical structures.

28. A lighting installation comprising the light emitting element according to claim 24.

29. A light emitting element comprising a layer containing a light emitting material interposed between a pair of electrodes,
wherein the layer containing the light emitting material comprises a carbazole derivative represented by a general formula (5) as a host material,

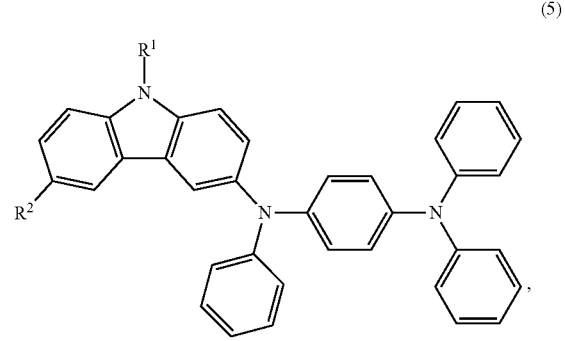

(5)

wherein $R^1$ is one selected from the group consisting of hydrogen, an alkyl group having 1 to 6 carbon atoms, an aryl group having 6 to 25 carbon atoms, a heteroaryl group having 5 to 9 carbon atoms, an arylalkyl group, and an acyl group having 1 to 7 carbon atoms; and wherein $R^2$ is one selected from the group consisting of hydrogen, an alkyl group having 1 to 6 carbon atoms, and a substituent represented by a general formula (6), (6)

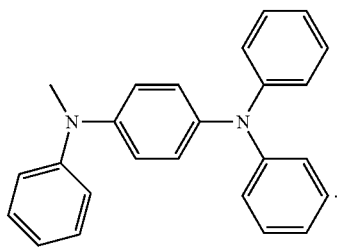

30. The light emitting element according to claim 29, wherein R¹ is one selected from the group consisting of a methyl group, an ethyl group, a tert-butyl group, and a phenyl group.

31. The light emitting element according to claim 29, wherein R² is hydrogen or a tert-butyl group.

32. The light emitting element according to claim 29, wherein R² has a structure of the general formula (6).

33. A lighting installation comprising the light emitting element according to claim 29.

34. A light emitting element comprising a layer containing a light emitting material interposed between a pair of electrodes,
wherein the layer containing the light emitting material comprises a carbazole derivative represented by a general formula (103) as a host material, (103)

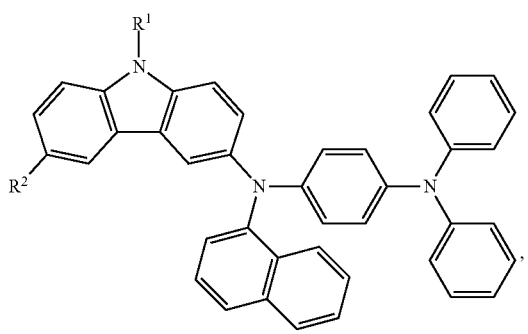

wherein R¹ is one selected from the group consisting of hydrogen, an alkyl group having 1 to 6 carbon atoms, an aryl group having 6 to 25 carbon atoms, a heteroaryl group having 5 to 9 carbon atoms, an arylalkyl group, and an acyl group having 1 to 7 carbon atoms; and wherein R² is one selected from the group consisting of hydrogen, an alkyl group having 1 to 6 carbon atoms, and a substituent represented by a general formula (104), (104)

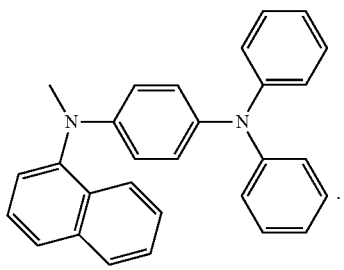

35. The light emitting element according to claim 34, wherein R¹ is one selected from the group consisting of a methyl group, an ethyl group, a tert-butyl group, and a phenyl group.

36. The light emitting element according to claim 34, wherein R² is hydrogen or a tert-butyl group.

37. The light emitting element according to claim 34, wherein R² has a structure of the general formula (104).

38. A lighting installation comprising the light emitting element according to claim 34.

39. An organic compound having the following structure,

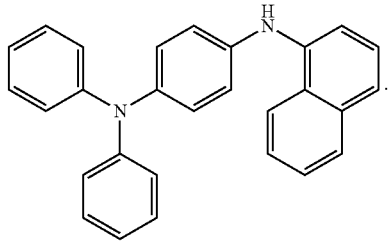 [SMILES: c1ccc(N(c2ccccc2)c2ccc(Nc3cccc4ccccc34)cc2)cc1]

* * * * *